United States Patent
Bojack et al.

(10) Patent No.: US 9,204,640 B2
(45) Date of Patent: Dec. 8, 2015

(54) 2-ACYLOXY-PYRROLIN-4-ONES

(75) Inventors: Guido Bojack, Wiesbaden-Naurod (DE); Taraneh Farida, Pulheim (DE); Reiner Fischer, Monheim (DE); Stefan Lehr, Lyons (FR); Albert Schnatterer, Leverkusen (DE); Thomas Auler, Bergisch Gladbach (DE); Ulrich Görgens, Ratingen (DE); Heinz Kehne, Hofheim (DE); Olga Malsam, Roesrath (DE)

(73) Assignee: BAYER INTELLECTUAL PROPERTY GMBH, Monheim (DE)

(*) Notice: Subject to any disclaimer, the term of this patent is extended or adjusted under 35 U.S.C. 154(b) by 140 days.

(21) Appl. No.: 14/002,697

(22) PCT Filed: Feb. 27, 2012

(86) PCT No.: PCT/EP2012/053289
§ 371 (c)(1),
(2), (4) Date: Nov. 12, 2013

(87) PCT Pub. No.: WO2012/116960
PCT Pub. Date: Sep. 7, 2012

(65) Prior Publication Data
US 2014/0057790 A1  Feb. 27, 2014

Related U.S. Application Data

(60) Provisional application No. 61/447,858, filed on Mar. 1, 2011.

(30) Foreign Application Priority Data

Mar. 1, 2011 (EP) .................................... 11156415

(51) Int. Cl.
| | | |
|---|---|---|
| A01N 43/36 | (2006.01) |
| C07D 207/38 | (2006.01) |
| C07D 209/54 | (2006.01) |
| C07D 471/10 | (2006.01) |
| C07D 491/107 | (2006.01) |
| C07D 491/113 | (2006.01) |
| C07D 495/10 | (2006.01) |
| A01N 47/06 | (2006.01) |
| A01N 43/38 | (2006.01) |

(52) U.S. Cl.
CPC ............. *A01N 43/36* (2013.01); *A01N 43/38* (2013.01); *A01N 47/06* (2013.01); *C07D 207/38* (2013.01); *C07D 209/54* (2013.01); *C07D 471/10* (2013.01); *C07D 491/107* (2013.01); *C07D 491/113* (2013.01); *C07D 495/10* (2013.01)

(58) Field of Classification Search
CPC ..... A01N 43/36; A01N 47/06; C07D 413/04; C07C 59/64; C07C 69/734; C07C 235/34
USPC .................. 504/283; 548/408, 544
See application file for complete search history.

(56) References Cited

U.S. PATENT DOCUMENTS

| | | | |
|---|---|---|---|
| 2,842,476 A | 7/1958 | Schreiber |
| 4,623,727 A | 11/1986 | Hubele et al. |
| 4,639,266 A | 1/1987 | Heubach et al. |
| 4,844,734 A | 7/1989 | Iwasaki et al. |

(Continued)

FOREIGN PATENT DOCUMENTS

| | | |
|---|---|---|
| CA | 1162071 A1 | 2/1984 |
| DE | 102005059892 | 6/2007 |

(Continued)

OTHER PUBLICATIONS 05-3215 Gam/Ii/XP/V2005-10-25: Alkylthio-spirocyclic tetramic acids.

(Continued)

*Primary Examiner* — Johann R Richter
*Assistant Examiner* — Yanzhi Zhang
(74) *Attorney, Agent, or Firm* — Miles and Stockbridge

(57) ABSTRACT

The invention relates to novel 2-acyloxypyrrolin-4-ones of the formula (I)

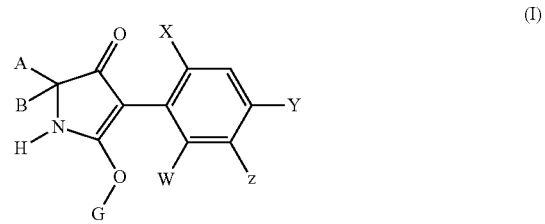

in which A, B, G, W, X, Y and Z have the meaning given above, to a plurality of processes and intermediates for their preparation, and to their use as pesticides and/or herbicides.

The invention also relates to selective herbicidal compositions comprising, firstly, the 2-acyloxypyrrolin-4-ones and, secondly, a crop plant compatibility-improving compound.

The present invention furthermore relates to the boosting of the action of crop protection compositions comprising, in particular, 2-acyloxypyrrolin-4-ones, through the addition of ammonium salts or phosphonium salts and optionally penetrants, to the corresponding compositions, to processes for producing them and to their application in crop protection as insecticides and/or nematicides and/or acaricides and/or for preventing unwanted plant growth.

10 Claims, No Drawings

(56) References Cited

U.S. PATENT DOCUMENTS

| | | |
|---|---|---|
| 4,881,966 A | 11/1989 | Nyffeler et al. |
| 4,888,049 A | 12/1989 | Iwasaki et al. |
| 4,891,057 A | 1/1990 | Sohn et al. |
| 4,902,340 A | 2/1990 | Hubele et al. |
| 4,944,790 A | 7/1990 | Moser et al. |
| 4,985,063 A | 1/1991 | Fischer et al. |
| 5,013,659 A | 5/1991 | Bedbrook et al. |
| 5,045,560 A | 9/1991 | Fischer et al. |
| 5,116,836 A | 5/1992 | Fischer et al. |
| 5,215,570 A | 6/1993 | Burckhardt et al. |
| 5,225,434 A | 7/1993 | Bertram et al. |
| 5,258,527 A | 11/1993 | Krauskopf et al. |
| 5,314,863 A | 5/1994 | Loher et al. |
| 5,380,852 A | 1/1995 | Schuetze et al. |
| 5,401,700 A | 3/1995 | Sohn et al. |
| 5,462,912 A | 10/1995 | Hioki et al. |
| 5,462,913 A | 10/1995 | Fischer et al. |
| 5,500,367 A | 3/1996 | Hain et al. |
| 5,504,057 A | 4/1996 | Fischer et al. |
| 5,516,750 A | 5/1996 | Willms et al. |
| 5,538,937 A | 7/1996 | Hasebe et al. |
| 5,567,671 A | 10/1996 | Fischer et al. |
| 5,589,469 A | 12/1996 | Fischer et al. |
| 5,602,078 A | 2/1997 | Fischer et al. |
| 5,616,536 A | 4/1997 | Fischer et al. |
| 5,622,917 A | 4/1997 | Fischer et al. |
| 5,677,449 A | 10/1997 | Fischer et al. |
| 5,683,965 A | 11/1997 | Bachmann et al. |
| 5,689,046 A | 11/1997 | Schroeder et al. |
| 5,700,758 A | 12/1997 | Roesch et al. |
| 5,705,476 A | 1/1998 | Hoffarth |
| 5,739,079 A | 4/1998 | Holdgruen et al. |
| 5,792,755 A | 8/1998 | Sagenmueller et al. |
| 5,811,374 A | 9/1998 | Bertram et al. |
| 5,830,826 A | 11/1998 | Fischer et al. |
| 5,847,211 A | 12/1998 | Fischer et al. |
| 5,972,839 A | 10/1999 | Ziemer et al. |
| 5,994,274 A | 11/1999 | Fischer et al. |
| 6,110,872 A | 8/2000 | Lieb et al. |
| 6,114,374 A | 9/2000 | Lieb et al. |
| 6,133,296 A | 10/2000 | Lieb et al. |
| 6,140,358 A | 10/2000 | Lieb et al. |
| 6,172,255 B1 | 1/2001 | Fischer et al. |
| 6,200,932 B1 | 3/2001 | Fischer et al. |
| 6,235,680 B1 | 5/2001 | Ziemer et al. |
| 6,251,803 B1 | 6/2001 | Lee et al. |
| 6,251,827 B1 | 6/2001 | Ziemer et al. |
| 6,255,342 B1 | 7/2001 | Lieb et al. |
| 6,271,180 B2 | 8/2001 | Lieb et al. |
| 6,288,102 B1 | 9/2001 | Hagemann et al. |
| 6,316,486 B1 | 11/2001 | Lieb et al. |
| 6,359,151 B2 | 3/2002 | Lieb et al. |
| 6,380,246 B1 | 4/2002 | Lieb et al. |
| 6,388,123 B1 | 5/2002 | Lieb et al. |
| 6,417,370 B1 | 7/2002 | Lieb et al. |
| 6,451,843 B1 | 9/2002 | Lieb et al. |
| 6,458,965 B1 | 10/2002 | Lieb et al. |
| 6,469,196 B2 | 10/2002 | Fischer et al. |
| 6,472,419 B1 | 10/2002 | Fischer et al. |
| 6,486,343 B1 | 11/2002 | Lieb et al. |
| 6,504,036 B1 | 1/2003 | Lieb et al. |
| 6,511,942 B1 | 1/2003 | Lieb et al. |
| 6,589,976 B1 | 7/2003 | Fischer et al. |
| 6,596,873 B1 | 7/2003 | Lieb et al. |
| 6,602,823 B1 | 8/2003 | Rochling et al. |
| 6,608,211 B1 | 8/2003 | Hagemann et al. |
| 6,645,914 B1 | 11/2003 | Woznica et al. |
| 6,670,488 B1 | 12/2003 | Hagemann et al. |
| 6,693,092 B2 | 2/2004 | Lieb et al. |
| 6,716,832 B2 | 4/2004 | Lieb et al. |
| 6,759,548 B2 | 7/2004 | Fischer et al. |
| 6,806,264 B2 | 10/2004 | Lieb et al. |
| 6,858,741 B2 | 2/2005 | Lieb et al. |
| 6,861,391 B1 | 3/2005 | Fischer et al. |
| 6,894,005 B1 | 5/2005 | Maetzke et al. |
| 6,900,341 B2 | 5/2005 | Hagemann et al. |
| 6,933,261 B2 | 8/2005 | Lieb et al. |
| 6,939,888 B2 | 9/2005 | Fischer et al. |
| 7,105,471 B2 | 9/2006 | Lieb et al. |
| 7,109,370 B2 | 9/2006 | Hagemann et al. |
| 7,256,158 B2 | 8/2007 | Lieb et al. |
| 7,288,676 B2 | 10/2007 | Lieb et al. |
| 7,432,225 B2 | 10/2008 | Fischer et al. |
| 7,638,547 B2 | 12/2009 | Himmler et al. |
| 7,718,186 B2 | 5/2010 | Fischer et al. |
| 7,718,706 B2 | 5/2010 | Lieb et al. |
| 7,727,933 B2 | 6/2010 | Fischer et al. |
| 7,754,654 B2 | 7/2010 | Fischer et al. |
| 7,776,791 B2 | 8/2010 | Fischer et al. |
| 7,888,285 B2 | 2/2011 | Fischer et al. |
| 7,897,543 B2 | 3/2011 | Bretschneider et al. |
| 7,897,803 B2 | 3/2011 | Himmler et al. |
| 7,915,282 B2 | 3/2011 | Ruther et al. |
| 7,947,704 B2 | 5/2011 | Bretschneider et al. |
| 8,013,172 B2 | 9/2011 | Fischer et al. |
| 8,039,014 B2* | 10/2011 | Fischer et al. .............. 424/405 |
| 8,058,210 B2 | 11/2011 | Lieb et al. |
| 8,067,458 B2 | 11/2011 | Fischer et al. |
| 8,138,119 B2 | 3/2012 | Fischer et al. |
| 8,138,350 B2 | 3/2012 | Jeschke et al. |
| 8,173,697 B2 | 5/2012 | Fischer et al. |
| 8,193,120 B2 | 6/2012 | Ruther et al. |
| 8,314,254 B2 | 11/2012 | Fischer et al. |
| 8,334,300 B2 | 12/2012 | Ruther et al. |
| 8,383,853 B2 | 2/2013 | Fischer et al. |
| 8,389,443 B2 | 3/2013 | Fischer et al. |
| 8,410,289 B2 | 4/2013 | Fischer et al. |
| 8,435,549 B2 | 5/2013 | Fischer et al. |
| 8,507,537 B2 | 8/2013 | Fischer et al. |
| 8,518,985 B2 | 8/2013 | Fischer et al. |
| 2001/0004629 A1 | 6/2001 | Lieb et al. |
| 2002/0010204 A1 | 1/2002 | Lieb et al. |
| 2002/0022575 A1 | 2/2002 | Fischer et al. |
| 2002/0188136 A1 | 12/2002 | Lieb et al. |
| 2003/0045432 A1 | 3/2003 | Fischer et al. |
| 2003/0073851 A1 | 4/2003 | Lieb et al. |
| 2003/0096806 A1 | 5/2003 | Lieb et al. |
| 2003/0144504 A1 | 7/2003 | Fischer et al. |
| 2003/0171219 A1 | 9/2003 | Lieb et al. |
| 2003/0199572 A1 | 10/2003 | Lieb et al. |
| 2003/0216260 A1 | 11/2003 | Ruther et al. |
| 2003/0224939 A1 | 12/2003 | Miles |
| 2003/0228984 A1 | 12/2003 | Hagemann et al. |
| 2004/0019061 A1 | 1/2004 | Fischer et al. |
| 2004/0102327 A1 | 5/2004 | Hagemann et al. |
| 2004/0116744 A1 | 6/2004 | Furuya et al. |
| 2004/0127365 A1 | 7/2004 | Lieb et al. |
| 2004/0167031 A1 | 8/2004 | Lieb et al. |
| 2004/0224844 A1 | 11/2004 | Bickers et al. |
| 2005/0009880 A1 | 1/2005 | Cottrell et al. |
| 2005/0037922 A1 | 2/2005 | Bickers et al. |
| 2005/0038021 A1 | 2/2005 | Lieb et al. |
| 2005/0049145 A1 | 3/2005 | Bickers et al. |
| 2005/0054535 A1 | 3/2005 | Fischer et al. |
| 2005/0096386 A1 | 5/2005 | Cottrell et al. |
| 2005/0164883 A1 | 7/2005 | Maetzke et al. |
| 2005/0164885 A1 | 7/2005 | Lieb et al. |
| 2005/0187111 A1 | 8/2005 | Hagemann et al. |
| 2005/0256000 A1 | 11/2005 | Schaper et al. |
| 2006/0122061 A1 | 6/2006 | Lieb et al. |
| 2006/0160847 A1 | 7/2006 | Fischer et al. |
| 2006/0166829 A1 | 7/2006 | Fischer et al. |
| 2007/0015664 A1 | 1/2007 | Fischer et al. |
| 2007/0032539 A1 | 2/2007 | Himmler |
| 2007/0066617 A1 | 3/2007 | Mita et al. |
| 2007/0129252 A1 | 6/2007 | Fischer et al. |
| 2007/0129407 A1 | 6/2007 | Koyanagi et al. |
| 2007/0225167 A1 | 9/2007 | Fischer et al. |
| 2007/0225170 A1 | 9/2007 | Fischer et al. |
| 2007/0244007 A1 | 10/2007 | Fischer et al. |
| 2007/0275858 A1 | 11/2007 | Fischer et al. |
| 2007/0298968 A1 | 12/2007 | Bretschneider et al. |
| 2007/0298969 A1 | 12/2007 | Fischer et al. |
| 2008/0081807 A1 | 4/2008 | Lieb et al. |

(56) References Cited

U.S. PATENT DOCUMENTS

| | | | |
|---|---|---|---|
| 2008/0167188 A1 | 7/2008 | Fischer et al. |
| 2008/0220973 A1 | 9/2008 | Fischer et al. |
| 2008/0269052 A1 | 10/2008 | Rosinger et al. |
| 2008/0269059 A1 | 10/2008 | Ziemer et al. |
| 2008/0305955 A1 | 12/2008 | Bretschneider et al. |
| 2008/0318776 A1 | 12/2008 | Fischer et al. |
| 2009/0029858 A1 | 1/2009 | Fischer et al. |
| 2009/0076282 A1 | 3/2009 | Toriyabe et al. |
| 2009/0111847 A1 | 4/2009 | Li et al. |
| 2009/0209513 A1 | 8/2009 | Fischer et al. |
| 2009/0215624 A1 | 8/2009 | Fischer et al. |
| 2009/0227563 A1 | 9/2009 | Fischer et al. |
| 2009/0239906 A1 | 9/2009 | Fischer et al. |
| 2009/0247551 A1 | 10/2009 | Jeschke et al. |
| 2009/0253749 A1 | 10/2009 | Jeschke et al. |
| 2009/0259046 A1 | 10/2009 | Hamamoto et al. |
| 2009/0298828 A1 | 12/2009 | Fischer et al. |
| 2009/0305891 A1 * | 12/2009 | Fischer et al. ............ 504/130 |
| 2010/0004127 A1 | 1/2010 | Fischer et al. |
| 2010/0009850 A1 | 1/2010 | Fischer et al. |
| 2010/0056598 A1 | 3/2010 | Himmler et al. |
| 2010/0087320 A1 | 4/2010 | Lieb et al. |
| 2010/0174084 A1 | 7/2010 | Fischer et al. |
| 2010/0234229 A1 | 9/2010 | Fischer et al. |
| 2010/0240705 A1 | 9/2010 | Jeschke et al. |
| 2010/0240924 A1 | 9/2010 | Fischer et al. |
| 2010/0256195 A1 | 10/2010 | Fischer et al. |
| 2010/0261608 A1 | 10/2010 | Fischer et al. |
| 2010/0261934 A1 | 10/2010 | Fischer et al. |
| 2010/0267964 A1 | 10/2010 | Fischer et al. |
| 2010/0279873 A1 | 11/2010 | Fischer et al. |
| 2010/0311593 A1 | 12/2010 | Fischer et al. |
| 2011/0086762 A1 | 4/2011 | Fischer et al. |
| 2011/0092368 A1 | 4/2011 | Fischer et al. |
| 2011/0130284 A1 | 6/2011 | Fischer et al. |
| 2011/0143943 A1 | 6/2011 | Ruther et al. |
| 2011/0183849 A1 | 7/2011 | Ruther et al. |
| 2011/0190493 A1 | 8/2011 | Bretschneider et al. |
| 2011/0195842 A1 | 8/2011 | Bretschneider et al. |
| 2011/0195998 A1 | 8/2011 | Goto et al. |
| 2011/0212949 A1 | 9/2011 | Bretschneider et al. |
| 2011/0213160 A1 | 9/2011 | Bretschneider et al. |
| 2011/0230346 A1 | 9/2011 | Fischer et al. |
| 2011/0230351 A1 | 9/2011 | Fischer et al. |
| 2011/0263424 A1 | 10/2011 | Bretschneider et al. |
| 2011/0306499 A1 | 12/2011 | Bretschneider et al. |
| 2012/0004105 A1 | 1/2012 | Zambach et al. |
| 2012/0012833 A1 | 1/2012 | Shirasawa et al. |
| 2012/0015807 A1 | 1/2012 | Fischer et al. |
| 2012/0178927 A1 | 7/2012 | Fischer et al. |
| 2012/0238450 A1 | 9/2012 | Ruther et al. |
| 2013/0040935 A1 | 2/2013 | Liu et al. |

FOREIGN PATENT DOCUMENTS

| | | |
|---|---|---|
| DE | 102005059892 A1 | 6/2007 |
| DE | 102010008642 | 8/2011 |
| DE | 102010008642 A1 | 8/2011 |
| DE | 102010008643 | 8/2011 |
| DE | 102010008643 A1 | 8/2011 |
| EP | 0036106 A2 | 9/1981 |
| EP | 0036106 A3 | 9/1981 |
| EP | 0086750 A2 | 8/1983 |
| EP | 0094349 A2 | 11/1983 |
| EP | 0142924 A2 | 5/1985 |
| EP | 0174562 A2 | 3/1986 |
| EP | 0191736 A2 | 8/1986 |
| EP | 0193259 A1 | 9/1986 |
| EP | 0174562 A3 | 1/1987 |
| EP | 0221044 A1 | 5/1987 |
| EP | 0242236 A1 | 10/1987 |
| EP | 0242246 A1 | 10/1987 |
| EP | 0142924 A3 | 12/1987 |
| EP | 0191736 A3 | 1/1988 |
| EP | 0257993 A2 | 3/1988 |
| EP | 0262399 | 4/1988 |
| EP | 0262399 A2 | 4/1988 |
| EP | 0268554 A2 | 5/1988 |
| EP | 0268554 A3 | 6/1988 |
| EP | 0269806 A1 | 6/1988 |
| EP | 0305398 A1 | 3/1989 |
| EP | 0262399 A3 | 4/1989 |
| EP | 0309862 A1 | 4/1989 |
| EP | 0333131 A1 | 9/1989 |
| EP | 0346620 A1 | 12/1989 |
| EP | 0355599 | 2/1990 |
| EP | 0355599 A1 | 2/1990 |
| EP | 0365484 A1 | 4/1990 |
| EP | 0257993 A3 | 5/1990 |
| EP | 0377893 | 7/1990 |
| EP | 0377893 A2 | 7/1990 |
| EP | 0415211 | 3/1991 |
| EP | 0415211 A2 | 3/1991 |
| EP | 0377893 A3 | 4/1991 |
| EP | 0442073 | 8/1991 |
| EP | 0442073 A2 | 8/1991 |
| EP | 0442077 | 8/1991 |
| EP | 0442077 A2 | 8/1991 |
| EP | 0613885 | 9/1991 |
| EP | 0453086 A2 | 10/1991 |
| EP | 0456063 | 11/1991 |
| EP | 0456063 A2 | 11/1991 |
| EP | 0415211 A3 | 1/1992 |
| EP | 0464461 A2 | 1/1992 |
| EP | 0442073 A3 | 3/1992 |
| EP | 0442077 A3 | 3/1992 |
| EP | 0464461 A3 | 3/1992 |
| EP | 0456063 A3 | 7/1992 |
| EP | 0492366 A2 | 7/1992 |
| EP | 0131624 B1 | 9/1992 |
| EP | 0453086 A3 | 9/1992 |
| EP | 0492366 A3 | 11/1992 |
| EP | 0521334 | 1/1993 |
| EP | 0521334 A1 | 1/1993 |
| EP | 0539588 A1 | 5/1993 |
| EP | 0582198 A2 | 2/1994 |
| EP | 0596298 | 5/1994 |
| EP | 0596298 A2 | 5/1994 |
| EP | 0596298 A3 | 7/1994 |
| EP | 0613884 | 9/1994 |
| EP | 0613884 A2 | 9/1994 |
| EP | 0613885 A2 | 9/1994 |
| EP | 0613884 A3 | 11/1994 |
| EP | 0613885 A3 | 11/1994 |
| EP | 0582198 A3 | 4/1995 |
| EP | 0664081 A2 | 7/1995 |
| EP | 0668267 | 8/1995 |
| EP | 0668267 A1 | 8/1995 |
| EP | 0681865 A2 | 11/1995 |
| EP | 0681865 A3 | 3/1996 |
| EP | 0664081 A3 | 10/1996 |
| EP | 002646335 | 6/2008 |
| FR | 2600494 A1 | 12/1987 |
| GB | 2266888 | 11/1993 |
| GB | 2266888 A | 11/1993 |
| JP | 6087254 A | 5/1985 |
| JP | 2000-053670 | 2/2000 |
| JP | 2000053670 A | 2/2000 |
| JP | 2000205984 A | 7/2000 |
| JP | 2002-2005984 | 7/2002 |
| JP | 2008110953 A | 5/2008 |
| JP | 2010018586 A | 1/2010 |
| WO | 8402919 A1 | 8/1984 |
| WO | 8706766 A1 | 11/1987 |
| WO | 8910396 A1 | 11/1989 |
| WO | 9107874 A1 | 6/1991 |
| WO | 9108202 A1 | 6/1991 |
| WO | 9113972 A1 | 9/1991 |
| WO | 9119806 A1 | 12/1991 |
| WO | 9200377 A1 | 1/1992 |
| WO | 9211376 A1 | 7/1992 |
| WO | 9214827 A1 | 9/1992 |
| WO | 9216108 A1 | 10/1992 |

(56) References Cited

FOREIGN PATENT DOCUMENTS

| | | |
|---|---|---|
| WO | 9501971 | 1/1995 |
| WO | 9501971 A1 | 1/1995 |
| WO | 9507897 A1 | 3/1995 |
| WO | 9517817 A1 | 7/1995 |
| WO | 9520572 | 8/1995 |
| WO | 9520572 A1 | 8/1995 |
| WO | 9525395 | 9/1995 |
| WO | 9526954 | 10/1995 |
| WO | 9526954 A1 | 10/1995 |
| WO | 9625395 A1 | 8/1996 |
| WO | 96033270 A1 | 10/1996 |
| WO | 9635664 | 11/1996 |
| WO | 9635664 A1 | 11/1996 |
| WO | 9701535 | 1/1997 |
| WO | 9701535 A1 | 1/1997 |
| WO | 9702243 | 1/1997 |
| WO | 9702243 A1 | 1/1997 |
| WO | 9736868 | 10/1997 |
| WO | 9736868 A1 | 10/1997 |
| WO | 9743275 | 11/1997 |
| WO | 9743275 A2 | 11/1997 |
| WO | 9745016 A1 | 12/1997 |
| WO | 9805368 | 2/1998 |
| WO | 9805638 A1 | 2/1998 |
| WO | 9806721 | 2/1998 |
| WO | 9806721 A1 | 2/1998 |
| WO | 9813361 A1 | 4/1998 |
| WO | 9825928 | 6/1998 |
| WO | 9825928 A1 | 6/1998 |
| WO | 9827049 A1 | 6/1998 |
| WO | 9835553 A1 | 8/1998 |
| WO | 9838856 A1 | 9/1998 |
| WO | 9900020 A1 | 1/1999 |
| WO | 9916744 A1 | 4/1999 |
| WO | 9916748 | 4/1999 |
| WO | 9916748 A1 | 4/1999 |
| WO | 9924437 | 5/1999 |
| WO | 9924437 A1 | 5/1999 |
| WO | 9943649 | 9/1999 |
| WO | 9943649 A1 | 9/1999 |
| WO | 9948869 | 9/1999 |
| WO | 9948869 A1 | 9/1999 |
| WO | 9955673 | 11/1999 |
| WO | 9955673 A1 | 11/1999 |
| WO | 0035278 A1 | 6/2000 |
| WO | 0117972 | 3/2001 |
| WO | 0117972 A2 | 3/2001 |
| WO | 0123354 | 4/2001 |
| WO | 0123354 A2 | 4/2001 |
| WO | 0117972 A3 | 9/2001 |
| WO | 0174770 | 10/2001 |
| WO | 0174770 A1 | 10/2001 |
| WO | 0123354 A3 | 2/2002 |
| WO | 0234048 A1 | 5/2002 |
| WO | 0296882 A1 | 12/2002 |
| WO | 03013249 | 2/2003 |
| WO | 03013249 A1 | 2/2003 |
| WO | 03059065 | 7/2003 |
| WO | 03059065 A1 | 7/2003 |
| WO | 03062244 | 7/2003 |
| WO | 03062244 A1 | 7/2003 |
| WO | 03106457 A1 | 12/2003 |
| WO | 2004007448 | 1/2004 |
| WO | 2004007448 A1 | 1/2004 |
| WO | 2004024688 | 3/2004 |
| WO | 2004024688 A1 | 3/2004 |
| WO | 2004065366 | 8/2004 |
| WO | 2004065366 A1 | 8/2004 |
| WO | 2004080962 | 9/2004 |
| WO | 2004080962 A1 | 9/2004 |
| WO | 2004084631 A1 | 10/2004 |
| WO | 2004099160 A1 | 11/2004 |
| WO | 2004111042 | 12/2004 |
| WO | 2004111042 A1 | 12/2004 |
| WO | 2005015994 A1 | 2/2005 |
| WO | 2005016001 A1 | 2/2005 |
| WO | 2005035486 A1 | 4/2005 |
| WO | 2005044791 | 5/2005 |
| WO | 2005044791 A1 | 5/2005 |
| WO | 2005044796 | 5/2005 |
| WO | 2005044796 A1 | 5/2005 |
| WO | 2005048710 | 6/2005 |
| WO | 2005048710 A1 | 6/2005 |
| WO | 2005049569 | 6/2005 |
| WO | 2005049569 A1 | 6/2005 |
| WO | 2005066125 | 7/2005 |
| WO | 2005066125 A1 | 7/2005 |
| WO | 2005077934 A1 | 8/2005 |
| WO | 2005085216 A1 | 9/2005 |
| WO | 2005092897 | 10/2005 |
| WO | 2005092897 A1 | 10/2005 |
| WO | 2005112630 A1 | 12/2005 |
| WO | 2006000355 | 1/2006 |
| WO | 2006000355 A1 | 1/2006 |
| WO | 2006024411 | 3/2006 |
| WO | 2006024411 A1 | 3/2006 |
| WO | 2006029799 | 3/2006 |
| WO | 2006029799 A1 | 3/2006 |
| WO | 2006043635 A1 | 4/2006 |
| WO | 2006056281 | 6/2006 |
| WO | 2006056281 A1 | 6/2006 |
| WO | 2006056282 | 6/2006 |
| WO | 2006056282 A1 | 6/2006 |
| WO | 2006056433 A1 | 6/2006 |
| WO | 2006089633 | 8/2006 |
| WO | 2006089633 A2 | 8/2006 |
| WO | 2006100288 A2 | 9/2006 |
| WO | 2006089633 A3 | 11/2006 |
| WO | 2007023719 A1 | 3/2007 |
| WO | 2007023764 A1 | 3/2007 |
| WO | 2007024782 A1 | 3/2007 |
| WO | 2007027777 A1 | 3/2007 |
| WO | 2007040280 A1 | 4/2007 |
| WO | 2007048545 | 5/2007 |
| WO | 2007048545 A1 | 5/2007 |
| WO | 2007057407 A2 | 5/2007 |
| WO | 2007068427 A2 | 6/2007 |
| WO | 2007068428 A2 | 6/2007 |
| WO | 2007073856 | 7/2007 |
| WO | 2007073856 A2 | 7/2007 |
| WO | 2007075459 A2 | 7/2007 |
| WO | 2007096058 | 8/2007 |
| WO | 2007096058 A1 | 8/2007 |
| WO | 2007101369 A1 | 9/2007 |
| WO | 2007115643 A1 | 10/2007 |
| WO | 2007115644 A1 | 10/2007 |
| WO | 2007115646 A1 | 10/2007 |
| WO | 2007057407 A3 | 11/2007 |
| WO | 2007073856 A3 | 11/2007 |
| WO | 2007121868 | 11/2007 |
| WO | 2007121868 A1 | 11/2007 |
| WO | 2007140881 | 12/2007 |
| WO | 2007140881 A1 | 12/2007 |
| WO | 2007149134 A1 | 12/2007 |
| WO | 2007075459 A3 | 1/2008 |
| WO | 2008009360 A1 | 1/2008 |
| WO | 2007068427 A3 | 6/2008 |
| WO | 2007068428 A3 | 6/2008 |
| WO | 2008066153 A1 | 6/2008 |
| WO | 2008067873 | 6/2008 |
| WO | 2008067873 A1 | 6/2008 |
| WO | 2008067910 | 6/2008 |
| WO | 2008067910 A1 | 6/2008 |
| WO | 2008067911 | 6/2008 |
| WO | 2008067911 A1 | 6/2008 |
| WO | 2008104503 A1 | 9/2008 |
| WO | 2008131860 A2 | 11/2008 |
| WO | 2008131861 A1 | 11/2008 |
| WO | 2008138551 | 11/2008 |
| WO | 2008138551 A2 | 11/2008 |
| WO | 2008138551 A3 | 2/2009 |
| WO | 2009015801 | 2/2009 |
| WO | 2009015801 A1 | 2/2009 |
| WO | 2009039975 | 4/2009 |

(56) References Cited

FOREIGN PATENT DOCUMENTS

| | | | |
|---|---|---|---|
| WO | 2009039975 | A1 | 4/2009 |
| WO | 2009049851 | | 4/2009 |
| WO | 2009049851 | A1 | 4/2009 |
| WO | 2008067873 | A8 | 6/2009 |
| WO | 2008067910 | A8 | 7/2009 |
| WO | 2009115262 | | 9/2009 |
| WO | 2009115262 | A1 | 9/2009 |
| WO | 2010005692 | A2 | 1/2010 |
| WO | 2010006713 | A2 | 1/2010 |
| WO | 2010005692 | A3 | 4/2010 |
| WO | 2010052161 | | 5/2010 |
| WO | 2010052161 | A2 | 5/2010 |
| WO | 2010005692 | A4 | 6/2010 |
| WO | 2010063378 | | 6/2010 |
| WO | 2010063378 | A1 | 6/2010 |
| WO | 2010063670 | | 6/2010 |
| WO | 2010063670 | A1 | 6/2010 |
| WO | 2010066780 | | 6/2010 |
| WO | 2010066780 | A1 | 6/2010 |
| WO | 2010069502 | A2 | 6/2010 |
| WO | 2010074747 | A1 | 7/2010 |
| WO | 2010074751 | A1 | 7/2010 |
| WO | 2010102758 | | 9/2010 |
| WO | 2010102758 | A2 | 9/2010 |
| WO | 2010052161 | A3 | 12/2010 |
| WO | 2010069502 | A3 | 12/2010 |
| WO | 2010102758 | A3 | 12/2010 |
| WO | 2010006713 | A3 | 4/2011 |
| WO | 2011067135 | | 6/2011 |
| WO | 2011067135 | A1 | 6/2011 |
| WO | 2011067240 | | 6/2011 |
| WO | 2011067240 | A1 | 6/2011 |
| WO | 2010074751 | A8 | 8/2011 |
| WO | 2011098433 | | 8/2011 |
| WO | 2011098440 | | 8/2011 |
| WO | 2011098440 | A2 | 8/2011 |
| WO | 2011098443 | | 8/2011 |
| WO | 2011098443 | A1 | 8/2011 |
| WO | 2010074747 | A8 | 11/2011 |
| WO | 2011098440 | A3 | 7/2012 |
| ZA | 9805601 | A | 1/1999 |

OTHER PUBLICATIONS

International Search Report issued in PCT/EP2012/053289, dated Aug. 16, 2012.

International Search Report issued in PCT/JP2005/004268, dated May 31, 2005.

Ito, et al. "Synthesis and Insecticidal Activity of Novel N-Oxydihydropyrrole Derivatives with a Substitude Spirocyclohexyl Group", Biosci, Biotechnol., Biochem., vol. 67 (6), pp. 1230-1238, 2003.

Braun, et al. "The General Mitochodrial Processing Peptidase from Potato is an Integral Part of Cytochrome c reductase of the respiratory chain", the EMBO Journal vol. 11 No. 9 pp. 3219-3227, 1992.

Baur, et al. "Polydisperse Ethoxylated Fatty Alcohol Surfactants as Accelerators of Cuticular Penetration. 1. Effects of Ethoxy Chain Length and the Size of the Penetrants", Pestic. Sci. 1997, vol. 51, pp. 131-152.

Freyer, et al. "Weed Control Handbook: The VSC of Herbicides in Potato", 5th Ed., Blackwell Scientific Publications, Oxford, 1968, pp. 101-103.

Liebigs, "Cyclisieung von N-Acylalanin- und N-Acylglycinesteru", Chem, 1985, pp. 1095-1098.

Suzuki, et al. "Studies on Antiviral Agents. IV.41. Biological Activity of Tenuazonic Acid Derivatives", Chem. Pharm Bull., vol. 15, pp. 1120-1122, 1967.

Sonnewald, et al. "Transgenic tobacco plants expressing yeast-derived invertase in either the cytosol, vacuole or apoplast: a powerful tool for studying sucrose metabolism and sink/source interactions", The Plant Journal 1991, vol. 1 (1), pp. 95-106.

Christou, "Transformation technology", Trends in Plant Science, vol. 1, 1996, pp. 423-431.

John Wiley and Sons, Inc., New York "5 Surface Active Agents", Weed Control as a Science, 1961 pp. 81-91.

Weed Research, "Glossary of Common Names and Abbreviations of Herbicides", 1986, vol. 26, pp. 441-445.

Wolter, et al. "rbcS genes in Solanum tuberosum: Conservation of transit peptide and exon shuffling during evolution", Proc. Natl. Acad. Sci. USA vol. 85, pp. 846-850, Feb. 1988.

BCS 07-3003-Foreign Countries Gam/Gr Nov. 3, 2008: 3-(2-Alkoxyphenyl)-substituted tetramates.

Internatonal Search Report for PCT/EP2012/053289 Mailed August 16, 2012.

Le A 35 716-Foreign Countries Gam/wa/NT: Fungicidal biphenyl-substituted cyclic ketoenols.

* cited by examiner

2-ACYLOXY-PYRROLIN-4-ONES

CROSS REFERENCE TO RELATED APPLICATIONS

This application is a §371 National Stage Application of PCT/EP2012/053289, filed Feb. 27, 2012, which claims priority to European Application No. 11156415.9, filed Mar. 1, 2011, and U.S. Provisional Application No. 61/447,858, filed Mar. 1, 2011.

BACKGROUND OF THE INVENTION

1. Field of the Invention

The present invention relates to novel 2-acyloxypyrrolin-4-ones, to a plurality of processes for their preparation and to their use as pesticides and/or herbicides. The invention also provides selective herbicidal compositions comprising, firstly, the 2-acyloxypyrrolin-4-ones and, secondly, a crop plant compatibility-improving compound.

2. Description of Related Art

The present invention furthermore relates to the boosting of the action of crop protection compositions comprising, in particular, 2-acyloxypyrrolin-4-ones, through the addition of ammonium salts or phosphonium salts and optionally penetrants, to the corresponding compositions, to processes for producing them and to their application in crop protection as insecticides and/or acaricides and/or nematicides and/or for preventing unwanted plant growth.

3-Acylpyrrolidine-2,4-diones have already been described as having pharmaceutical properties (S. Suzuki et al. Chem. Pharm. Bull. 15 1120 (1967)). Furthermore, N-phenylpyrrolidine-2,4-diones have been synthesized by R. Schmierer and H. Mildenberger (Liebigs Ann. Chem. 1985, 1095). A biological activity of these compounds has not been described.

EP-A-0 262 399 and GB-A-2 266 888 disclose compounds of a similar structure (3-arylpyrrolidine-2,4-diones) of which, however, no herbicidal, insecticidal or acaricidal activity has become known. Unsubstituted bicyclic 3-arylpyrrolidine-2,4-dione derivatives (EP-A-355 599, EP-A-415 211 and JP-A-12-053 670) and substituted monocyclic 3-arylpyrrolidine-2,4-dione derivatives (EP-A-377 893, EP-A-442 077 and WO 10/066,780) are known to have herbicidal, insecticidal or acaricidal activity.

Additionally known are polycyclic 3-arylpyrrolidine-2,4-dione derivatives (EP-A-442 073) and 1H-arylpyrrolidinedione derivatives (EP-A-456 063, EP-A-521 334, EP-A-596 298, EP-A-613 884, EP-A-613 885, WO 95/01 971, WO 95/26 954, WO 95/20 572, EP-A-0 668 267, WO 96/25 395, WO 96/35 664, WO 97/01 535, WO 97/02 243, WO 97/36 868, WO 97/43275, WO 98/05638, WO 98/06721, WO 98/25928, WO 99/24437, WO 99/43649, WO 99/48869, WO 99/55673, WO 01/17972, WO 01/23354, WO 01/74770, WO 03/013249, WO 03/062244, WO 2004/007448, WO 2004/024 688, WO 04/065366, WO 04/080962, WO 04/111042, WO 05/044791, WO 05/044796, WO 05/048710, WO 05/049569, WO 05/066125, WO 05/092897, WO 06/000355, WO 06/029799, WO 06/056281, WO 06/056282, WO 06/089633, WO 07/048,545, DEA 102 00505 9892, WO 07/073,856, WO 07/096,058, WO 07/121,868, WO 07/140, 881, WO 08/067,873, WO 08/067,910, WO 08/067,911, WO 08/138,551, WO 09/015,801, WO 09/039,975, WO 09/049, 851, WO 09/115,262, WO 10/052,161, WO 10/102,758, WO 10/063,378, WO 10/063,670, WO 11/098,440, WO 11/098, 443, WO 11/067,135, WO 11/067,240). Furthermore known are ketal-substituted 1H-arylpyrrolidine-2,4-diones from WO 99/16748 and (spiro)-ketal-substituted N-alkoxyalkoxy-substituted arylpyrrolidinediones from JP-A-14 205 984 and Ito M. et. al., Bioscience, Biotechnology and Biochemistry 67, 1230-1238, (2003). The addition of safeners to ketoenols is also known in principle from WO 03/013249. Moreover, WO 06/024411 discloses herbicidal compositions comprising ketoenols.

Pharmaceutical action has hitherto been disclosed in WO 2011/098433, DE-A-102010008642, DE-A-102010008643 and DE application number 102010008640.

Also known are biphenyl-substituted 1H-pyrrolidinedione derivatives having fungicidal action (WO 03/059065).

However, the activity and the activity spectrum of these compounds are, in particular at low application rates and concentrations, not always entirely satisfactory. Furthermore, the plant compatibility of these compounds with respect to the crop plants is not always sufficient. Moreover, the toxicological properties and/or environmental properties of these compounds are not always entirely satisfactory.

SUMMARY

This invention now provides novel compounds of the formula (I)

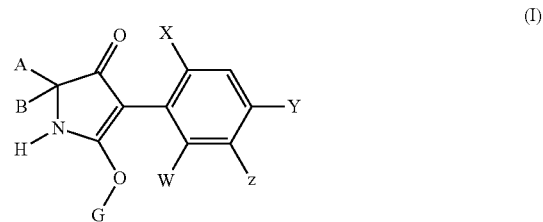

in which

W represents hydrogen, halogen, alkyl, alkenyl, alkynyl, optionally substituted cycloalkyl, alkoxy, alkenyloxy, haloalkyl, haloalkoxy or cyano, X represents halogen, alkyl, alkenyl, alkynyl, optionally substituted cycloalkyl, alkoxy, alkenyloxy, alkylthio, alkylsulfinyl, alkylsulfonyl, haloalkyl, haloalkoxy, haloalkenyloxy, nitro or cyano, Y and Z independently of one another represent hydrogen, alkyl, alkenyl, alkynyl, optionally substituted cycloalkyl, alkoxy, halogen, haloalkyl, haloalkoxy, cyano, nitro or in each case optionally substituted aryl or hetaryl, A represents hydrogen, represents in each case optionally halogen-substituted alkyl, alkenyl, alkoxyalkyl, alkylthioalkyl, saturated or unsaturated, optionally substituted cycloalkyl, in which optionally at least one ring atom is replaced by a heteroatom, or in each case optionally halogen-, alkyl-, haloalkyl-, alkoxy-, haloalkoxy-, cyano- or nitro-substituted aryl, arylalkyl or hetaryl, B represents hydrogen, alkyl or alkoxyalkyl, with the proviso that A and B may each only represent methyl if, in the case of W, X and Y each representing alkyl and Z representing hydrogen, W and X must each represent methyl or W and X must each represent ethyl, or A and B together with the carbon atom to which they are attached represent a saturated or unsaturated, substituted or unsubstituted cycle which optionally contains at least one heteroatom, G represents one of the groups

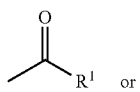 (a)

or

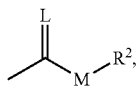 (b)

in which
L represents oxygen or sulfur,
M represents oxygen or sulfur,
R¹ represents in each case optionally halogen- or cyano-substituted alkyl, alkenyl, alkoxyalkyl, alkylthioalkyl or polyalkoxyalkyl or represents in each case optionally halogen-, alkyl- or alkoxy-substituted cycloalkyl or heterocyclyl or represents in each case optionally substituted phenyl, phenylalkyl, hetaryl, phenoxyalkyl or hetaryloxyalkyl,
R² represents in each case optionally halogen- or cyano-substituted alkyl, alkenyl, alkoxyalkyl or polyalkoxyalkyl or represents in each case optionally substituted cycloalkyl, phenyl or benzyl.

DETAILED DESCRIPTION OF A PREFERRED EMBODIMENT

Depending inter alia on the nature of the substituents, the compounds of the formula (I) can be present as optical isomers or isomer mixtures of varying composition which, if desired, can be separated in a customary manner. The present invention provides both the pure isomers and the isomer mixtures, their preparation and use and compositions comprising them. For the sake of simplicity, however, compounds of the formula (I) are always referred to below, although both the pure compounds and also, if appropriate, mixtures having different proportions of isomeric compounds are meant.

Taking into consideration the various meanings (a) and (b) of group G, the following main structures (I-a) to (I-b) result

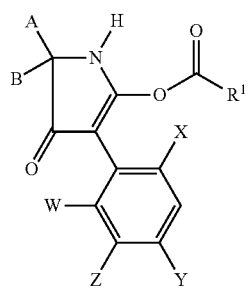 (I-a)

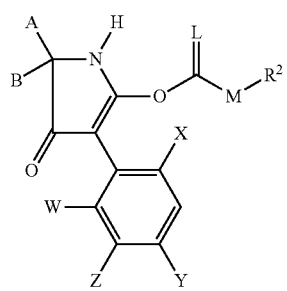 (I-b)

Furthermore, it has been found that the novel compounds of the formula (I) are obtained by the processes described below:
(A) Compounds of the formula (I-a) shown above in which R¹, A, B, W, X, Y and Z have the meanings given above are obtained when compounds of the formula (II) in which A, B, W, X, Y and Z have the meanings given above

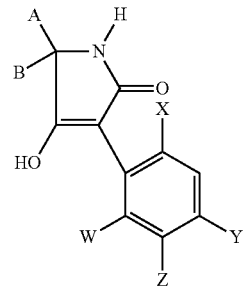 (II)

in which
A, B, W, X, Y and Z have the meanings given above,
α) are reacted with compounds of the formula (III)

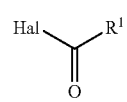 (III)

in which
R¹ has the meaning given above and
Hal represents halogen (in particular chlorine or bromine)
or
β) with carboxylic anhydrides of the formula (IV)

R¹—CO—O—CO—R¹ (IV)

in which
R¹ has the meaning given above and
if appropriate in the presence of a diluent and if appropriate in the presence of an acid binder.
(B) Compounds of the formula (I-b) shown above in which R², A, B, M, W, X, Y and Z have the meanings given above and L represents oxygen are obtained when compounds of the formula (II) shown above in which A, B, W, X, Y and Z have the meanings given above are reacted with chloroformic esters or chloroformic thioesters of the formula (V)

R²-M-CO—Cl (V)

in which
R² and M have the meanings given above,
if appropriate in the presence of a diluent and if appropriate in the presence of an acid binder.

Furthermore it has been found that the novel compounds of the formula (I) have good activity as pesticides, preferably as insecticides and/or acaricides and/or herbicides, are additionally frequently highly compatible with plants, especially crop plants, and/or have favorable toxicological and/or environmentally relevant properties.

Surprisingly, it has now also been found that certain substituted cyclic ketoenols, when used together with the crop plant compatibility-improving compounds (safeners/antidotes) described below, very efficiently prevent damage to the crop plants and can be used in a particularly advantageous manner as broad-spectrum combination preparations for the selective control of unwanted plants in crops of useful plants, such as, for example, in cereals, but also in corn, oilseed rape, soya and rice.

The invention also provides selective herbicidal compositions comprising an effective amount of an active compound combination comprising, as components, a') at least one compound of the formula (I) in which A, B, G, W, X, Y and Z have the meaning given above
and
(b') at least one crop plant compatibility-improving compound (safener).

The safeners are preferably selected from the group consisting of:

S1) compounds of the formula (S1)

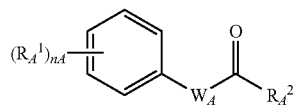

(S1)

where the symbols and indices have the following meanings:

$n_A$ is a natural number from 0 to 5, preferably 0 to 3;

$R_A^1$ is halogen, $(C_1-C_4)$-alkyl, $(C_1-C_4)$-alkoxy, nitro or $(C_1-C_4)$-haloalkyl;

$W_A$ is an unsubstituted or substituted divalent heterocyclic radical from the group of the partially unsaturated or aromatic five-membered heterocycles having 1 to 3 ring heteroatoms of the N and O group, where at least one nitrogen atom and at most one oxygen atom is present in the ring, preferably a radical from the group of $(W_A^1)$ to $(W_A^4)$,

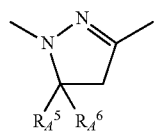

$(W_A^1)$

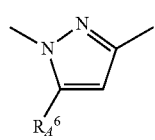

$(W_A^2)$

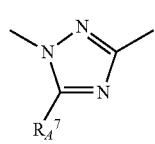

$(W_A^3)$

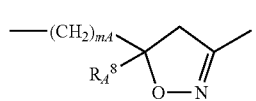

$(W_A^4)$ $m_A$ is 0 or 1;

$R_A^2$ is $OR_A^3$, $SR_A^3$ or $NR_A^3R_A^4$ or a saturated or unsaturated 3- to 7-membered heterocycle having at least one nitrogen atom and up to 3 heteroatoms, preferably from the group of O and S, which is joined to the carbonyl group in (S1) via the nitrogen atom and is unsubstituted or substituted by radicals from the group of $(C_1-C_4)$ alkyl, $(C_1-C_4)$alkoxy or optionally substituted phenyl, preferably a radical of the formula $OR_A^3$, $NHR_A^4$ or $N(CH_3)_2$, especially of the formula $OR_A^3$;

$R_A^3$ is hydrogen or an unsubstituted or substituted aliphatic hydrocarbon radical preferably having a total of 1 to 18 carbon atoms;

$R_A^4$ is hydrogen, $(C_1-C_6)$-alkyl, $(C_1-C_6)$-alkoxy or substituted or unsubstituted phenyl;

$R_A^5$ is H, $(C_1-C_8)$-alkyl, $(C_1-C_8)$-haloalkyl, $(C_1-C_4)$-alkoxy-$(C_1-C_8)$-alkyl, cyano or $COOR_A^9$, where $R_A^9$ is hydrogen, $(C_1-C_8)$-alkyl, $(C_1-C_8)$-haloalkyl, $(C_1-C_4)$-alkoxy-$(C_1-C_4)$-alkyl, $(C_1-C_6)$-hydroxyalkyl, $(C_3-C_{12})$-cycloalkyl or tri-$(C_1-C_4)$-alkyl-silyl;

$R_A^6$, $R_A^7$, $R_A^8$ are the identical or different and are hydrogen, $(C_1-C_8)$-alkyl, $(C_1-C_8)$-haloalkyl, $(C_3-C_{12})$-cycloalkyl or substituted or unsubstituted phenyl;

preferably:

a) compounds of the dichlorophenylpyrazoline-3-carboxylic acid type (S1$^a$), preferably compounds such as 1-(2,4-dichlorophenyl)-5-(ethoxycarbonyl)-5-methyl-2-pyrazoline-3-carboxylic acid, ethyl 1-(2,4-dichlorophenyl)-5-(ethoxycarbonyl)-5-methyl-2-pyrazoline-3-carboxylate (S1-1) ("mefenpyr-diethyl"), and related compounds as described in WO-A-91/07874;

b) derivatives of dichlorophenylpyrazolecarboxylic acid (S1$^b$), preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4) and related compounds as described in EP-A-333 131 and EP-A-269 806;

c) derivatives of 1,5-diphenylpyrazole-3-carboxylic acid (S1$^c$), preferably compounds such as ethyl 1-(2,4-dichlorophenyl)-5-phenylpyrazole-3-carboxylate (S1-5), ethyl 1-(2-chlorophenyl)-5-phenylpyrazole-3-carboxylate (S1-6) and related compounds as described in EP-A-268 554, for example;

d) compounds of the triazolecarboxylic acid type (S1$^d$), preferably compounds such as fenchlorazole(-ethyl ester), i.e. ethyl 1-(2,4-dichlorophenyl)-5-trichloromethyl-(1H)-1,2,4-triazole-3-carboxylate (51-7), and related compounds as described in EP-A-174 562 and EP-A-346 620;

e) compounds of the 5-benzyl- or 5-phenyl-2-isoxazoline-3-carboxylic acid or of the 5,5-diphenyl-2-isoxazoline-3-carboxylic acid type (S1$^e$), preferably compounds such as ethyl 5-(2,4-dichlorobenzyl)-2-isoxazoline-3-carboxylate (S1-8) or ethyl 5-phenyl-2-isoxazoline-3-carboxylate (S1-9) and related compounds as described in WO-A-91/08202, or 5,5-diphenyl-2-isoxazoline-3-carboxylic acid (S1-10) or ethyl 5,5-diphenyl-2-isoxazoline-3-carboxylate (S1-11) ("isoxadifen-ethyl") or n-propyl 5,5-diphenyl-2-isoxazoline-3-carboxylate (S1-12) or ethyl 5-(4-fluorophenyl)-5-phenyl-2-isoxazoline-3-carboxylate (S1-13), as described in patent application WO-A-95/07897.

S2) Quinoline derivatives of the formula (S2)

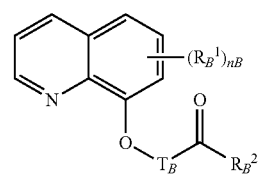

(S2)

where the symbols and indices have the following meanings:
$R_B^1$ is halogen, $(C_1-C_4)$-alkyl, $(C_1-C_4)$-alkoxy, nitro or $(C_1-C_4)$-haloalkyl;
$n_B$ is a natural number from 0 to 5, preferably 0 to 3;
$R_B^2$ is $OR_B^3$, $SR_B^3$ or $NR_B^3 R_B^4$ or a saturated or unsaturated 3- to 7-membered heterocycle having at least one nitrogen atom and up to 3 heteroatoms, preferably from the group of O and S, which is joined to the carbonyl group in (S2) via the nitrogen atom and is unsubstituted or substituted by radicals from the group of $(C_1-C_4)$-alkyl, $(C_1-C_4)$-alkoxy or optionally substituted phenyl, preferably a radical of the formula $OR_B^3$, $NHR_B^4$ or $N(CH_3)_2$, especially of the formula $OR_B^3$;
$R_B^3$ is hydrogen or an unsubstituted or substituted aliphatic hydrocarbyl radical preferably having a total of 1 to 18 carbon atoms;
$R_B^4$ is hydrogen, $(C_1-C_6)$-alkyl, $(C_1-C_6)$-alkoxy or substituted or unsubstituted phenyl;
$T_B$ is a ($C_1$ or $C_2$)-alkanediyl chain which is unsubstituted or substituted by one or two $(C_1-C_4)$-alkyl radicals or by [$(C_1-C_3)$-alkoxy]-carbonyl;
preferably:
a) compounds of the 8-quinolinoxyacetic acid type (S2$^a$), preferably 1-methylhexyl (5-chloro-8-quinolinoxy)acetate ("cloquintocet-mexyl") (S2-1), 1,3-dimethylbut-1-yl (5-chloro-8-quinolinoxy)acetate (S2-2), 4-allyloxybutyl (5-chloro-8-quinolinoxy)acetate (S2-3), 1-allyloxyprop-2-yl (5-chloro-8-quinolinoxy)acetate (S2-4), ethyl (5-chloro-8-quinolinoxy)acetate (S2-5), methyl (5-chloro-8-quinolinoxy)acetate (S2-6), allyl (5-chloro-8-quinolinoxy)acetate (S2-7), 2-(2-propylideneiminoxy)-1-ethyl (5-chloro-8-quinolinoxy)acetate (S2-8), 2-oxoprop-1-yl (5-chloro-8-quinolinoxy) acetate (S2-9) and related compounds, as described in EP-A-86 750, EP-A-94 349 and EP-A-191 736 or EP-A-0 492 366, and also (5-chloro-8-quinolinoxy)acetic acid (S2-10), the hydrates and salts thereof, for example the lithium, sodium, potassium, calcium, magnesium, aluminum, iron, ammonium, quaternary ammonium, sulfonium or phosphonium salts thereof, as described in WO-A-2002/34048;
b) compounds of the (5-chloro-8-quinolinoxy)malonic acid type (S2$^b$), preferably compounds such as diethyl (5-chloro-8-quinolinoxy)malonate, diallyl (5-chloro-8-quinolinoxy)malonate, methyl ethyl (5-chloro-8-quinolinoxy)malonate and related compounds, as described in EP-A-0 582 198.
S3) Compounds of the formula (S3)

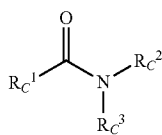

(S3)

where the symbols and indices have the following meanings:
$R_C^1$ is $(C_1-C_4)$-alkyl, $(C_1-C_4)$-haloalkyl, $(C_2-C_4)$-alkenyl, $(C_2-C_4)$-haloalkenyl, $(C_3-C_7)$-cycloalkyl, preferably dichloromethyl;
$R_C^2$, $R_C^3$ are identical or different and are hydrogen, $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_1-C_4)$-alkylcarbamoyl-$(C_1-C_4)$-alkyl, $(C_2-C_4)$-alkenylcarbamoyl-$(C_1-C_4)$-alkyl, $(C_1-C_4)$-alkoxy-$(C_1-C_4)$-alkyl, dioxolanyl-$(C_1-C_4)$-alkyl, thiazolyl, furyl, furylalkyl, thienyl, piperidyl, substituted or unsubstituted phenyl, or $R_C^2$ and $R_C^3$ together form a substituted or unsubstituted heterocyclic ring, preferably an oxazolidine, thiazolidine, piperidine, morpholine, hexahydropyrimidine or benzoxazine ring;
preferably:
active compounds of the dichloroacetamide type, which are frequently used as pre-emergence safeners (soil-acting safeners), for example "dichlormid" (N,N-diallyl-2,2-dichloroacetamide) (S3-1), "R-29148" (3-dichloroacetyl-2,2,5-trimethyl-1,3-oxazolidine) from Stauffer (S3-2), "R-28725" (3-dichloroacetyl-2,2-dimethyl-1,3-oxazolidine) from Stauffer (S3-3), "benoxacor" (4-dichloroacetyl-3,4-dihydro-3-methyl-2H-1,4-benzoxazine) (S3-4), "PPG-1292" (N-allyl-N-[(1,3-dioxolan-2-yl)methyl]dichloroacetamide) from PPG Industries (S3-5), "DKA-24" (N-allyl-N-[(allylaminocarbonyl)methyl]dichloroacetamide) from Sagro-Chem (S3-6), "AD-67" or "MON 4660" (3-dichloroacetyl-1-oxa-3-azaspiro[4,5]decane) from Nitrokemia or Monsanto (S3-7), "TI-35" (1-dichloroacetylazepane) from TRI-Chemical RT (S3-8), "diclonon" (dicyclonone) or "BAS145138" or "LAB145138" (S3-9) (3-dichloroacetyl-2,2,5-trimethyl-1,3-diazabicyclo[4.3.0]nonane) from BASF, "furilazole" or "MON 13900" ((RS)-3-dichloroacetyl-5-(2-furyl)-2,2-dimethyloxazolidine) (S3-10); and the (R) isomer thereof (S3-11).
S4) N-Acylsulfonamides of the formula (S4) and salts thereof

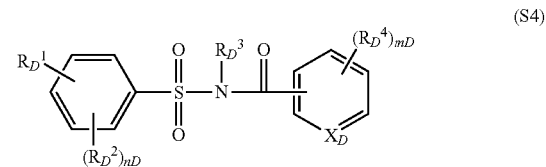

(S4)

where the symbols and indices have the following meanings:
$X_D$ is CH or N;
$R_D^1$ is $CO-NR_D^5 R_D^6$ or $NHCO-R_D^7$;
$R_D^2$ is halogen, $(C_1-C_4)$-haloalkyl, $(C_1-C_4)$-haloalkoxy, nitro, $(C_1-C_4)$-alkyl, $(C_1-C_4)$-alkoxy, $(C_1-C_4)$-alkylsulfonyl, $(C_1-C_4)$-alkoxycarbonyl or $(C_1-C_4)$-alkylcarbonyl;
$R_D^3$ is hydrogen, $(C_1-C_4)$-alkyl, $(C_2-C_4)$-alkenyl or $(C_2-C_4)$-alkynyl;
$R_D^4$ is halogen, nitro, $(C_1-C_4)$-alkyl, $(C_1-C_4)$-haloalkyl, $(C_1-C_4)$-haloalkoxy, $(C_3-C_6)$-cycloalkyl, phenyl, $(C_1-C_4)$-alkoxy, cyano, $(C_1-C_4)$-alkylthio, $(C_1-C_4)$-alkylsulfinyl, $(C_1-C_4)$-alkylsulfonyl, $(C_1-C_4)$-alkoxycarbonyl or $(C_1-C_4)$-alkylcarbonyl;
$R_D^5$ is hydrogen, $(C_1-C_6)$-alkyl, $(C_3-C_6)$-cycloalkyl, $(C_2-C_6)$-alkenyl, $(C_2-C_6)$-alkynyl, $(C_5-C_6)$-cycloalkenyl, phenyl or 3- to 6-membered heterocyclyl containing $v_D$ heteroatoms from the group of nitrogen, oxygen and sulfur, where the seven latter radicals are each substituted by $v_D$ substituents from the group of halogen, $(C_1-C_6)$-alkoxy, $(C_1-C_6)$-haloalkoxy, $(C_1-C_2)$-alkylsulfinyl, $(C_1-C_2)$-alkylsulfonyl, $(C_3-C_6)$-cycloalkyl, $(C_1-C_4)$-alkoxycarbonyl, $(C_1-C_4)$-alkylcarbonyl and phenyl, and in the case of cyclic radicals also $(C_1-C_4)$-alkyl and $(C_1-C_4)$-haloalkyl;

$R_D^6$ is hydrogen, $(C_1-C_6)$-alkyl, $(C_2-C_6)$-alkenyl or $(C_2-C_6)$-alkynyl, where the three latter radicals are substituted by $v_D$ radicals from the group of halogen, hydroxyl, $(C_1-C_4)$-alkyl, $(C_1-C_4)$-alkoxy and $(C_1-C_4)$-alkylthio, or $R_D^5$ and $R_D^6$ together with the nitrogen atom which bears them form a pyrrolidinyl or piperidinyl radical;

$R_D^7$ is hydrogen, $(C_1-C_4)$-alkylamino, di-$(C_1-C_4)$-alkylamino, $(C_1-C_6)$-alkyl, $(C_3-C_6)$-cycloalkyl, where the 2 latter radicals are substituted by $v_D$ substituents from the group of halogen, $(C_1-C_4)$-alkoxy, $(C_1-C_6)$-haloalkoxy and $(C_1-C_4)$-alkylthio, and in the case of cyclic radicals also $(C_1-C_4)$-alkyl and $(C_1-C_4)$-haloalkyl;

$n_D$ is 0, 1 or 2;
$m_D$ is 1 or 2;
$v_D$ is 0, 1, 2 or 3;

among these, preference is given to compounds of the N-acylsulfonamide type, for example of the formula (S4$^a$) below, which are known, for example, from WO-A-97/45016

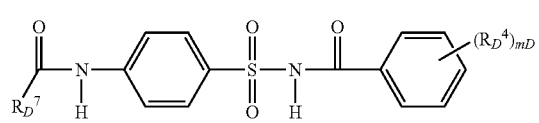

(S4a)

in which $R_D^7$ is $(C_1-C_6)$-alkyl, $(C_3-C_6)$-cycloalkyl, where the 2 latter radicals are substituted by $v_D$ substituents from the group of halogen, $(C_1-C_4)$-alkoxy, $(C_1-C_6)$-haloalkoxy and $(C_1-C_4)$-alkylthio, and in the case of cyclic radicals also $(C_1-C_4)$-alkyl and $(C_1-C_4)$-haloalkyl;

$R_D^4$ is halogen, $(C_1-C_4)$-alkyl, $(C_1-C_4)$-alkoxy, $CF_3$,
$m_D$ is 1 or 2;
$v_D$ is 0, 1, 2 or 3;

and
acylsulfamoylbenzamides, for example of the formula (S4$^b$) below, which are known, for example, from WO-A-99/16744,

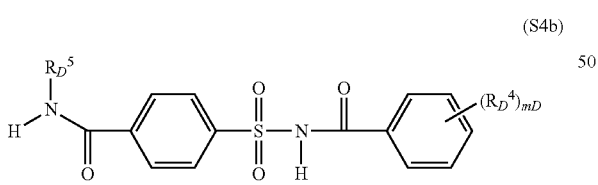

(S4b)

for example those in which
$R_D^5$=cyclopropyl and $(R_D^4)$=2-OMe ("cyprosulfamide", S4-1),
$R_D^5$=cyclopropyl and $(R_D^4)$=5-$C_{1-2}$-OMe (S4-2),
$R_D^5$=ethyl and $(R_D^4)$=2-OMe (S4-3),
$R_D^5$=isopropyl and $(R_D^4)$=5-$C_{1-2}$-OMe (S4-4) and
$R_D^5$=isopropyl and $(R_D^4)$=2-OMe (S4-5),
and
compounds of the N-acylsulfamoylphenylurea type, of the formula (S4$^c$), which are known, for example, from EP-A-365484,

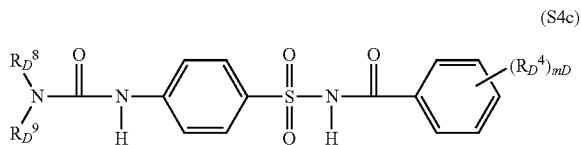

(S4c)

in which
$R_D^8$ and $R_D^9$ are each independently of one another hydrogen, $(C_1-C_8)$-alkyl, $(C_3-C_8)$-cycloalkyl, $(C_3-C_6)$-alkenyl, $(C_3-C_6)$-alkynyl,
$R_D^4$ is halogen, $(C_1-C_4)$-alkyl, $(C_1-C_4)$-alkoxy, $CF_3$
$m_D$ is 1 or 2;
for example
1-[4-(N-2-methoxybenzoylsulfamoyl)phenyl]-3-methylurea,
1-[4-(N-2-methoxybenzoylsulfamoyl)phenyl]-3,3-dimethylurea,
1-[4-(N-4,5-dimethylbenzoylsulfamoyl)phenyl]-3-methylurea.

S5) Active compounds from the class of the hydroxyaromatics and aromatic-aliphatic carboxylic acid derivatives (S5), for example ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicyclic acid, 2-hydroxycinnamic acid, 1,2-dihydro-2-oxo-6-trifluoromethylpyridine-3-carboxamide, 2,4-dichlorocinnamic acid, as described in WO-A-2004/084631, WO-A-2005/015994, WO-A-2005/016001.

S6) Active compounds from the class of the 1,2-dihydroquinoxalin-2-ones (S6), for example 1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-[2-(diethylamino)ethyl]-6,7-dimethyl-3-thiophen-2-ylquinoxalin-2(1H)-one, 1-(2-methylsulfonylaminoethyl)-3-(2-thienyl)-1,2-dihydroquinoxalin-2-one, as described in WO-A-2005/112630.

S7) Compounds of the formula (S7), as described in WO-A-1998/38856,

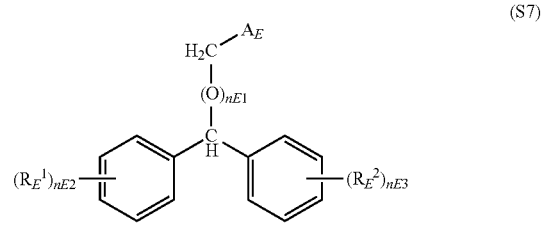

(S7)

where the symbols and indices have the following meanings:

$R_E^1$, $R_E^2$ are each independently of one another halogen, $(C_1-C_4)$-alkyl, $(C_1-C_4)$-alkoxy, $(C_1-C_4)$-haloalkyl, $(C_1-C_4)$-alkylamino, di-$(C_1-C_4)$-alkylamino, nitro;

$A_E$ is $COOR_E^3$ or $COSR_E^4$ $R_E^3$, $R_E^4$ are each independently of one another hydrogen, $(C_1-C_4)$-alkyl, $(C_2-C_6)$-alkenyl, $(C_2-C_4)$-alkynyl, cyanoalkyl, $(C_1-C_4)$-haloalkyl, phenyl, nitrophenyl, benzyl, halobenzyl, pyridinylalkyl and alkylammonium;

$n_E^1$ is 0 or 1
$n_E^2$, $n_E^3$ are each independently of one another 0, 1 or 2, preferably:
diphenylmethoxyacetic acid, ethyl diphenylmethoxyacetate, methyl diphenylmethoxyacetate (CAS reg. no. 41858-19-9) (S7-1).

S8) Compounds of the formula (S8), as described in WO-A-98/27049,

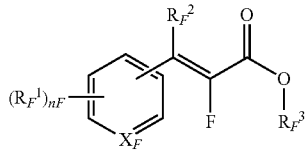

(S8)

in which
$X_F$ is CH or N,
$n_F$ in the case that $X_F$=N is an integer from 0 to 4 and in the case that $X_F$=CH is an integer from 0 to 5,
$R_F^1$ is halogen, $(C_1-C_4)$-alkyl, $(C_1-C_4)$-haloalkyl, $(C_1-C_4)$-alkoxy, $(C_1-C_4)$-haloalkoxy, nitro, $(C_1-C_4)$-alkylthio, $(C_1-C_4)$-alkylsulfonyl, $(C_1-C_4)$-alkoxycarbonyl, optionally substituted phenyl, optionally substituted phenoxy,
$R_F^2$ is hydrogen or $(C_1-C_4)$-alkyl
$R_F^3$ is hydrogen, $(C_1-C_8)$-alkyl, $(C_2-C_4)$-alkenyl, $(C_2-C_4)$-alkynyl, or aryl, where each of the aforementioned carbon-containing radicals is unsubstituted or substituted by one or more, preferably up to three identical or different radicals from the group consisting of halogen and alkoxy, or salts thereof.

preferably compounds in which
$X_F$ is CH,
$n_F$ is an integer from 0 to 2,
$R_F^1$ is halogen, $(C_1-C_4)$-alkyl, $(C_1-C_4)$-haloalkyl, $(C_1-C_4)$-alkoxy, $(C_1-C_4)$-haloalkoxy,
$R_F^2$ is hydrogen or $(C_1-C_4)$-alkyl,
$R_F^3$ is hydrogen, $(C_1-C_8)$-alkyl, $(C_2-C_4)$-alkenyl, $(C_2-C_4)$-alkynyl, or aryl, where each of the aforementioned carbon-containing radicals is unsubstituted or substituted by one or more, preferably up to three identical or different radicals from the group consisting of halogen and alkoxy, or salts thereof.

S9) Active compounds from the class of the 3-(5-tetrazolylcarbonyl)-2-quinolones (S9), e.g. 1,2-dihydro-4-hydroxy-1-ethyl-3-(5-tetrazolylcarbonyl)-2-quinolone (CAS reg. no. 219479-18-2), 1,2-dihydro-4-hydroxy-1-methyl-3-(5-tetrazolylcarbonyl)-2-quinolone (CAS reg. no. 95855-00-8), as described in WO-A-1999/000020.

S10) Compounds of the formulae (S10$^a$) or (S10$^b$) as described in WO-A-2007/023719 and WO-A-2007/023764,

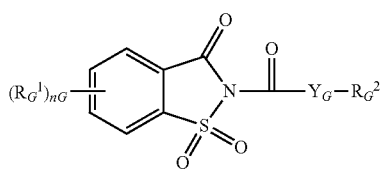

(S10a)

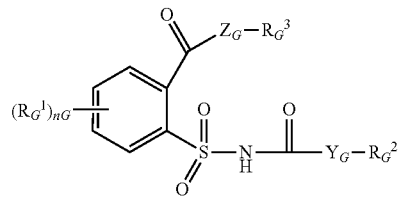

(S10b)

in which
$R_G^1$ is halogen, $(C_1-C_4)$-alkyl, methoxy, nitro, cyano, $CF_3$, $OCF_3$,
$Y_G, Z_G$ are each independently of one another O or S,
$n_G$ is an integer from 0 to 4,
$R_G^2$ is $(C_1-C_{16})$-alkyl, $(C_2-C_6)$-alkenyl, $(C_3-C_6)$-cycloalkyl, aryl; benzyl, halobenzyl,
$R_G^3$ is hydrogen or $(C_1-C_6)$-alkyl.

S11) Active compounds of the type of the oxyimino compounds (S11), which are known as seed dressings, such as, for example, "oxabetrinil" ((Z)-1,3-dioxolan-yl-methoxyimino(phenyl)acetonitrile) (S11-1), which is known as seed dressing safener for millet against metolachlor damage,
"fluxofenim" (1-(4-chlorophenyl)-2,2,2-trifluoro-1-ethanone-O-(1,3-dioxolan-2-ylmethyl)oxime) (S11-2), which is known as seed dressing safener for millet against metolachlor damage, and
"cyometrinil" or "CGA-43089" ((Z)-cyanomethoxyimino(phenyl)acetonitrile) (S11-3), which is known as seed dressing safener for millet against metolachlor damage.

S12) Active compounds from the class of the isothiochromanones (S12), for example methyl [(3-oxo-1H-2-benzothiopyran-4(3H)-ylidene)methoxy]acetate (CAS reg. no. 205121-04-6) (S12-1) and related compounds from WO-A-1998/13361.

S13) One or more compounds from group (S13):
"naphthalic anhydrid" (1,8-naphthalenedicarboxylic anhydride) (S13-1), which is known as seed dressing safener for corn against thiocarbamate herbicide damage,
"fenclorim" (4,6-dichloro-2-phenylpyrimidine) (S13-2), which is known as safener for pretilachlor in sown rice,
"flurazole" (benzyl 2-chloro-4-trifluoromethyl-1,3-thiazole-5-carboxylate) (S13-3), which is known as seed dressing safener for millet against alachlor and metolachlor damage,
"CL 304415" (CAS reg. no. 31541-57-8) (4-carboxy-3,4-dihydro-2H-1-benzopyran-4-acetic acid) (S13-4) from American Cyanamid, which is known as a safener for corn against damage by imidazolinones,
"MG 191" (CAS reg. no. 96420-72-3) (2-dichloromethyl-2-methyl-1,3-dioxolane) (S13-5) from Nitrokemia, which is known as a safener for corn,
"MG-838" (CAS reg. no. 133993-74-5) (2-propenyl 1-oxa-4-azaspiro[4.5]decane-4-carbodithioate) (S13-6) from Nitrokemia,
"disulfoton" (0,0-diethyl S-2-ethylthioethyl phosphorodithioate) (S13-7),
"dietholate" (0,0-diethyl O-phenyl phosphorothioate) (S13-8),
"mephenate" (4-chlorophenyl methylcarbamate) (S13-9).

S14) Active compounds which, in addition to herbicidal action against harmful plants, also have safener action on crop plants such as rice, for example
"dimepiperate" or "MY-93" (S-1-methyl-1-phenylethylpiperidine-1-carbothioate), which is known as a safener for rice against damage by the herbicide molinate,
"daimuron" or "SK 23" (1-(1-methyl-1-phenylethyl)-3-p-tolylurea), which is known as safener for rice against imazosulfuron herbicide damage,
"cumyluron"="JC-940" (3-(2-chlorophenylmethyl)-1-(1-methyl-1-phenylethyl)urea, see JP-A-60087254), which is known as safener for rice against damage by some herbicides,
"methoxyphenone" or "NK 049" (3,3'-dimethyl-4-methoxybenzophenone), which is known as safener for rice against damage by some herbicides,
"CSB" (1-bromo-4-(chloromethylsulfonyl)benzene) from Kumiai, (CAS reg. no. 54091-06-4), which is known as a safener against damage by some herbicides in rice.

S15) Compounds of the formula (S15) or tautomers thereof

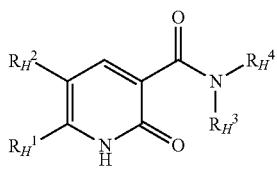

(S15)

as described in WO-A-2008/131861 and WO-A-2008/131860
in which
$R_H^1$ is a $(C_1-C_6)$-haloalkyl radical and
$R_H^2$ is hydrogen or halogen and
$R_H^3$, $R_H^4$ are each independently of one another hydrogen, $(C_1-C_{16})$-alkyl, $(C_2-C_{16})$-alkenyl or $(C_2-C_{16})$-alkynyl, where each of the latter 3 radicals is unsubstituted or substituted by one or more radicals from the group of halogen, hydroxyl, cyano, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]amino, [$(C_1-C_4)$-alkoxy]carbonyl, [$(C_1-C_4)$-haloalkoxy]carbonyl, $(C_3-C_6)$-cycloalkyl which is unsubstituted or substituted, phenyl which is unsubstituted or substituted, and heterocyclyl which is unsubstituted or substituted,
or $(C_3-C_6)$-cycloalkyl, $(C_4-C_6)$-cycloalkenyl, $(C_3-C_6)$-cycloalkyl which is fused on one side of the ring to a 4- to 6-membered saturated or unsaturated carbocyclic ring, or $(C_4-C_6)$-cycloalkenyl which is fused on one side of the ring to a 4- to 6-membered saturated or unsaturated carbocyclic ring,
where each of the latter 4 radicals is unsubstituted or substituted by one or more radicals from the group of halogen, hydroxyl, cyano, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]amino, [$(C_1-C_4)$-alkoxy]carbonyl, [$(C_1-C_4)$-haloalkoxy]carbonyl, $(C_3-C_6)$-cycloalkyl which is unsubstituted or substituted, phenyl which is unsubstituted or substituted, and heterocyclyl which is unsubstituted or substituted,
or
$R_H^3$ is $(C_1-C_4)$-alkoxy, $(C_2-C_4)$-alkenyloxy, $(C_2-C_6)$-alkynyloxy or $(C_2-C_4)$-haloalkoxy and
$R_H^4$ is hydrogen or $(C_1-C_4)$-alkyl or
$R_H^3$ and $R_H^4$ together with the directly bonded nitrogen atom are a four- to eight-membered heterocyclic ring which, as well as the nitrogen atom, may also contain further ring heteroatoms, preferably up to two further ring heteroatoms from the group of N, O and S, and which is unsubstituted or substituted by one or more radicals from the group of halogen, cyano, nitro, $(C_1-C_4)$-alkyl, $(C_1-C_4)$-haloalkyl, $(C_1-C_4)$-alkoxy, $(C_1-C_4)$-haloalkoxy and $(C_1-C_4)$-alkylthio.

S16) Active compounds which are used primarily as herbicides but also have safener action on crop plants, for example
(2,4-dichlorophenoxy)acetic acid (2,4-D),
(4-chlorophenoxy)acetic acid,
(R,S)-2-(4-chloro-o-tolyloxy)propionic acid (mecoprop),
4-(2,4-dichlorophenoxy)butyric acid (2,4-DB),
(4-chloro-o-tolyloxy)acetic acid (MCPA),
4-(4-chloro-o-tolyloxy)butyric acid,
4-(4-chlorophenoxy)butyric acid,
3,6-dichloro-2-methoxybenzoic acid (dicamba),
1-(ethoxycarbonyl)ethyl 3,6-dichloro-2-methoxybenzoate (lactidichlor-ethyl).

Most preferred as crop plant compatibility-improving compound [component (b')] are cloquintocet-mexyl, fenchlorazole-ethyl, isoxadifen-ethyl, mefenpyr-diethyl, fenclorim, cumyluron, S4-1 and S4-5, and particular emphasis is given to cloquintocet-mexyl and mefenpyr-diethyl.

Surprisingly, it has now been found that the active compound combinations defined above of compounds of the general formula (I) and safeners (antidotes) from the group (b') set out above combine very good useful plant compatibility with a particularly high herbicidal activity and can be used in various crops, in particular in cereals (especially wheat), but also in soya, potatoes, corn and rice, for the selective control of weeds.

In this context it is to be considered surprising that, from a multiplicity of known safeners or antidotes capable of antagonizing the damaging effect of a herbicide on the crop plants, it is specifically the compounds of group (b') set out above which are suitable for compensating—almost completely—the damaging effect of compounds of the formula (I) on the crop plants, without at the same time having any critical adverse effect on the herbicidal activity against the weeds.

Emphasis may be given here to the particularly advantageous effect of the particularly preferred and most preferred combination partners from group (b'), in particular with regard to the gentle treatment of cereal plants, such as wheat, barley and rye, for example, but also corn and rice, as crop plants.

The formula (I) provides a general definition of the compounds according to the invention. Preferred substituents or ranges of the radicals given under the formulae shown above and below are illustrated below:

W preferably represents hydrogen, halogen, $C_1-C_6$-alkyl, $C_2-C_6$-alkenyl, $C_2-C_6$-alkynyl, $C_3-C_6$-cycloalkyl which is optionally mono- to disubstituted by $C_1-C_2$-alkyl, $C_1-C_2$-alkoxy, fluorine, chlorine, trifluoromethyl or $C_3-C_6$-cycloalkyl, $C_1-C_6$-alkoxy, $C_1-C_4$-haloalkyl, $C_1-C_4$-haloalkoxy or cyano, X preferably represents halogen, $C_1-C_6$-alkyl, $C_2-C_6$-alkenyl, $C_2-C_6$-alkynyl, $C_3-C_6$-cycloalkyl which is optionally mono- to disubstituted by $C_1-C_2$-alkyl, $C_1-C_2$-alkoxy, fluorine, chlorine, trifluoromethyl or $C_3-C_6$-cycloalkyl, $C_1-C_6$-haloalkyl, $C_1-C_6$-alkoxy, $C_3-C_6$-alkenyloxy, $C_1$-$C_6$-alkylthio, $C_1$-$C_6$-alkylsulfinyl, $C_1$-$C_6$-alkylsulfonyl, $C_1$-$C_6$-haloalkoxy, $C_3$-$C_6$-haloalkenyloxy, nitro or cyano, Y and Z independently of one another preferably represent hydrogen, halogen, $C_1$-$C_6$-alkyl, $C_2$-$C_6$-alkenyl, $C_2$-$C_6$-alkynyl, $C_3$-$C_6$-cycloalkyl which is optionally mono- to disubstituted by $C_1$-$C_2$-alkyl, $C_1$-$C_2$-alkoxy, fluorine, chlorine, trifluoromethyl or $C_3$-$C_6$-cycloalkyl, $C_1$-$C_6$-alkoxy, $C_1$-$C_6$-haloalkyl, $C_1$-$C_6$-haloalkoxy, cyano, $C_2$-$C_6$-alkenyl, $C_2$-$C_6$-alkynyl or represent one of the (Het)-aryl radicals

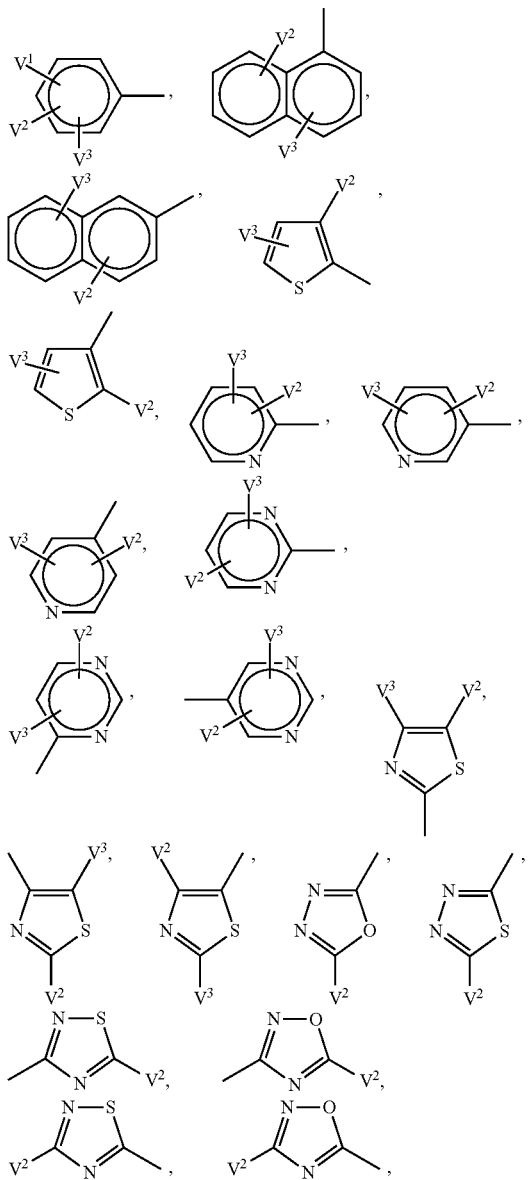

where in the case of (het)aryl only one of the radicals Y or Z may represent (het)aryl, $V^1$ preferably represents hydrogen, halogen, $C_1$-$C_{12}$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_1$-$C_4$-haloalkyl, $C_1$-$C_4$-haloalkoxy, nitro, cyano or represents phenyl, phenoxy, phenoxy-$C_1$-$C_4$-alkyl, phenyl-$C_1$-$C_4$-alkoxy, phenylthio-$C_1$-$C_4$-alkyl or phenyl-$C_1$-$C_4$-alkylthio, each of which is optionally mono- or polysubstituted by halogen, $C_1$-$C_6$-alkyl, $C_1$-$C_6$-alkoxy, $C_1$-$C_4$-haloalkyl, $C_1$-$C_4$-haloalkoxy, nitro or cyano, $V^2$ and $V^3$ independently of one another preferably represent hydrogen, halogen, $C_1$-$C_6$-alkyl, $C_1$-$C_6$-alkoxy, $C_1$-$C_4$-haloalkyl or $C_1$-$C_4$-haloalkoxy, A preferably represents hydrogen or in each optionally halogen-substituted $C_1$-$C_{12}$-alkyl, $C_3$-$C_8$-alkenyl, $C_1$-$C_{10}$-alkoxy-$C_1$-$C_8$-alkyl, $C_1$-$C_{10}$-alkylthio-$C_1$-$C_6$-alkyl, optionally halogen-, $C_1$-$C_6$-alkyl- or $C_1$-$C_6$-alkoxy-substituted $C_3$-$C_8$-cycloalkyl in which optionally one or two not directly adjacent ring members are replaced by oxygen and/or sulfur or represents phenyl, naphthyl, hetaryl having 5 or 6 ring atoms (for example furanyl, pyridyl, imidazolyl, triazolyl, pyrazolyl, pyrimidyl, thiazolyl or thienyl), phenyl-$C_1$-$C_6$-alkyl or naphthyl-$C_1$-$C_6$-alkyl, each of which is optionally substituted by halogen, $C_1$-$C_6$-alkyl, $C_1$-$C_6$-haloalkyl, $C_1$-$C_6$-alkoxy, $C_1$-$C_6$-haloalkoxy, cyano or nitro, B preferably represents hydrogen, $C_1$-$C_{12}$-alkyl or $C_1$-$C_8$-alkoxy-$C_1$-$C_6$-alkyl, with the proviso that A and B may each only represent methyl if, in the case of W, X and Y each representing $C_1$-$C_6$-alkyl and Z representing hydrogen, W and X must each represent methyl or W and X must each represent ethyl, or A, B and the carbon atom to which they are attached preferably represent saturated $C_3$-$C_{10}$-cycloalkyl or unsaturated $C_5$-$C_{10}$-cycloalkyl in which optionally one ring member is replaced by nitrogen, oxygen or sulfur and which are optionally mono- or disubstituted by $C_1$-$C_8$-alkyl, $C_1$-$C_8$-alkoxy, $C_3$-$C_8$-alkenyloxy, $C_1$-$C_6$-alkoxy-$C_1$-$C_6$-alkyl, $C_3$-$C_6$-cycloalkyl-$C_1$-$C_2$-alkoxy, $C_3$-$C_{10}$-cycloalkyl, $C_1$-$C_8$-haloalkyl, $C_2$-$C_6$-haloalkoxy, $C_1$-$C_6$-alkoxy-$C_1$-$C_4$-alkoxy, where the radicals mentioned above (except for trifluoromethyl) are also suitable as N-substituents, or A, B and the carbon atom to which they are attached preferably represent $C_3$-$C_6$-cycloalkyl which is substituted by an alkylendiyl group, which optionally contains one or two not directly adjacent oxygen and/or sulfur atoms and is optionally substituted by $C_1$-$C_4$-alkyl, or by an alkylenedioxyl group or by an alkylenedithioyl group which, together with the carbon atom to which it is attached, forms a further five- to eight-membered ring or A, B and the carbon atom to which they are attached preferably represent $C_3$-$C_8$-cycloalkyl or $C_5$-$C_8$-cycloalkenyl in which two substituents together with the carbon atoms to which they are attached represent $C_2$-$C_6$-alkanediyl, $C_2$-$C_6$-alkenediyl or $C_4$-$C_6$-alkanedienediyl, each of which is optionally substituted by $C_1$-$C_6$-alkyl, $C_1$-$C_6$-alkoxy or halogen and in which optionally one methylene group is replaced by oxygen or sulfur, G preferably represents one of the groups (a)
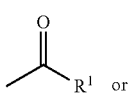

or (b)
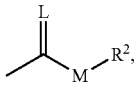

in which

L represents oxygen or sulfur,

M represents oxygen or sulfur, $R^1$ preferably represents in each case optionally halogen- or cyano-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl or poly-$C_1$-$C_8$-alkoxy-$C_1$-$C_8$-alkyl or represents optionally halogen-, $C_1$-$C_6$-alkyl- or $C_1$-$C_6$-alkoxy-substituted $C_3$-$C_8$-cycloalkyl in which optionally one or two not directly adjacent methylene groups are replaced by oxygen and/or sulfur, represents optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio- or $C_1$-$C_6$-alkylsulfonyl-substituted phenyl, represents optionally halogen-, nitro-, cyano-, $C_1$-$C_6$-alkyl-, $C_1$-$C_6$-alkoxy-, $C_1$-$C_6$-haloalkyl- or $C_1$-$C_6$-haloalkoxy-substituted phenyl-$C_1$-$C_6$-alkyl, represents optionally halogen- or $C_1$-$C_6$-alkyl-substituted 5- or 6-membered hetaryl having one or two heteroatoms from the group consisting of oxygen, sulfur and nitrogen, represents optionally halogen- or $C_1$-$C_6$-alkyl-substituted phenoxy-$C_1$-$C_6$-alkyl or represents optionally halogen- or $C_1$-$C_6$-alkyl-substituted 5- or 6-membered hetaryloxy-$C_1$-$C_6$-alkyl having one or two heteroatoms from the group consisting of oxygen, sulfur and nitrogen.

$R^2$ preferably represents in each case optionally halogen- or cyano-substituted $C_1$-$C_{20}$-alkyl, $C_2$-$C_{20}$-alkenyl, $C_1$-$C_8$-alkoxy-$C_2$-$C_8$-alkyl or poly-$C_1$-$C_8$-alkoxy-$C_2$-$C_8$-alkyl, represents optionally halogen-, $C_1$-$C_6$-alkyl or $C_1$-$C_6$-alkoxy-substituted $C_3$-$C_8$-cycloalkyl or represents phenyl or benzyl, each of which is optionally substituted by halogen, cyano, nitro, $C_1$-$C_6$-alkyl, $C_1$-$C_6$-alkoxy, $C_1$-$C_6$-haloalkyl or $C_1$-$C_6$-haloalkoxy.

In the radical definitions mentioned as being preferred, halogen represents fluorine, chlorine, bromine and iodine, in particular fluorine, chlorine and bromine W particularly preferably represents hydrogen, chlorine, bromine, $C_1$-$C_4$-alkyl, $C_2$-$C_4$-alkenyl, $C_2$-$C_4$-alkynyl, $C_3$-$C_6$-cycloalkyl which is optionally monosubstituted by methyl, ethyl, methoxy, fluorine, chlorine, trifluoromethyl or cyclopropyl, $C_1$-$C_4$-alkoxy, $C_1$-$C_2$-haloalkyl or $C_1$-$C_2$-haloalkoxy, X particularly preferably represents chlorine, bromine, iodine, $C_1$-$C_4$-alkyl, $C_2$-$C_4$-alkenyl, $C_2$-$C_4$-alkynyl, $C_3$-$C_6$-cycloalkyl which is optionally monosubstituted by methyl, ethyl, methoxy, fluorine, chlorine, trifluoromethyl or cyclopropyl, $C_1$-$C_4$-alkoxy, $C_1$-$C_4$-haloalkyl, $C_1$-$C_4$-haloalkoxy or cyano, Y and Z independently of one another particularly preferably represent hydrogen, fluorine, chlorine, bromine, iodine, $C_1$-$C_4$-alkyl, $C_2$-$C_4$-alkenyl, $C_2$-$C_4$-alkynyl, $C_3$-$C_6$-cycloalkyl which is optionally monosubstituted by methyl, ethyl, methoxy, fluorine, chlorine, trifluoromethyl or cyclopropyl, $C_1$-$C_6$-alkoxy, $C_1$-$C_4$-haloalkyl, $C_1$-$C_4$-haloalkoxy, cyano, $C_2$-$C_4$-alkenyl, $C_2$-$C_4$-alkynyl or represents one of the (Het)-aryl radicals,

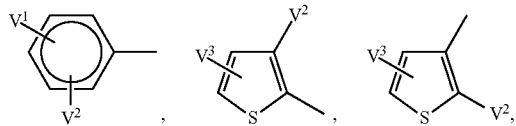

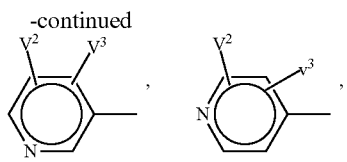

-continued

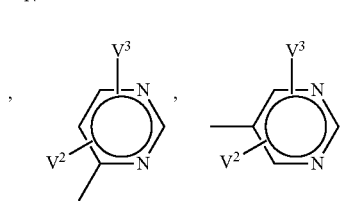

where in the case of (het)aryl only one of the radicals Y or Z may represent (het)aryl, $V^1$ particularly preferably represents hydrogen, fluorine, chlorine, bromine, $C_1$-$C_6$-alkyl, $C_1$-$C_4$-alkoxy, $C_1$-$C_2$-haloalkyl, $C_1$-$C_2$-haloalkoxy, nitro, cyano or phenyl which is optionally mono- or disubstituted by fluorine, chlorine, bromine, $C_1$-$C_4$-alkyl, $C_1$-$C_4$-alkoxy, $C_1$-$C_2$-haloalkyl, $C_1$-$C_2$-haloalkoxy, nitro or cyano, $V^2$ and $V^3$ independently of one another particularly preferably represent hydrogen, fluorine, chlorine, bromine, $C_1$-$C_4$-alkyl, $C_1$-$C_4$-alkoxy, $C_1$-$C_2$-haloalkyl or $C_1$-$C_2$-haloalkoxy, A particularly preferably represents hydrogen, represents $C_1$-$C_6$-alkyl, $C_1$-$C_4$-alkoxy-$C_1$-$C_2$-alkyl, each of which is optionally mono- to trisubstituted by fluorine or chlorine, represents $C_3$-$C_6$-cycloalkyl which is optionally mono- or disubstituted by $C_1$-$C_2$-alkyl or $C_1$-$C_2$-alkoxy and optionally interrupted by an oxygen atom or represents phenyl, pyridyl or benzyl, each of which is optionally mono- or disubstituted by fluorine, chlorine, bromine, $C_1$-$C_4$-alkyl, $C_1$-$C_2$-haloalkyl, $C_1$-$C_4$-alkoxy, $C_1$-$C_2$-haloalkoxy, cyano or nitro, B particularly preferably represents hydrogen, $C_1$-$C_4$-alkyl or $C_1$-$C_2$-alkoxyl-$C_1$-$C_2$-alkyl, with the proviso that A and B may each only represent methyl if, in the case of W, X and Y each representing $C_1$-$C_4$-alkyl and Z representing hydrogen, W and X must each represent methyl or W and X must each represent ethyl, or A, B and the carbon atom to which they are attached particularly preferably represent saturated or unsaturated $C_3$-$C_7$-cycloalkyl in which optionally one ring member is replaced by nitrogen, oxygen or sulfur and which is optionally monosubstituted or disubstituted by $C_1$-$C_6$-alkyl, $C_1$-$C_4$-alkoxy-$C_1$-$C_2$-alkyl, trifluoromethyl, $C_1$-$C_6$-alkoxy, $C_3$-$C_6$-alkenyloxy, trifluoroethoxy, $C_1$-$C_3$-alkoxy-$C_1$-$C_3$-alkoxy or $C_3$-$C_6$-cycloalkylmethoxy, where the radicals mentioned above (except for trifluoromethyl) are also suitable as N-substituents, or A, B and the carbon atom to which they are attached particularly preferably represent $C_5$-$C_6$-cycloalkyl which is substituted by an alkylendiyl group, which optionally contains one or two not directly adjacent oxygen or sulfur atoms and is optionally substituted by methyl or ethyl, or by an alkylenedioxyl group or by an alkylenedithiol group which, together with the carbon atom to which it is attached, forms a further five- or six-membered ring or A, B and the carbon atom to which they are attached particularly preferably represent $C_3$-$C_6$-cycloalkyl or $C_5$-$C_6$-cycloalkenyl in which two substituents together with the carbon atoms to which they are attached represent $C_2$-$C_4$- alkanediyl, $C_2$-$C_4$-alkenediyl or butadienediyl, each of which is optionally substituted by $C_1$-$C_2$-alkyl or $C_1$-$C_2$-alkoxy, G particularly preferably represents one of the groups

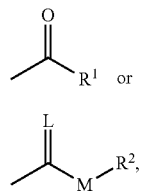

in which

L represents oxygen or sulfur,

M represents oxygen or sulfur, $R^1$ particularly preferably represents $C_1$-$C_{16}$-alkyl, $C_2$-$C_{16}$-alkenyl, $C_1$-$C_6$-alkoxy-$C_1$-$C_4$-alkyl, $C_1$-$C_6$-alkylthio-$C_1$-$C_4$-alkyl or poly-$C_1$-$C_6$-alkoxy-$C_1$-$C_4$-alkyl, each of which is optionally mono- to trisubstituted by fluorine or chlorine, or represents $C_3$-$C_7$-cycloalkyl which is optionally mono- or disubstituted by fluorine, chlorine, $C_1$-$C_5$-alkyl or $C_1$-$C_5$-alkoxy and in which optionally one or two not directly adjacent methylene groups are replaced by oxygen and/or sulfur, represents phenyl which is optionally mono- to trisubstituted by fluorine, chlorine, bromine, cyano, nitro, $C_1$-$C_4$-alkyl, $C_1$-$C_4$-alkoxy, $C_1$-$C_3$-haloalkyl, $C_1$-$C_3$-haloalkoxy, $C_1$-$C_4$-alkylthio or $C_1$-$C_4$-alkylsulfonyl, represents phenyl-$C_1$-$C_4$-alkyl, which is optionally mono- or disubstituted by fluorine, chlorine, bromine, $C_1$-$C_4$-alkyl, $C_1$-$C_4$-alkoxy, $C_1$-$C_3$-haloalkyl or $C_1$-$C_3$-haloalkoxy, represents pyrazolyl, thiazolyl, pyridyl, pyrimidyl, furanyl or thienyl, each of which is optionally mono- or disubstituted by fluorine, chlorine, bromine or $C_1$-$C_4$-alkyl, represents phenoxy-$C_1$-$C_5$-alkyl which is optionally mono- or disubstituted by fluorine, chlorine, bromine or $C_1$-$C_4$-alkyl, represents pyridyloxy-$C_1$-$C_5$-alkyl, pyrimidyloxy-$C_1$-$C_5$-alkyl or thiazolyloxy-$C_1$-$C_5$-alkyl, each of which is optionally mono- or disubstituted by fluorine, chlorine, bromine, amino or $C_1$-$C_4$-alkyl, $R^2$ particularly preferably represents $C_1$-$C_{16}$-alkyl, $C_2$-$C_{16}$-alkenyl, $C_1$-$C_6$-alkoxy-$C_2$-$C_6$-alkyl or poly-$C_1$-$C_6$-alkoxy-$C_2$-$C_6$-alkyl, each of which is optionally mono- to trisubstituted by fluorine or chlorine, represents $C_3$-$C_7$-cycloalkyl which is optionally mono- or disubstituted by fluorine, chlorine, $C_1$-$C_4$-alkyl or $C_1$-$C_4$-alkoxy or represents phenyl or benzyl, each of which is optionally mono- to trisubstituted by fluorine, chlorine, bromine, cyano, nitro, $C_1$-$C_4$-alkyl, $C_1$-$C_3$-alkoxy, $C_1$-$C_3$-haloalkyl or $C_1$-$C_3$-haloalkoxy.

In the radical definitions mentioned as being particularly preferred, halogen represents fluorine, chlorine and bromine, in particular fluorine and chlorine.

W very particularly preferably represents hydrogen, chlorine, bromine, methyl, ethyl, propyl, vinyl, ethynyl, propynyl, cyclopropyl, methoxy, ethoxy or trifluoromethyl, X very particularly preferably represents chlorine, bromine, methyl, ethyl, propyl, isopropyl, vinyl, ethynyl, propynyl, cyclopropyl, methoxy, ethoxy, trifluoromethyl, difluoromethoxy, trifluoromethoxy or cyano, Y and Z independently of one another very particularly preferably represent hydrogen, fluorine, chlorine, bromine, iodine, methyl, ethyl, vinyl, ethynyl, propynyl, cyclopropyl, methoxy, trifluoromethyl, trifluoromethoxy, cyano or a phenyl radical,

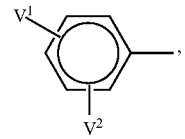

where in the case of phenyl only one of the radicals Y or Z may represent phenyl, $V^1$ very particularly preferably represents hydrogen, fluorine or chlorine, $V^2$ very particularly preferably represents hydrogen, fluorine, chlorine, methyl, ethyl, n-propyl, isopropyl, methoxy, ethoxy or trifluoromethyl, A very particularly preferably represents hydrogen, represents $C_1$-$C_4$-alkyl or $C_1$-$C_2$-alkoxy-$C_1$-$C_2$-alkyl, each of which is optionally mono- to trisubstituted by fluorine, represents cyclopropyl, cyclopentyl or cyclohexyl, B very particularly preferably represents hydrogen, methyl or ethyl, with the proviso that A and B may each only represent methyl if, in the case of W, X and Y each representing methyl or ethyl and Z representing hydrogen, W and X must each represent methyl or W and X must each represent ethyl, or A, B and the carbon atom to which they are attached very particularly preferably represent saturated $C_5$-$C_6$-cycloalkyl in which optionally one ring member is replaced by nitrogen, oxygen or sulfur and which is optionally mono- or disubstituted by methyl, ethyl, methoxymethyl, ethoxymethyl, methoxyethyl, ethoxyethyl, trifluoromethyl, methoxy, ethoxy, propoxy, butoxy, methoxyethoxy, ethoxyethoxy, allyloxy, trifluorethoxy or cyclopropylmethoxy, where the radicals mentioned above (except for trifluoromethyl) are also suitable as N-substituents, or A, B and the carbon atom to which they are attached particularly preferably represent $C_6$-cycloalkyl which is optionally substituted by an alkylendiyl group, which is optionally interrupted by an oxygen atom, or by an alkylenedioxy group, which contains two not directly adjacent oxygen atoms, thus forming a further 5- or 6-membered ring (which may optionally be mono- or disubstituted by methyl), or A, B and the carbon atom to which they are attached very particularly preferably represent $C_5$-$C_6$-cycloalkyl or $C_5$-$C_6$-cycloalkenyl in which two substituents together with the carbon atoms to which they are attached represent $C_2$-$C_4$-alkanediyl or $C_2$-$C_4$-alkenediyl or butadienediyl, G particularly preferably represents one of the groups

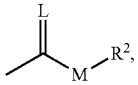
(b)

in which
L represents oxygen or sulfur,
M represents oxygen or sulfur,
$R^1$ very particularly preferably represents $C_1$-$C_{10}$-alkyl, $C_2$-$C_{10}$-alkenyl, $C_1$-$C_4$-alkoxy-$C_1$-$C_2$-alkyl, $C_1$-$C_4$-alkylthio-$C_1$-$C_2$-alkyl, each of which is optionally mono- to trisubstituted by fluorine or chlorine, or represents $C_3$-$C_6$-cycloalkyl which is optionally substituted by fluorine, chlorine, methyl, ethyl or methoxy,
represents phenyl which is optionally mono- or disubstituted by fluorine, chlorine, bromine, cyano, nitro, methyl, ethyl, n-propyl, isopropyl, methoxy, ethoxy, trifluoromethyl or trifluoromethoxy,
represents furanyl, thienyl or pyridyl, each of which is optionally monosubstituted by chlorine, bromine or methyl,
$R^2$ very particularly preferably represents $C_1$-$C_{10}$-alkyl, $C_2$-$C_{10}$-alkenyl or $C_1$-$C_4$-alkoxy-$C_2$-$C_4$-alkyl, each of which is optionally mono- to trisubstituted by fluorine or chlorine,
represents cyclopentyl or cyclohexyl
or represents phenyl or benzyl, each of which is optionally mono- or disubstituted by fluorine, chlorine, cyano, nitro, methyl, ethyl, methoxy, trifluoromethyl or trifluoromethoxy.
W especially preferably represents methyl, ethyl or propyl,
X especially preferably represents methyl, ethyl, chlorine, bromine or methoxy,
Y especially preferably represents methyl, chlorine, iodine or bromine,
Z especially preferably represents hydrogen,
A especially preferably represents methyl,
B especially preferably represents methyl,
with the proviso that A and B may each only represent methyl if, in the case of W, X and Y each representing methyl or ethyl and Z representing hydrogen, W and X must each represent methyl or W and X must each represent ethyl,
A, B and the carbon to which they are attached especially preferably represent $C_6$-cycloalkyl which is optionally substituted by methyl, methoxy or methoxymethyl, where the substituent may be located in the 4-position of the cycle,
G especially preferably represents one of the groups

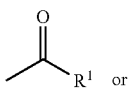
(a)

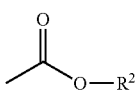
(b)

in which
$R^1$ especially preferably represents methyl, ethyl, propyl, isopropyl, butyl, isobutyl, sec-butyl or tert-butyl (with emphasis isopropyl or tert-butyl), $R^2$ especially preferably represents methyl, ethyl, propyl, isopropyl, butyl, isobutyl, sec-butyl or tert-butyl (with emphasis ethyl).
W also especially preferably represents hydrogen,
X also especially preferably represents methyl,
Y also especially preferably represents hydrogen,
Z also especially preferably represents methyl,
A, B and the carbon to which they are attached also especially preferably represent $C_6$-cycloalkyl which is optionally substituted by methoxy or methoxymethyl, where the substituent may be located either in the 3- or in the 4-position of the cycle,
G also especially preferably represents one of the groups

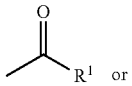
(a)

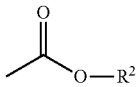
(b)

in which
$R^1$ also especially preferably represents methyl, ethyl, propyl, isopropyl, butyl, isobutyl, sec-butyl or tert-butyl (with particular emphasis $C(CH_3)_2C_2H_5$),
$R^2$ also especially preferably represents methyl, ethyl, propyl, isopropyl, butyl, isobutyl, sec-butyl or tert-butyl (with emphasis ethyl).

The abovementioned general radical definitions or illustrations mentioned in the preferred ranges can be combined with one another as desired, i.e. including combinations between the respective ranges and preferred ranges. They apply both to the end products and, correspondingly, to precursors and intermediates.

Preference is given in accordance with the invention to the compounds of the formula (I) in which a combination of the definitions listed above as preferred (preferably) is present.

Particular preference is given in accordance with the invention to the compounds of the formula (I) in which a combination of the definitions listed above as more preferred is present.

Very particular preference is given in accordance with the invention to the compounds of the formula (I) in which a combination of the definitions listed above as even more preferred is present.

Special preference according to the invention is given to the compounds of the formula (I) in which a combination of the meanings listed above as being especially preferred is present.

Emphasis is given to compounds of the formula (I) in which A and B together with the carbon atom to which they are attached represent a saturated or unsaturated cycle which is unsubstituted or substituted and optionally contains at least one heteroatom, or the corresponding preferred, particularly preferred, very particularly preferred and especially preferred definitions.

Saturated or unsaturated hydrocarbon radicals, such as alkyl or alkenyl, can in each case be straight-chain or branched as far as this is possible, including in combination with heteroatoms, such as, for example, in alkoxy.

Unless indicated otherwise, optionally substituted radicals may be mono- or polysubstituted, where in the case of polysubstitutions the substituents may be identical or different.

In addition to the compounds mentioned in the examples, the following compounds of the formula (I) where G=COCH₃ may be specifically mentioned:

TABLE 1

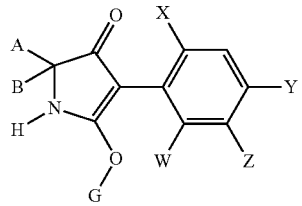

(I)

| A | B | X | W | Y | Z |
|---|---|---|---|---|---|
| CH₃ | CH₃ | CH₃ | H | H | H |
| CH₃ | CH₃ | Br | H | H | H |
| CH₃ | CH₃ | Cl | H | H | H |
| CH₃ | CH₃ | CF₃ | H | H | H |
| CH₃ | CH₃ | OCH₃ | H | H | H |
| CH₃ | CH₃ | Br | H | Cl | H |
| CH₃ | CH₃ | Cl | H | Br | H |
| CH₃ | CH₃ | Cl | H | Cl | H |
| CH₃ | CH₃ | Cl | H | CH₃ | H |
| CH₃ | CH₃ | CH₃ | H | Cl | H |
| CH₃ | CH₃ | Cl | Cl | H | H |
| CH₃ | CH₃ | Cl | OCH₃ | H | H |
| CH₃ | CH₃ | Cl | CH₃ | H | H |
| CH₃ | CH₃ | Cl | OC₂H₅ | H | H |
| CH₃ | CH₃ | OCH₃ | OCH₃ | H | H |
| CH₃ | CH₃ | CH₃ | CH₃ | H | H |
| CH₃ | CH₃ | C₂H₅ | CH₃ | H | H |
| CH3 | CH₃ | C₂H₅ | C₂H₅ | H | H |
| CH3 | CH₃ | Br | CH₃ | Br | H |
| CH3 | CH₃ | Cl | CH₃ | Cl | H |
| CH3 | CH₃ | CH₃ | Br | CH₃ | H |
| CH3 | CH₃ | CH₃ | Cl | CH₃ | H |
| CH3 | CH₃ | OCH₃ | CH₃ | CH₃ | H |
| CH3 | CH₃ | OC₂H₅ | CH₃ | CH₃ | H |
| CH3 | CH₃ | OC₃H₇ | CH₃ | CH₃ | H |
| CH3 | CH₃ | CH₃ | CH₃ | CH₃ | H |
| CH3 | CH₃ | Br | Br | CH₃ | H |
| CH₃ | CH₃ | Cl | Cl | CH₃ | H |
| CH₃ | CH₃ | CH₃ | CH₃ | Br | H |
| CH₃ | CH₃ | OCH₃ | C₂H₅ | CH₃ | H |
| CH₃ | CH₃ | OC₂H₅ | C₂H₅ | CH₃ | H |
| CH₃ | CH₃ | CH₃ | CH₃ | OCH₃ | H |
| CH₃ | CH₃ | Br | Cl | CH₃ | H |
| CH₃ | CH₃ | Br | CH₃ | Cl | H |
| CH₃ | CH₃ | Cl | CH₃ | Br | H |
| CH₃ | CH₃ | CH₃ | CH₃ | Cl | H |
| CH₃ | CH₃ | C₂H₅ | CH₃ | CH₃ | H |
| CH₃ | CH₃ | C₂H₅ | C₂H₅ | CH₃ | H |
| CH₃ | CH₃ | C₂H₅ | CH₃ | C₂H₅ | H |
| CH₃ | CH₃ | C₂H₅ | C₂H₅ | C₂H₅ | H |
| CH₃ | CH₃ | C₂H₅ | CH₃ | Cl | H |
| CH₃ | CH₃ | C₂H₅ | C₂H₅ | Cl | H |
| CH₃ | CH₃ | C₂H₅ | CH₃ | Br | H |
| CH₃ | CH₃ | C₂H₅ | C₂H₅ | Br | H |
| CH₃ | CH₃ | C₂H₅ | Cl | CH₃ | H |
| CH₃ | CH₃ | C₂H₅ | Br | CH₃ | H |
| CH₃ | CH₃ | C₂H₅ | Cl | Cl | H |
| CH₃ | CH₃ | C₂H₅ | Br | Br | H |
| CH₃ | CH₃ | C₂H₅ | Cl | Br | H |
| CH₃ | CH₃ | C₂H₅ | Br | Cl | H |
| CH₃ | CH₃ | OCH₃ | CH₃ | Cl | H |
| CH₃ | CH₃ | OCH₃ | C₂H₅ | Cl | H |
| CH₃ | CH₃ | OC₂H₅ | CH₃ | Cl | H |
| CH₃ | CH₃ | OC₂H₅ | C₂H₅ | Cl | H |
| CH₃ | CH₃ | Cl | OCH₃ | CH₃ | H |
| CH₃ | CH₃ | Cl | OC₂H₅ | CH₃ | H |
| CH₃ | CH₃ | CH₃ | CH₃ | Cl | H |
| CH₃ | CH₃ | Cl | H | Cl | Cl |
| CH₃ | CH₃ | CH₃ | H | CH₃ | CH₃ |
| CH₃ | CH₃ | CH₃ | H | Cl | CH₃ |
| CH₃ | CH₃ | Br | H | Cl | CH₃ |

TABLE 1-continued

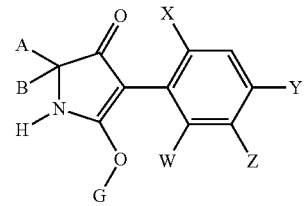

(I)

| A | B | X | W | Y | Z |
|---|---|---|---|---|---|
| CH₃ | CH₃ | Br | H | CH₃ | CH₃ |
| CH₃ | CH₃ | Cl | H | Br | CH₃ |
| CH₃ | CH₃ | Cl | H | Cl | CH₃ |
| CH₃ | CH₃ | CH₃ | H | Br | CH₃ |
| CH₃ | CH₃ | Cl | H | CH₃ | Cl |
| CH₃ | CH₃ | CH₃ | H | H | CH₃ |
| CH₃ | CH₃ | Cl | H | H | CH₃ |
| CH₃ | CH₃ | Br | H | H | CH₃ |
| CH₃ | CH₃ | CH₃ | H | H | Cl |
| CH₃ | CH₃ | CH₃ | H | H | Br |
| CH₃ | CH₃ | CH₃ | CH₃ | CH₃ | CH₃ |
| CH₃ | CH₃ | CH₃ | CH₃ | CH₃ | F |
| CH₃ | CH₃ | CH₃ | CH₃ | CH₃ | Cl |
| CH₃ | CH₃ | CH₃ | CH₃ | CH₃ | Br |
| CH₃ | CH₃ | CH₃ | CH₃ | H | Cl |
| CH₃ | CH₃ | CH₃ | CH₃ | H | Br |
| CH₃ | CH₃ | Cl | Cl | H | Br |
| CH₃ | CH₃ | CH₃ | CH₃ | 4-Cl—C₆H₄ | H |
| CH₃ | CH₃ | C₂H₅ | CH₃ | 4-Cl—C₆H₄ | H |
| CH₃ | CH₃ | C₂H₅ | C₂H₅ | 4-Cl—C₆H₄ | H |
| CH₃ | CH₃ | Cl | CH₃ | 4-Cl—C₆H₄ | H |
| CH₃ | CH₃ | Cl | C₂H₅ | 4-Cl—C₆H₄ | H |
| CH₃ | CH₃ | CH₃ | H | H | 4-Cl—C₆H₄ |
| CH₃ | CH₃ | CH₃ | CH₃ | H | 4-Cl—C₆H₄ |
| CH₃ | CH₃ | CH₃ | H | CH₃ | 4-Cl—C₆H₄ |
| CH₃ | CH₃ | CH₃ | CH₃ | CH₃ | 4-Cl—C₆H₄ |
| CH₃ | CH₃ | Cl | H | H | 4-Cl—C₆H₄ |
| CH₃ | CH₃ | I | H | H | H |
| CH₃ | CH₃ | I | H | CH₃ | H |
| CH₃ | CH₃ | I | CH₃ | H | H |
| CH₃ | CH₃ | I | C₂H₅ | H | H |
| CH₃ | CH₃ | CH₃ | H | H | I |
| CH₃ | CH₃ | CH₃ | H | CH₃ | I |
| CH₃ | CH₃ | I | CH₃ | CH₃ | H |
| CH₃ | CH₃ | I | C₂H₅ | CH₃ | H |
| CH₃ | CH₃ | I | CH₃ | Cl | H |
| CH₃ | CH₃ | I | C₂H₅ | Cl | H |
| CH₃ | CH₃ | I | Cl | CH₃ | H |
| CH₃ | CH₃ | I | H | CH₃ | CH₃ |
| CH₃ | CH₃ | CH₃ | H | I | H |
| CH₃ | CH₃ | C₂H₅ | H | I | H |
| CH₃ | CH₃ | CH₃ | CH₃ | I | H |
| CH₃ | CH₃ | C₂H₅ | CH₃ | I | H |
| CH₃ | CH₃ | C₂H₅ | C₂H₅ | I | H |
| CH₃ | CH₃ | Cl | CH₃ | I | H |
| CH₃ | CH₃ | Cl | C₂H₅ | I | H |
| CH₃ | CH₃ | CH₃ | H | I | CH₃ |
| CH₃ | CH₃ | CH₃ | CH₃ | H | I |
| CH₃ | CH₃ | I | H | H | CH₃ |
| CH₃ | CH₃ | C₂H₅ | H | H | H |
| CH₃ | CH₃ | △ | H | H | H |
| CH₃ | CH₃ | △ | CH₃ | H | H |
| CH₃ | CH₃ | △ | H | CH₃ | H |
| CH₃ | CH₃ | △ | C₂H₅ | H | H |
| CH₃ | CH₃ | △ | CH₃ | CH₃ | H |

TABLE 1-continued

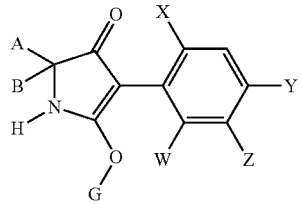

(I)

| A | B | X | W | Y | Z |
|---|---|---|---|---|---|
| CH$_3$ | CH$_3$ | △ | C$_2$H$_5$ | CH$_3$ | H |
| CH$_3$ | CH$_3$ | △ | CH$_3$ | Cl | H |
| CH$_3$ | CH$_3$ | △ | C$_2$H$_5$ | Cl | H |
| CH$_3$ | CH$_3$ | △ | Cl | CH$_3$ | H |
| CH$_3$ | CH$_3$ | CH$_3$ | H | △ | H |
| CH$_3$ | CH$_3$ | C$_2$H$_5$ | H | △ | H |
| CH$_3$ | CH$_3$ | CH$_3$ | CH$_3$ | △ | H |
| CH$_3$ | CH$_3$ | C$_2$H$_5$ | CH$_3$ | △ | H |
| CH$_3$ | CH$_3$ | C$_2$H$_5$ | C$_2$H$_5$ | △ | H |
| CH$_3$ | CH$_3$ | Cl | CH$_3$ | △ | H |
| CH$_3$ | CH$_3$ | Cl | C$_2$H$_5$ | △ | H |

Furthermore, in addition to the compounds mentioned in the examples, the following compounds of the formula (I) where G=COCH$_3$ and

Z=

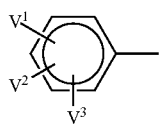

may be mentioned:

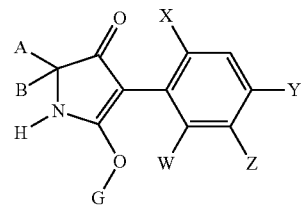

(I)

TABLE 2

| A | B | W | X | Y | V$^1$ | V$^2$ | V$^3$ |
|---|---|---|---|---|---|---|---|
| CH$_3$ | CH$_3$ | H | Cl | H | 2-F | H | H |
| CH$_3$ | CH$_3$ | H | Cl | H | 3-F | H | H |
| CH$_3$ | CH$_3$ | H | Cl | H | 4-F | H | H |
| CH$_3$ | CH$_3$ | H | Cl | H | 2-F | 4-F | H |
| CH$_3$ | CH$_3$ | H | Cl | H | 2-F | 4-Cl | H |
| CH$_3$ | CH$_3$ | H | Cl | H | 2-F | 4-CH$_3$ | H |
| CH$_3$ | CH$_3$ | H | Cl | H | 2-F | 4-OCH$_3$ | H |
| CH$_3$ | CH$_3$ | H | Cl | H | 3-F | 4-F | H |
| CH$_3$ | CH$_3$ | H | Cl | H | 3-F | 4-Cl | H |
| CH$_3$ | CH$_3$ | H | Cl | H | 3-F | 4-CH$_3$ | H |
| CH$_3$ | CH$_3$ | H | Cl | H | 3-F | 4-OCH$_3$ | H |
| CH$_3$ | CH$_3$ | H | Cl | H | 4-F | 3-Cl | H |
| CH$_3$ | CH$_3$ | H | Cl | H | 4-F | 3-CH$_3$ | H |
| CH$_3$ | CH$_3$ | H | Cl | H | 4-F | 3-OCH$_3$ | H |
| CH$_3$ | CH$_3$ | H | Cl | H | 2-F | 4-F | 5-F |
| CH$_3$ | CH$_3$ | H | Cl | H | 2-F | 4-F | 6-F |
| CH$_3$ | CH$_3$ | H | Cl | H | 2-F | 4-Cl | 5-F |
| CH$_3$ | CH$_3$ | H | Cl | H | 2-F | 5-Cl | 4-F |
| CH$_3$ | CH$_3$ | H | Cl | H | 3-F | 4-F | 5-F |
| CH$_3$ | CH$_3$ | H | Cl | H | 3-Cl | 4-Cl | H |
| CH$_3$ | CH$_3$ | H | Cl | H | 4-CF$_3$ | 3-F | H |
| CH$_3$ | CH$_3$ | H | Cl | H | 4-CN | H | H |
| CH$_3$ | CH$_3$ | H | Cl | H | 3-CF$_3$ | 4-F | H |
| CH$_3$ | CH$_3$ | H | CH$_3$ | H | 2-F | H | H |
| CH$_3$ | CH$_3$ | H | CH$_3$ | H | 3-F | H | H |
| CH$_3$ | CH$_3$ | H | CH$_3$ | H | 4-F | H | H |
| CH$_3$ | CH$_3$ | H | CH$_3$ | H | 2-F | 4-F | H |
| CH$_3$ | CH$_3$ | H | CH$_3$ | H | 2-F | 4-Cl | H |
| CH$_3$ | CH$_3$ | H | CH$_3$ | H | 2-F | 4-CH$_3$ | H |
| CH$_3$ | CH3 | H | CH$_3$ | H | 2-F | 4-OCH$_3$ | H |
| CH$_3$ | CH$_3$ | H | CH$_3$ | H | 3-F | 4-F | H |
| CH$_3$ | CH3 | H | CH$_3$ | H | 3-F | 4-Cl | H |
| CH$_3$ | CH$_3$ | H | CH$_3$ | H | 3-F | 4-CH$_3$ | H |
| CH$_3$ | CH$_3$ | H | CH$_3$ | H | 3-F | 4-OCH$_3$ | H |
| CH$_3$ | CH$_3$ | H | CH$_3$ | H | 4-F | 3-Cl | H |
| CH$_3$ | CH$_3$ | H | CH$_3$ | H | 4-F | 3-CH$_3$ | H |
| CH$_3$ | CH$_3$ | H | CH$_3$ | H | 4-F | 3-OCH$_3$ | H |
| CH$_3$ | CH$_3$ | H | CH$_3$ | H | 2-F | 4-F | 5-F |
| CH$_3$ | CH$_3$ | H | CH$_3$ | H | 2-F | 4-F | 6-F |
| CH$_3$ | CH$_3$ | H | CH$_3$ | H | 2-F | 4-Cl | 5-F |
| CH$_3$ | CH$_3$ | H | CH$_3$ | H | 2-F | 5-Cl | 4-F |
| CH$_3$ | CH$_3$ | H | CH$_3$ | H | 3-F | 4-F | 5-F |
| CH$_3$ | CH$_3$ | H | CH$_3$ | H | 3-Cl | 4-Cl | H |
| CH$_3$ | CH$_3$ | H | CH$_3$ | H | 4-CF$_3$ | 3-F | H |
| CH$_3$ | CH$_3$ | H | CH$_3$ | H | 4-CN | H | H |
| CH$_3$ | CH$_3$ | H | CH$_3$ | H | 3-CF$_3$ | 4-F | H |
| CH$_3$ | CH$_3$ | CH$_3$ | CH$_3$ | H | 2-F | H | H |
| CH$_3$ | CH$_3$ | CH$_3$ | CH$_3$ | H | 3-F | H | H |
| CH$_3$ | CH$_3$ | CH$_3$ | CH$_3$ | H | 4-F | H | H |
| CH$_3$ | CH$_3$ | CH$_3$ | CH$_3$ | H | 2-F | 4-F | H |
| CH$_3$ | CH$_3$ | CH$_3$ | CH$_3$ | H | 2-F | 4-Cl | H |
| CH$_3$ | CH$_3$ | CH$_3$ | CH$_3$ | H | 2-F | 4-CH$_3$ | H |
| CH$_3$ | CH$_3$ | CH$_3$ | CH$_3$ | H | 2-F | 4-OCH$_3$ | H |
| CH$_3$ | CH$_3$ | CH$_3$ | CH$_3$ | H | 3-F | 4-F | H |
| CH$_3$ | CH$_3$ | CH$_3$ | CH$_3$ | H | 3-F | 4-Cl | H |
| CH$_3$ | CH$_3$ | CH$_3$ | CH$_3$ | H | 3-F | 4-CH$_3$ | H |
| CH$_3$ | CH$_3$ | CH$_3$ | CH$_3$ | H | 3-F | 4-OCH$_3$ | H |
| CH$_3$ | CH$_3$ | CH$_3$ | CH$_3$ | H | 4-F | 3-Cl | H |
| CH$_3$ | CH$_3$ | CH$_3$ | CH$_3$ | H | 4-F | 3-CH$_3$ | H |
| CH$_3$ | CH$_3$ | CH$_3$ | CH$_3$ | H | 4-F | 3-OCH$_3$ | H |
| CH$_3$ | CH$_3$ | CH$_3$ | CH$_3$ | H | 2-F | 4-F | 5-F |
| CH$_3$ | CH$_3$ | CH$_3$ | CH$_3$ | H | 2-F | 4-F | 6-F |
| CH$_3$ | CH$_3$ | CH$_3$ | CH$_3$ | H | 2-F | 4-Cl | 5-F |

TABLE 2-continued

| A | B | W | X | Y | V¹ | V² | V³ |
|---|---|---|---|---|----|----|----|
| CH₃ | CH₃ | CH₃ | CH₃ | H | 2-F | 5-Cl | 4-F |
| CH₃ | CH₃ | CH₃ | CH₃ | H | 3-F | 4-F | 5-F |
| CH₃ | CH₃ | CH₃ | CH₃ | H | 3-CF₃ | 4-F | H |
| CH₃ | CH₃ | CH₃ | CH₃ | H | 3-Cl | 4-Cl | H |
| CH₃ | CH₃ | CH₃ | CH₃ | H | 4-CF₃ | 3-F | H |
| CH₃ | CH₃ | CH₃ | CH₃ | H | 4-CN | H | H |
| CH₃ | CH₃ | H | CH₃ | CH₃ | 2-F | H | H |
| CH₃ | CH₃ | H | CH₃ | CH₃ | 3-F | H | H |
| CH₃ | CH₃ | H | CH₃ | CH₃ | 4-F | H | H |
| CH₃ | CH₃ | H | CH₃ | CH₃ | 2-F | 4-F | H |
| CH₃ | CH₃ | H | CH₃ | CH₃ | 2-F | 4-Cl | H |
| CH₃ | CH₃ | H | CH₃ | CH₃ | 2-F | 4-CH₃ | H |
| CH₃ | CH₃ | H | CH₃ | CH₃ | 2-F | 4-OCH₃ | H |
| CH₃ | CH₃ | H | CH₃ | CH₃ | 3-F | 4-F | H |
| CH₃ | CH₃ | H | CH₃ | CH₃ | 3-F | 4-Cl | H |
| CH₃ | CH₃ | H | CH₃ | CH₃ | 3-F | 4-CH₃ | H |
| CH₃ | CH₃ | H | CH₃ | CH₃ | 3-F | 4-OCH₃ | H |
| CH₃ | CH₃ | H | CH₃ | CH₃ | 4-F | 3-Cl | H |
| CH₃ | CH₃ | H | CH₃ | CH₃ | 4-F | 3-CH₃ | H |
| CH₃ | CH₃ | H | CH₃ | CH₃ | 4-F | 3-OCH₃ | H |
| CH₃ | CH₃ | H | CH₃ | CH₃ | 2-F | 4-F | 5-F |
| CH₃ | CH₃ | H | CH₃ | CH₃ | 2-F | 4-F | 6-F |
| CH₃ | CH₃ | H | CH₃ | CH₃ | 2-F | 4-Cl | 5-F |
| CH₃ | CH₃ | H | CH₃ | CH₃ | 2-F | 5-Cl | 4-F |
| CH₃ | CH₃ | H | CH₃ | CH₃ | 3-F | 4-F | 5-F |
| CH₃ | CH₃ | CH₃ | CH₃ | H | 3-Cl | 4-Cl | H |
| CH₃ | CH₃ | CH₃ | CH₃ | H | 4-CF₃ | 3-F | H |
| CH₃ | CH₃ | CH₃ | CH₃ | H | 4-CN | H | H |
| CH₃ | CH₃ | CH₃ | CH₃ | H | 3-CF₃ | 4-F | H |
| CH₃ | CH₃ | CH₃ | CH₃ | CH₃ | 2-F | H | H |
| CH₃ | CH₃ | CH₃ | CH₃ | CH₃ | 3-F | H | H |
| CH₃ | CH₃ | CH₃ | CH₃ | CH₃ | 4-F | H | H |
| CH₃ | CH₃ | CH₃ | CH₃ | CH₃ | 2-F | 4-F | H |
| CH₃ | CH₃ | CH₃ | CH₃ | CH₃ | 2-F | 4-Cl | H |
| CH₃ | CH₃ | CH₃ | CH₃ | CH₃ | 2-F | 4-CH₃ | H |
| CH₃ | CH₃ | CH₃ | CH₃ | CH₃ | 2-F | 4-OCH₃ | H |
| CH₃ | CH₃ | CH₃ | CH₃ | CH₃ | 3-F | 4-F | H |
| CH₃ | CH₃ | CH₃ | CH₃ | CH₃ | 3-F | 4-Cl | H |
| CH₃ | CH₃ | CH₃ | CH₃ | CH₃ | 3-F | 4-CH₃ | H |
| CH₃ | CH₃ | CH₃ | CH₃ | CH₃ | 3-F | 4-OCH₃ | H |
| CH₃ | CH₃ | CH₃ | CH₃ | CH₃ | 4-F | 3-Cl | H |
| CH₃ | CH₃ | CH₃ | CH₃ | CH₃ | 4-F | 3-CH₃ | H |
| CH₃ | CH₃ | CH₃ | CH₃ | CH₃ | 4-F | 3-OCH₃ | H |
| CH₃ | CH₃ | CH₃ | CH₃ | CH₃ | 2-F | 4-F | 5-F |
| CH₃ | CH₃ | CH₃ | CH₃ | CH₃ | 2-F | 4-F | 6-F |
| CH₃ | CH₃ | CH₃ | CH₃ | CH₃ | 2-F | 4-Cl | 5-F |
| CH₃ | CH₃ | CH₃ | CH₃ | CH₃ | 2-F | 5-Cl | 4-F |
| CH₃ | CH₃ | CH₃ | CH₃ | CH₃ | 3-F | 4-F | 5-F |
| CH₃ | CH₃ | CH₃ | CH₃ | H | 3-Cl | 4-Cl | H |
| CH₃ | CH₃ | CH₃ | CH₃ | H | 4-CF₃ | 3-F | H |
| CH₃ | CH₃ | CH₃ | CH₃ | H | 4-CN | H | H |
| CH₃ | CH₃ | CH₃ | CH₃ | H | 3-CF₃ | 4-F | H |

Preferred active compounds of the formula (I) according to the invention where G=COCH₃ are moreover compounds having the radical definitions for W, X, Y, Z mentioned in Table 1 and the radical definitions for W, X, Y mentioned in Table 2 and

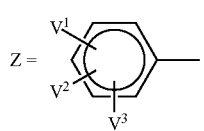

the radical definitions for A and B mentioned in Tables 3.

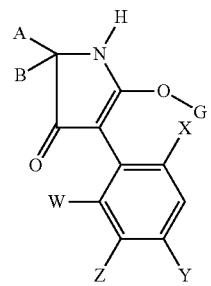

TABLE 3

| A | B |
|---|---|
| CH₃ | H |
| C₂H₅ | H |
| C₃H₇ | H |
| i-C₃H₇ | H |
| C₄H₉ | H |
| i-C₄H₉ | H |
| s-C₄H₉ | H |
| t-C₄H₉ | H |
| CH₃ | CH₃ |
| C₂H₅ | CH₃ |
| C₃H₇ | CH₃ |
| i-C₃H₇ | CH₃ |
| C₄H₉ | CH₃ |
| i-C₄H₉ | CH₃ |
| s-C₄H₉ | CH₃ |
| t-C₄H₉ | CH₃ |
| C₂H₅ | C₂H₅ |
| C₃H₇ | C₃H₇ |
| cyclopropyl | CH₃ |
| cyclopentyl | CH₃ |
| cyclohexyl | CH₃ |
| H₃CO—CH₂— | CH₃ |
| H₅C₂O—CH₂— | CH₃ |
| H₃CO—(CH₂)₂— | CH₃ |
| H₅C₂O—(CH₂)₂— | CH₃ |
| tetrahydrofuran-2-yl | CH₃ |
| tetrahydrofuran-3-yl | CH₃ |
| —(CH₂)₂— | |
| —(CH₂)₄— | |
| —(CH₂)₅— | |
| —(CH₂)₆— | |
| —(CH₂)₇— | |
| —(CH₂)₂—N(OCH₃)—(CH₂)₂— | |
| —(CH₂)₂—N(OC₂H₅)—(CH₂)₂— | |

TABLE 3-continued

| A | B |
|---|---|
| —(CH₂)₂—O—(CH₂)₂— | |
| —CH₂—O—(CH₂)₃— | |
| —(CH₂)₂—S—(CH₂)₂— | |
| —CH₂—CHCH₃—(CH₂)₃— | |
| —CH₂—CHOCH₃—(CH₂)₂— | |
| —CH₂—CHOC₂H₅—(CH₂)₂— | |
| —CH₂—CHOC₃H₇—(CH₂)₂— | |
| —CH₂—CHOC₄H₉—(CH₂)₂— | |
| —CH₂—CHO(CH₂)₂OCH₃—(CH₂)₂— | |

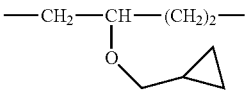

—CH₂—CHOCH₃—(CH₂)₃—
—CH₂—CHOC₂H₅—(CH₂)₃—
—CH₂—CHOC₃H₇—(CH₂)₃—
—CH₂—CHOC₄H₉—(CH₂)₃—
—CH₂—CHO(CH₂)₂OCH₃—(CH₂)₃—

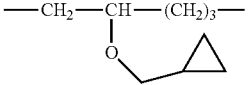

—(CH₂)₂—CHCH₃—(CH₂)₂—
—(CH₂)₂—CHC₂H₅—(CH₂)₂—
—(CH₂)₂—CHC₃H₇—(CH₂)₂—
—(CH₂)₂—CHi-C₃H₇—(CH₂)₂—
—(CH₂)₂—CHOCH₃—(CH₂)₂—
—(CH₂)₂—CHOC₂H₅—(CH₂)₂—
—(CH₂)₂—CHOC₃H₇—(CH₂)₂—
—(CH₂)₂—CHO—CH₂CF₃—(CH₂)₂—
—(CH₂)₂—C(CH₃)₂—(CH₂)₂—
—CH₂—(CHCH₃)₂—(CH₂)₂—

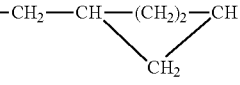

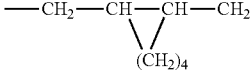

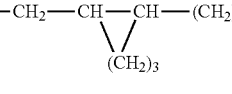

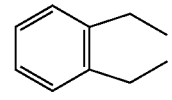

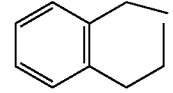

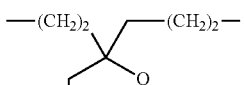

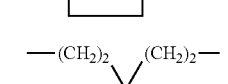

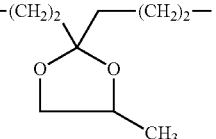

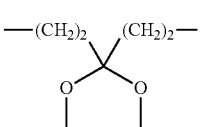

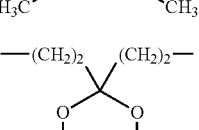

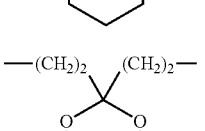

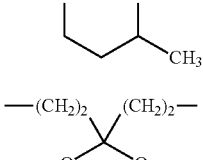

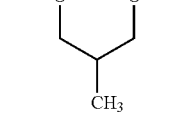

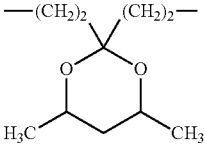

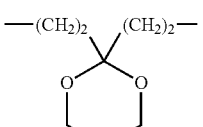

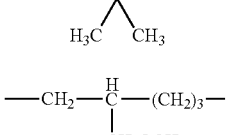

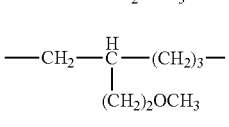

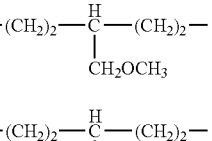

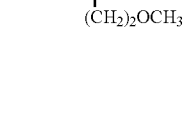

TABLE 3-continued

| A | B |
|---|---|
| 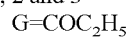 | 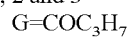 |
| 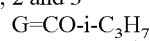 | 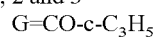 |

Table 4 A, B, $V^1$, $V^2$, $V^3$, X, W, Y and Z as indicated in Tables 1, 2 and 3
$G=COC_2H_5$
Table 5 A, B, $V^1$, $V^2$, $V^3$, X, W, Y and Z as indicated in Tables 1, 2 and 3
$G=COC_3H_7$
Table 6 A, B, $V^1$, $V^2$, $V^3$, X, W, Y and Z as indicated in Tables 1, 2 and 3
$G=CO\text{-}i\text{-}C_3H_7$
Table 7 A, B, $V^1$, $V^2$, $V^3$, X, W, Y and Z as indicated in Tables 1, 2 and 3
$G=CO\text{-}c\text{-}C_3H_5$
Table 8 A, B, $V^1$, $V^2$, $V^3$, X, W, Y and Z as indicated in Tables 1, 2 and 3
$G=COC_4H_9$
Table 9 A, B, $V^1$, $V^2$, $V^3$, X, W, Y and Z as indicated in Tables 1, 2 and 3
$G=CO\text{-}i\text{-}C_4H_9$
Table 10 A, B, $V^1$, $V^2$, $V^3$, X, W, Y and Z as indicated in Tables 1, 2 and 3
$G=CO\text{-}t\text{-}C_4H_9$
Table 11 A, B, $V^1$, $V^2$, $V^3$, X, W, Y and Z as indicated in Tables 1, 2 and 3
$G=CO_2CH_3$
Table 12 A, B, $V^1$, $V^2$, $V^3$, X, W, Y and Z as indicated in Tables 1, 2 and 3
$G=CO_2C_2H_5$
Table 13 A, B, $V^1$, $V^2$, $V^3$, X, W, Y and Z as indicated in Tables 1, 2 and 3
$G=CO_2C_3H_7$
Table 14 A, B, $V^1$, $V^2$, $V^3$, X, W, Y and Z as indicated in Tables 1, 2 and 3
$G=CO_2\text{-}i\text{-}C_2H_5$
Table 15 A, B, $V^1$, $V^2$, $V^3$, X, W, Y and Z as indicated in Tables 1, 2 and 3
$G=CO_2\text{-}t\text{-}C_4H_9$
Table 16 A, B, $V^1$, $V^2$, $V^3$, X, W, Y and Z as indicated in Tables 1, 2 and 3
$G=CO_2C_6H_5$
Table 17 A, B, $V^1$, $V^2$, $V^3$, X, W, Y and Z as indicated in Tables 1, 2 and 3
$G=CO_2CH_2C_6H_5$
with the proviso that A and B may each only represent methyl if, in the case of W, X and Y each representing alkyl and Z representing hydrogen, W and X must each represent methyl or W and X must each represent ethyl.

In the literature it has already been described how the action of various active compounds can be boosted by addition of ammonium salts. However, these are salts which act as detergents (for example WO 95/017817) or salts having relatively long-chain alkyl and/or aryl substituents which act in a permeabilizing manner or increase the solubility of the active compound (for example EP-A 0 453 086, EP-A 0 664 081, FR-A 2 600 494, U.S. Pat. No. 4,844,734, U.S. Pat. No. 5,462,912, U.S. Pat. No. 5,538,937, US-A 03/0224939, US-A 05/0009880, US-A 05/0096386). Furthermore, the prior art describes the activity only for certain active compounds and/or certain applications of the corresponding compositions. In yet other cases, these are salts of sulfonic acids where the acids for their part have a paralyzing action on insects (U.S. Pat. No. 2,842,476). A boost to action by ammonium sulfate, for example, is described by way of example for the herbicides glyphosate and phosphinothricin and for phenyl-substituted cyclic ketoenols (U.S. Pat. No. 6,645,914, EP-A2 0 036 106, WO 07/068,427). A corresponding boost to action for insecticides has already been described in WO 07/068,428.

The use of ammonium sulfate as a formulating assistant has also been described for certain active compounds and applications (WO 92/16108), but its purpose therein is to stabilize the formulation, not to boost the action.

It has now been found, entirely surprisingly, that the action of insecticides and/or acaricides and/or nematicides and/or herbicides from the class of the 2-acyloxypyrrolin-4-ones of the formula (I) can be boosted significantly through the addition of ammonium salts or phosphonium salts to the application solution or through the incorporation of these salts into a formulation comprising 2-acyloxypyrrolin-4-ones of the formula (I). The present invention therefore provides for the use of ammonium salts or phosphonium salts for boosting the action of crop protection compositions which comprise as their active compound insecticidally and/or acaricidally and/or nematicidally and/or herbicidally active 2-acyloxypyrrolin-4-ones of the formula (I). The invention likewise provides compositions which comprise herbicidally and/or acaricidally and/or insecticidally and/or nematicidally active 2-acyloxypyrrolin-4-ones of the formula (I) and action-boosting ammonium salts or phosphonium salts, including not only formulated active compounds but also ready-to-use compositions (spray liquors). The invention further provides, finally, for the use of these compositions for controlling insect pests and/or spider mites and/or unwanted plant growth.

The compounds of the formula (I) possess a broad insecticidal and/or acaricidal and/or nematicidal and/or herbicidal activity, but individually the activity and/or plant tolerance leaves something to be desired. However, by adding ammonium or phosphonium salts, some or all of these properties can be improved.

The active compounds can be used in the compositions of the invention in a broad concentration range. The concentration of the active compounds in the formulation here is usually 0.1-50% by weight.

Ammonium and phosphonium salts which, according to the invention, boost the activity of crop protection compositions comprising active compounds from the class of the 2-acyloxypyrrolin-4-ones of the formula (I) are defined by formula (III')

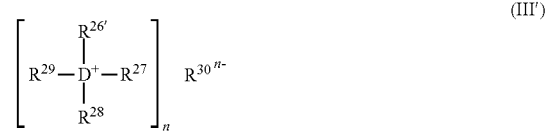

in which
D represents nitrogen or phosphorus,
D preferably represents nitrogen,
$R^{26'}$, $R^{27}$, $R^{28}$ and $R^{29}$ independently of one another represent hydrogen or in each case optionally substituted $C_1$-$C_8$-alkyl or mono- or polyunsaturated, optionally substituted $C_1$-$C_8$-alkylene, where the substituents may be selected from halogen, nitro and cyano,
$R^{26'}$, $R^{27}$, $R^{28}$ and $R^{29}$ independently of one another preferably represent hydrogen or in each case optionally substituted $C_1$-$C_4$-alkyl, where the substituents may be selected from halogen, nitro and cyano,
$R^{26'}$, $R^{27}$, $R^{28}$ and $R^{29}$ independently of one another particularly preferably represent hydrogen, methyl, ethyl, n-propyl, isopropyl, n-butyl, isobutyl, s-butyl or t-butyl,
$R^{26'}$, $R^{27}$, $R^{28}$ and $R^{29}$ very particularly preferably represent hydrogen,
n represents 1, 2, 3 or 4,
n preferably represents 1 or 2,
$R^{30}$ represents an inorganic or organic anion,
$R^{30}$ preferably represents bicarbonate, tetraborate, fluoride, bromide, iodide, chloride, monohydrogenphosphate, dihydrogenphosphate, bisulfate, tartrate, sulfate, nitrate, thiosulfate, thiocyanate, formate, lactate, acetate, propionate, butyrate, pentanoate or oxalate,
$R^{30}$ particularly preferably represents lactate, sulfate, nitrate, thiosulfate, thiocyanate, oxalate or formate.
$R^{30}$ very particularly preferably represents sulfate.

The ammonium salts and phosphonium salts of the formula (III') can be used in a wide concentration range for increasing the effect of crop protection compositions comprising biphenyl-substituted cyclic ketoenoles of the formula (I). In general, the ammonium salts or phosphonium salts are used in the ready-to-use crop protection composition in a concentration of from 0.5 to 80 mmol/l, preferably 0.75 to 37.5 mmol/l, particularly preferably 1.5 to 25 mmol/l. In the case of a formulated product, the concentration of ammonium salt and/or phosphonium salt in the formulation is selected such that it is within these stated general, preferred or particularly preferred ranges following dilution of the formulation to the desired active compound concentration. The concentration of the salt in the formulation here is usually 1-50% by weight.

In one preferred embodiment of the invention, it is not only an ammonium salt and/or phosphonium salt, but additionally a penetrant, that is added to the crop protection compositions to increase the activity. It is considered entirely surprising that even in these cases an even greater boost to activity is observed. Thus, the present invention also provides for the use of a combination of penetrant and ammonium salts and/or phosphonium salts to boost the activity of crop protection compositions which comprise insecticidal and/or acaricidal and/or nematicidal and/or herbicidal 2-acyloxypyrrolin-4-ones of the formula (I) as active compound. The invention likewise provides compositions which comprise herbicidal and/or acaricidal and/or insecticidal and/or nematicidal 2-acyloxypyrrolin-4-ones of the formula (I), penetrants and ammonium salts or phosphonium salts, including not only formulated active compounds but also ready-to-use compositions (spray liquors). The invention further provides, finally, for the use of these compositions for controlling insect pests and/or spider mites and/or unwanted plant growth.

Suitable penetrants in the present context are all those substances which are usually used for improving the penetration of agrochemical active compounds into plants. Penetrants are defined in this context by their ability to penetrate from the aqueous spray liquor and/or from the spray coating into the cuticle of the plant and thereby increase the mobility of active compounds in the cuticle. The method described in the literature (Baur et al., 1997, Pesticide Science 51, 131-152) can be used for determining this property.

Suitable penetrants are, for example, alkanol alkoxylates. Penetrants according to the invention are alkanol alkoxylates of the formula (IV')

R—O—(-AO)$_V$—R'  (IV')

in which
R represents straight-chain or branched alkyl having 4 to 20 carbon atoms,
R' represents hydrogen, methyl, ethyl, n-propyl, isopropyl, n-butyl, isobutyl, tert-butyl, n-pentyl or n-hexyl,
AO represents an ethylene oxide radical, a propylene oxide radical, a butylene oxide radical or represents mixtures of ethylene oxide and propylene oxide radicals or butylene oxide radicals and
V represents a number from 2 to 30.

A preferred group of penetrants are alkanol alkoxylates of the formula

R—O—(-EO—)$_n$—R'  (IV'-a)

in which
R has the meaning given above,
R' has the meaning given above,
EO represents —CH$_2$—CH$_2$—O— and
n represents a number from 2 to 20.

A further preferred group of penetrants are alkanol alkoxylates of the formula

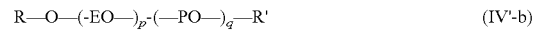

R—O—(-EO—)$_p$-(—PO—)$_q$—R'  (IV'-b)

in which
R has the meaning given above,
R' has the meaning given above,
EO represents —CH$_2$—CH$_2$—O—,
PO represents

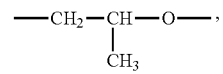

—CH$_2$—CH(CH$_3$)—O—, p represents a number from 1 to 10 and
q represents a number from 1 to 10.

A further preferred group of penetrants are alkanol alkoxylates of the formula

R—O-(—PO—)$_r$-(EO—)$_s$—R'  (IV'-c)

in which
R has the meaning given above,
R' has the meaning given above,
EO represents —CH$_2$—CH$_2$—O—,
PO represents

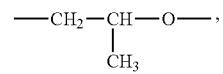

—CH$_2$—CH(CH$_3$)—O—, r represents a number from 1 to 10 and
s represents a number from 1 to 10.

A further preferred group of penetrants are alkanol alkoxylates of the formula

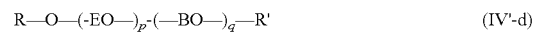

R—O—(-EO—)$_p$-(—BO—)$_q$—R'  (IV'-d)

in which
R and R' have the meanings given above,
EO represents —CH$_2$—CH$_2$—O—,
BO represents

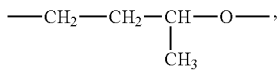

p represents a number from 1 to 10 and
q represents a number from 1 to 10.

A further preferred group of penetrants are alkanol alkoxylates of the formula

R—O—(—BO—)$_r$-(-EO—)$_s$—R'  (IV'-e)

in which
R and R' have the meanings given above,
BO represents

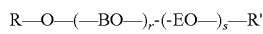

EO represents —CH$_2$—CH$_2$—O—,
r represents a number from 1 to 10 and
s represents a number from 1 to 10.

A further preferred group of penetrants are alkanol alkoxylates of the formula

CH$_3$—(CH$_2$)$_t$—CH$_2$—O—(—CH$_2$—CH$_2$—O—)$_u$—R'  (IV'-f)

in which
R' has the meaning given above,
t represents a number from 8 to 13,
u represents a number from 6 to 17.

In the formulae given above,
R preferably represents butyl, isobutyl, n-pentyl, isopentyl, neopentyl, n-hexyl, isohexyl, n-octyl, isooctyl, 2-ethylhexyl, nonyl, isononyl, decyl, n-dodecyl, isododecyl, lauryl, myristyl, isotridecyl, trimethylnonyl, palmityl, stearyl or eicosyl.

As an example of an alkanol alkoxylate of the formula (IV'-c), mention may be made of 2-ethylhexyl alkoxylate of the formula

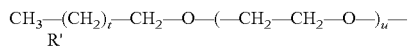
(IV'-c-1)

in which
EO represents —CH$_2$—CH$_2$—O—,
PO represents

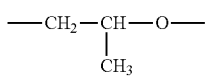

and
the numbers 8 and 6 represent average values.

As an example of an alkanol alkoxylate of the formula (IV'-d), mention may be made of the formula CH$_3$—(CH$_2$)$_{10}$—O—(-EO—)$_6$-(—BO—)$_2$—CH$_3$  (IV'-d-1)

in which
EO represents —CH$_2$—CH$_2$—O—,
BO represents

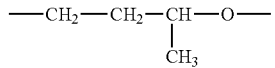

the numbers 10, 6 and 2 represent average values.

Particularly preferred alkanol alkoxylates of the formula (IV'-f) are compounds of this formula in which
t represents a number from 9 to 12 and
u represents a number from 7 to 9.

With very particular preference, mention may be made of alkanol alkoxylate of the formula (IV'-f-1)

CH$_3$—(CH$_2$)$_t$—CH$_2$—O—(—CH$_2$—CH$_2$—O—)$_u$—H  (IV'-f-1)

in which
t represents the average value 10.5 and
u represents the average value 8.4.

The above formulae provide general definitions of the alkanol alkoxylates. These substances are mixtures of substances of the stated type with different chain lengths. The indices are therefore average values which may also deviate from whole numbers.

The alkanol alkoxylates of the stated formulae are known, and some of them are commercially available or can be prepared by known methods (cf. WO 98/35 553, WO 00/35 278 and EP-A 0 681 865).

Suitable penetrants also include, for example, substances which promote the availability of the compounds of the formula (I) in the spray coating. These include, for example, mineral and vegetable oils. Suitable oils are all mineral or vegetable oils—modified or otherwise—which can usually be used in agrochemical compositions. By way of example, mention may be made of sunflower oil, rapeseed oil, olive oil, castor oil, colza oil, corn seed oil, cottonseed oil and soybean oil or the esters of said oils. Preference is given to rapeseed oil, sunflower oil and their methyl or ethyl esters.

The concentration of penetrant in the compositions of the invention can be varied within a wide range. In the case of a formulated crop protection composition, it is generally 1 to 95% by weight, preferably 1 to 55% by weight, particularly preferably 15-40% by weight. In the ready-to-use compositions (spray liquors), the concentrations are generally between 0.1 and 10 g/l, preferably between 0.5 and 5 g/l.

Crop protection compositions of the invention may also comprise further components, examples being surfactants and/or dispersing assistants or emulsifiers.

Suitable nonionic surfactants and/or dispersing assistants include all substances of this type that can typically be used in agrochemical compositions. Preferably mention may be made of polyethylene oxide-polypropylene oxide block copolymers, polyethylene glycol ethers of linear alcohols, reaction products of fatty acids with ethylene oxide and/or propylene oxide, and also polyvinyl alcohol, polyvinylpyrrolidone, copolymers of polyvinyl alcohol and polyvinylpyrrolidone, and copolymers of (meth)acrylic acid and (meth)acrylic esters, and additionally alkyl ethoxylates and alkylaryl ethoxylates, which optionally may be phosphated and optionally may be neutralized with bases, mention being made, by way of example, of sorbitol ethoxylates, and, as well, polyoxyalkylenamine derivatives.

Suitable anionic surfactants include all substances of this type that can typically be used in agrochemical compositions.

Preference is given to alkali metal salts and alkaline earth metal salts of alkylsulfonic acids or alkylarylsulfonic acids.

A further preferred group of anionic surfactants and/or dispersing assistants are the following salts that are of low solubility in plant oil: salts of polystyrenesulfonic acids, salts of polyvinylsulfonic acids, salts of naphthalenesulfonic acid-formaldehyde condensation products, salts of condensation products of naphthalenesulfonic acid, phenolsulfonic acid and formaldehyde, and salts of lignosulfonic acid.

Suitable additives which may be included in the formulations of the invention are emulsifiers, foam inhibitors, preservatives, antioxidants, colorants and inert filling materials.

Preferred emulsifiers are ethoxylated nonylphenols, reaction products of alkylphenols with ethylene oxide and/or propylene oxide, ethoxylated arylalkylphenols, and also ethoxylated and propoxylated arylalkylphenols, and also sulfated or phosphated arylalkyl ethoxylates and/or arylalkyl ethoxypropoxylates, mention being made by way of example of sorbitan derivatives, such as polyethylene oxide-sorbitan fatty acid esters, and sorbitan fatty acid esters.

Using, in accordance with process (Aα), for example 3-[(4-chloro-2,6-dimethyl)phenyl]-1-azaspiro[4,5]decane-2,4-dione and pivaloyl chloride as starting materials, the course of the process according to the invention can be represented by the following reaction scheme:

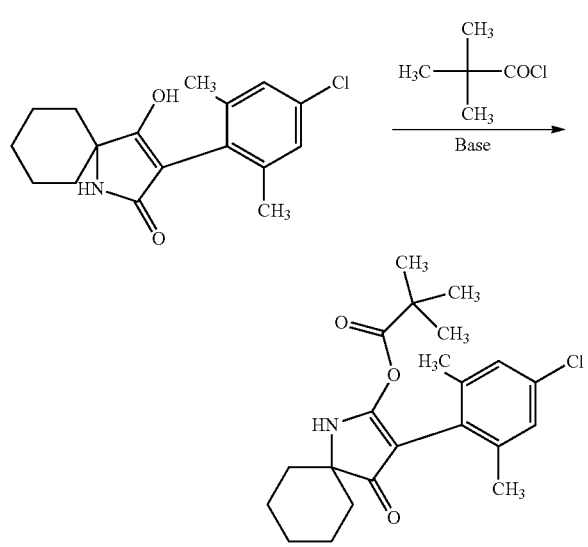

Using, in accordance with process (A), for example 3-[(2,4-dichloro)phenyl]-1-azaspiro-[4,5]-decane-2,4-dione and acetic anhydride as starting materials, the course of the process according to the invention can be represented by the following reaction scheme:

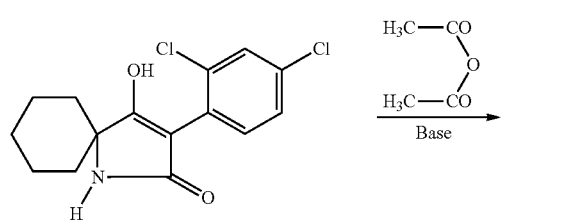

-continued

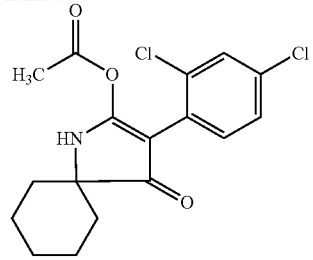

Using, in accordance with process (B), for example 3-[(2,4-dichloro-6-methyl)phenyl]-1-azaspiro[4,5]decane-2,4-dione and ethyl chloroformate as starting materials, the course of the process according to the invention can be represented by the following reaction scheme:

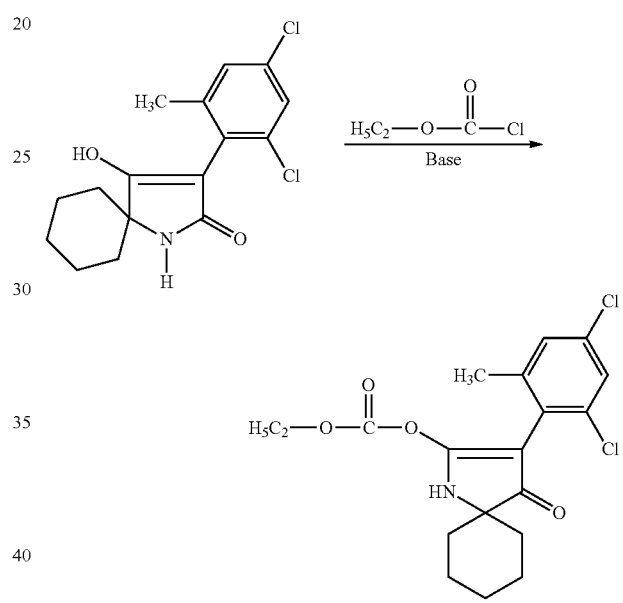

The compounds of the formula (H), required as starting materials in the processes (A) and (B) according to the invention, (II)

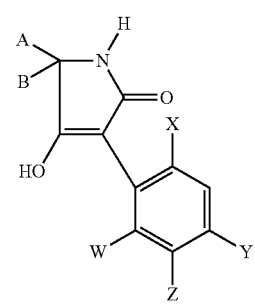

in which

A, B, W, X, Y and Z have the meanings given above, are known in a general manner from the literature cited at the outset, or they can be prepared analogously to the processes described therein.

The acid halides of the formula (III), carboxylic anhydrides of the formula (IV) and chloroformic esters or chloroformic thioesters of the formula (V) required for carrying out the processes (A) and (B) according to the invention are generally known compounds of organic chemistry.

The process ($A_\alpha$) is characterized in that compounds of the formula (II) are in each case reacted with carbonyl halides of the formula (III), if appropriate in the presence of a diluent and if appropriate in the presence of an acid binder.

Suitable diluents for the process ($A_\alpha$) according to the invention are all solvents which are inert to the acid halides. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethylformamide, dimethyl sulfoxide and sulfolane. If the acid halide is sufficiently stable to hydrolysis, the reaction may also be carried out in the presence of water.

Suitable acid binders when carrying out the reaction in accordance with process ($A\alpha$) according to the invention are all customary acid acceptors. The following can preferably be used: tertiary amines such as triethylamine, pyridine, diazabicyclooctane (DABCO), diazabicycloundecene (DBU), diazabicyclononene (DBN), Hünig base and N,N-dimethylaniline, furthermore alkaline earth metal oxides such as magnesium oxide and calcium oxide, moreover alkali metal carbonates and alkaline earth metal carbonates such as sodium carbonate, potassium carbonate and calcium carbonate, and alkali metal hydroxides such as sodium hydroxide and potassium hydroxide.

In the process ($A_\alpha$) according to the invention, the reaction temperature can be varied within a relatively wide range. In general, the process is carried out at temperatures between $-78°$ C. and $+100°$ C., preferably between $-20°$ C. and $100°$ C.

When carrying out the process ($A_\alpha$) according to the invention, the starting materials of the formula (II) and the carbonyl halide of the formula (III) are generally in each case employed in approximately equivalent amounts. However, it is also possible to employ the carbonyl halide in a relatively large excess (of up to 5 mol). Work-up is carried out by customary methods.

The process ($A_\beta$) is characterized in that compounds of the formula (II) are in each case reacted with carboxylic anhydrides of the formula (IV), if appropriate in the presence of a diluent and if appropriate in the presence of an acid binder.

Preferred diluents used for the process ($A_\beta$) according to the invention are those diluents which are also preferred when acid halides are used. Besides, a carboxylic anhydride used in excess may also simultaneously act as diluent.

In the process ($A_\beta$), acid binders which are added, if appropriate, are preferably those acid binders which are also preferred when acid halides are used.

In the process ($A_\beta$) according to the invention, the reaction temperature can be varied within a relatively wide range. In general, the process is carried out at temperatures between $-20°$ C. and $+150°$ C., preferably between $0°$ C. and $100°$ C.

When carrying out the process ($A_\beta$) according to the invention, the starting materials of the formula (II) and the carboxylic anhydride of the formula (IV) are generally in each case employed in approximately equivalent amounts. However, it is also possible to employ the carboxylic anhydride in a relatively large excess (of up to 5 mol). Work-up is carried out by customary methods.

In general, a procedure is followed in which diluent, excess carboxylic anhydride and the carboxylic acid which forms are removed by distillation or by washing with an organic solvent or with water.

The process (B) is characterized in that compounds of the formula (II) are in each case reacted with chloroformic esters or chloroformic thioesters of the formula (V), if appropriate in the presence of a diluent and if appropriate in the presence of an acid binder.

Suitable acid binders for the process (B) according to the invention are all customary acid acceptors. The following can preferably be used: tertiary amines such as triethylamine, pyridine, DABCO, DBU, DBN, Hünig base and N,N-dimethylaniline, furthermore alkaline earth metal oxides such as magnesium oxide and calcium oxide, moreover alkali metal carbonates and alkaline earth metal carbonates such as sodium carbonate, potassium carbonate and calcium carbonate, and alkali metal hydroxides such as sodium hydroxide and potassium hydroxide.

Diluents which can be employed in the process (B) according to the invention are all solvents which are inert to the chloroformic esters or chloroformic thioesters. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, moreover nitriles such as acetonitrile and also strongly polar solvents, such as dimethylformamide, dimethyl sulfoxide and sulfolane.

When carrying out the process (B) according to the invention, the reaction temperature can be varied within a relatively wide range. The reaction temperature is generally between $-78°$ C. and $+100°$ C., preferably between $-20°$ C. and $50°$ C.

Process (B) according to the invention is generally carried out under atmospheric pressure.

When carrying out process (B) according to the invention, the starting materials of the formula (II) and the corresponding chloroformic ester or chloroformic thioester of the formula (V) are generally used in each case in approximately equivalent amounts. However, it is also possible to employ one or the other component in a larger excess (of up to 2 mol). Work-up is carried out by customary methods. In general, a procedure is followed in which the salts which have precipitated are removed and the reaction mixture which remains is concentrated by stripping off the diluent.

The active compounds according to the invention, in combination with good plant tolerance and favorable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They can preferably be used as crop protection compositions. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus* spp., *Aceria sheldoni*, *Aculops* spp., *Aculus* spp., *Amblyomma* spp., *Amphitetranychus viennensis*, *Argas* spp., *Boophilus* spp., *Brevipalpus* spp., *Bryobia praetiosa*, *Chorioptes* spp., *Dermanyssus gallinae*, *Eotetranychus* spp., *Epitrimerus pyri*, *Eutetranychus* spp., *Eriophyes* spp., *Halotydeus destructor*, *Hemitarsonemus* spp., *Hyalomma* spp., *Ixodes* spp., *Latrodectus mactans*, *Metatetranychus* spp., *Nuphersa* spp., *Oligonychus* spp., *Ornithodoros* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Scorpio maurus*, *Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acalymma vittatum*, *Acanthoscelides obtectus*, *Adoretus* spp., *Agelastica alni*, *Agriotes* spp., *Amphimallon solstitialis*, *Anobium punctatum*, *Anoplophora* spp., *Anthonomus* spp., *Anthrenus* spp., *Apion* spp., *Apogonia* spp., *Atomaria* spp., *Attagenus* spp., *Bruchidius obtectus*, *Bruchus* spp., *Cassida* spp., *Cerotoma trifurcata*, *Ceutorrhynchus* spp., *Chaetocnema* spp., *Cleonus mendicus*, *Conoderus* spp., *Cosmopolites* spp., *Costelytra zealandica*, *Ctenicera* spp., *Curculio* spp., *Cryptorhynchus lapathi*, *Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides*, *Hellula undalis*, *Heteronychus arator*, *Heteronyx* spp., *Hylamorpha elegans*, *Hylotrupes bajulus*, *Hypera postica*, *Hypothenemus* spp., *Lachnosterna consanguinea*, *Lema* spp., *Leptinotarsa decemlineata*, *Leucoptera* spp., *Lissorhoptrus oryzophilus*, *Lixus* spp., *Luperodes* spp., *Lyctus* spp., *Megascelis* spp., *Melanotus* spp., *Meligethes aeneus*, *Melolontha* spp., *Migdolus* spp., *Monochamus* spp., *Naupactus xanthographus*, *Niptus hololeucus*, *Oryctes rhinoceros*, *Oryzaephilus surinamensis*, *Oryzaphagus oryzae*, *Otiorrhynchus* spp., *Oxycetonia jucunda*, *Phaedon cochleariae*, *Phyllophaga* spp., *Phyllotreta* spp., *Popillia japonica*, *Premnotrypes* spp., *Psylliodes* spp., *Ptinus* spp., *Rhizobius ventralis*, *Rhizopertha dominica*, *Sitophilus* spp., *Sphenophorus* spp., *Sternechus* spp., *Symphyletes* spp., *Tanymecus* spp., *Tenebrio molitor*, *Tribolium* spp., *Trogoderma* spp., *Tychius* spp., *Xylotrechus* spp., *Zabrus* spp.

From the order of the Collembola, for example, *Onychiurus armatus*.

From the order of the Diplopoda, for example, *Blaniulus guttulatus*.

From the order of the Diptera, for example, *Aedes* spp., *Agromyza* spp., *Anastrepha* spp., *Anopheles* spp., *Asphondylia* spp., *Bactrocera* spp., *Bibio hortulanus*, *Calliphora erythrocephala*, *Ceratitis capitata*, *Chironomus* spp., *Chrysomyia* spp., *Cochliomyia* spp., *Contarinia* spp., *Cordylobia anthropophaga*, *Culex* spp., *Cuterebra* spp., *Dacus oleae*, *Dasyneura* spp., *Delia* spp., *Dermatobia hominis*, *Drosophila* spp., *Echinocnemus* spp., *Fannia* spp., *Gastrophilus* spp., *Hydrellia* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit*, *Pegomyia* spp., *Phorbia* spp., *Prodiplosis* spp., *Psila rosae*, *Rhagoletis* spp., *Stomoxys* spp., *Tabanus* spp., *Tannia* spp., *Tetanops* spp., *Tipula* spp.

From the class of the Gastropoda, for example, *Anion* spp., *Biomphalaria* spp., *Bulinus* spp., *Deroceras* spp., *Galba* spp., *Lymnaea* spp., *Oncomelania* spp., *Pomacea* spp., *Succinea* spp.

From the class of the helminths, for example, *Ancylostoma duodenale*, *Ancylostoma ceylanicum*, *Acylostoma braziliensis*, *Ancylostoma* spp., *Ascaris lubricoides*, *Ascaris* spp., *Brugia malayi*, *Brugia timori*, *Bunostomum* spp., *Chabertia* spp., *Clonorchis* spp., *Cooperia* spp., *Dicrocoelium* spp, *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp., *Strongyloides fuelleborni*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichuria*, *Wuchereria bancrofti*.

It is furthermore possible to control protozoa, such as *Eimeria*.

From the order of the Heteroptera, for example, *Anasa tristis*, *Antestiopsis* spp., *Blissus* spp., *Calocoris* spp., *Campylomma livida*, *Cavelerius* spp., *Cimex* spp., *Collaria* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Monalonion atratum*, *Nezara* spp., *Oebalus* spp., *Pentomidae*, *Piesma quadrata*, *Piezodorus* spp., *Psallus* spp., *Pseudacysta persea*, *Rhodnius* spp., *Sahlbergella singularis*, *Scaptocoris castanea*, *Scotinophora* spp., *Stephanitis nashi*, *Tibraca* spp., *Triatoma* spp.

From the order of the Homoptera, for example, *Acyrthosipon* spp., *Acrogonia* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma pini*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus ribis*, *Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus*, *Ferrisia* spp., *Geococcus coffeae*, *Hieroglyphus* spp., *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva* spp., *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, Sogata spp., Sogatella furcifera, Sogatodes spp., Stictocephala festina, Tenalaphara malayensis, Tinocallis caryaefoliae, Tomaspis spp., Toxoptera spp., Trialeurodes spp., Trioza spp., Typhlocyba spp., Unaspis spp., Viteus vitifolii, Zygina spp.

From the order of the Hymenoptera, for example, Athalia spp., Diprion spp., Hoplocampa spp., Lasius spp., Monomorium pharaonis, Vespa spp.

From the order of the Isopoda, for example, Armadillidium vulgare, Oniscus asellus, Porcellio scaber.

From the order of the Isoptera, for example, Acromyrmex spp., Atta spp., Cornitermes cumulans, Microtermes obesi, Odontotermes spp., Reticulitermes spp.

From the order of the Lepidoptera, for example, Acronicta major, Adoxophyes spp., Aedia leucomelas, Agrotis spp., Alabama spp., Amyelois transitella, Anarsia spp., Anticarsia spp., Argyroploce spp., Barathra brassicae, Borbo cinnara, Bucculatrix thurberiella, Bupalus piniarius, Busseola spp., Cacoecia spp., Caloptilia theivora, Capua reticulana, Carpocapsa pomonella, Carposina niponensis, Chematobia brumata, Chilo spp., Choristoneura spp., Clysia ambiguella, Cnaphalocerus spp., Cnephasia spp., Conopomorpha spp., Conotrachelus spp., Copitarsia spp., Cydia spp., Dalaca noctuides, Diaphania spp., Diatraea saccharalis, Earias spp., Ecdytolopha aurantium, Elasmopalpus lignosellus, Eldana saccharina, Ephestia kuehniella, Epinotia spp., Epiphyas postvittana, Etiella spp., Eulia spp., Eupoecilia ambiguella, Euproctis spp., Euxoa spp., Feltia spp., Galleria mellonella, Gracillaria spp., Grapholitha spp., Hedylepta spp., Helicoverpa spp., Heliothis spp., Hofmannophila pseudospretella, Homoeosoma spp., Homona spp., Hyponomeuta padella, Kakivoria flavofasciata, Laphygma spp., Laspeyresia molesta, Leucinodes orbonalis, Leucoptera spp., Lithocolletis spp., Lithophane antennata, Lobesia spp., Loxagrotis albicosta, Lymantria spp., Lyonetia spp., Malacosoma neustria, Maruca testulalis, Mamestra brassicae, Mocis spp., Mythimna separata, Nymphula spp., Oiketicus spp., Oria spp., Orthaga spp., Ostrinia spp., Oulema oryzae, Panolis flammea, Parnara spp., Pectinophora spp., Perileucoptera spp., Phthorimaea spp., Phyllocnistis citrella, Phyllonorycter spp., Pieris spp., Platynota stultana, Plusia spp., Plutella xylostella, Prays spp., Prodenia spp., Protoparce spp., Pseudaletia spp., Pseudoplusia includens, Pyrausta nubilalis, Rachiplusia nu, Schoenobius spp., Scirpophaga spp., Scotia segetum, Sesamia spp., Sparganothis spp., Spodoptera spp., Stathmopoda spp., Stomopteryx subsecivella, Synanthedon spp., Tecia solanivora, Thermesia gemmatalis, Tinea pellionella, Tineola bisselliella, Tortrix spp., Trichoplusia spp., Tuta absoluta, Virachola spp.

From the order of the Orthoptera, for example, Acheta domesticus, Blatta orientalis, Blattella germanica, Dichroplus spp., Gryllotalpa spp., Leucophaea maderae, Locusta spp., Melanoplus spp., Periplaneta americana, Schistocerca gregaria.

From the order of the Siphonaptera, for example, Ceratophyllus spp., Xenopsylla cheopis.

From the order of the Symphyla, for example, Scutigerella spp.

From the order of the Thysanoptera, for example, Anaphothrips obscurus, Baliothrips biformis, Drepanothris reuteri, Enneothrips flavens, Frankliniella spp., Heliothrips spp., Hercinothrips femoralis, Rhipiphorothrips cruentatus, Scirtothrips spp., Taeniothrips cardamoni, Thrips spp.

From the order of the Thysanura, for example, Lepisma saccharina.

The phytoparasitic nematodes include, for example, Aphelenchoides spp., Bursaphelenchus spp., Ditylenchus spp., Globodera spp., Heterodera spp., Longidorus spp., Meloidogyne spp., Pratylenchus spp., Radopholus similis, Trichodorus spp., Tylenchulus semipenetrans, Xiphinema spp.

The active compounds can be converted into the customary formulations, such as solutions, emulsions, wettable powders, water- and oil-based suspensions, powders, dusts, pastes, soluble powders, soluble granules, granules for broadcasting, suspoemulsion concentrates, natural compounds impregnated with active compound, synthetic substances impregnated with active compound, fertilizers and also microencapsulations in polymeric substances.

These formulations are produced in a known manner, for example by mixing the active compounds with extenders, i.e. liquid solvents, and/or solid carriers, optionally with the use of surfactants, i.e. emulsifiers and/or dispersants, and/or foam formers. The formulations are produced either in suitable production plants or else before or during application.

Suitable for use as auxiliaries are substances which are suitable for imparting to the composition itself and/or to preparations derived therefrom (for example spray liquors, seed dressings) particular properties such as certain technical properties and/or also particular biological properties. Typical auxiliaries include: extenders, solvents and carriers.

Suitable extenders are, for example, water, polar and nonpolar organic chemical liquids, for example from the classes of the aromatic and nonaromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulfones and sulfoxides (such as dimethyl sulfoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulfoxide, and also water.

According to the invention, a carrier is a natural or synthetic, organic or inorganic substance which may be solid or liquid and with which the active compounds are mixed or bonded for better applicability, in particular for application to plants or plant parts. The solid or liquid carrier is generally inert and should be suitable for use in agriculture.

Suitable solid carriers are:
for example ammonium salts and natural rock flours, such as kaolins, clays, talc, chalk, quartz, attapulgite, montmorillonite or diatomaceous earth, and synthetic rock flours, such as finely divided silica, alumina and silicates; useful solid carriers for granules include: for example, crushed and fractionated natural rocks such as calcite, marble, pumice, sepiolite and dolomite, and also synthetic granules of inorganic and organic flours, and granules of organic material such as paper, sawdust, coconut shells, corn cobs and tobacco stalks; useful emulsifiers and/or foam-formers include: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and also protein hydrolysates; suitable dispersants are nonionic and/or ionic substances, for example from the classes of the alcohol-POE and/or -POP ethers, acid and/or POP POE esters, alkylaryl and/or POP POE ethers, fat and/or POP POE adducts, POE- and/or POP-polyol derivatives, POE- and/or POP-sorbitan or -sugar adducts, alkyl or aryl sulfates, alkyl- or arylsulfonates and alkyl or aryl phosphates or the corresponding PO-ether adducts. Furthermore, suitable oligomers or polymers, for example those derived from vinylic monomers, from acrylic acid, from EO and/or PO alone or in combination with, for example, (poly)alcohols or (poly)amines. It is also possible to use lignin and its sulfonic acid derivatives, unmodified and modified celluloses, aromatic and/or aliphatic sulfonic acids and also their adducts with formaldehyde.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

Other possible additives are perfumes, mineral or vegetable oils which are optionally modified, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability, may also be present.

The formulations generally comprise between 0.01 and 98% by weight of active compound, preferably between 0.5 and 90%.

The active compounds according to the invention may be used as such or in formulations thereof, including in a mixture with one or more suitable fungicides, bactericides, acaricides, nematicides, insecticides, microbicides, fertilizers, attractants, sterilants, synergists, safeners, semiochemicals and/or plant growth regulators, in order thus, for example, to broaden the spectrum of action, to prolong the duration of action, to increase the rate of action, to prevent repulsion or prevent evolution of resistance. Furthermore, active compound combinations of this kind can improve plant growth, increase tolerance to high or low temperatures, to drought or to increase levels of water and/or soil salinity, improve flowering performance, facilitate harvesting and increase harvest yields, accelerate ripening, increase the quality and/or nutritional value of the harvested products, prolong storage life and/or improve the processibility of the harvested products. By combining the active compounds according to the invention with mixing partners, synergistic effects are obtained, i.e. the efficacy of the particular mixture is greater than expected on the basis of the efficacies of the individual components. In general, the combinations can be used either as seed treatments or else in premixes, tankmixes or readymixes.

Any additional active compound can be mixed with the active compounds according to the invention within a wide range, preferably in a ratio of 100:1 to 1:100, more preferably of 5:1 to 1:5.

Particularly favourable mixing partners are, for example, the following:

Insecticides/Acaricides/Nematicides:

The active compounds identified here by their common name are known and are described, for example, in the pesticide handbook ("The Pesticide Manual" 14th Ed., British Crop Protection Council 2006) or can be found on the Internet (e.g. http://www.alanwood.net/pesticides).

(1) Acetylcholinesterase (AChE) inhibitors such as, for example, carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos-ethyl, azinphos-methyl, cadusafos, chlorethoxyfos, chlorfenvinphos, chlormephos, chloropyrifos, chloropyrifos-methyl, coumaphos, cyanophos, demeton-5-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl)salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion.

(2) GABA-gated chloride channel antagonists such as, for example, cyclodiene organochlorines, for example chlordane and endosulfan; or phenylpyrazoles (fiproles), for example ethiprole and fipronil.

(3) Sodium channel modulators/voltage-dependent sodium channel blockers such as, for example, pyrethroids, for example acrinathrin, allethrin, d-cis-trans allethrin, d-trans allethrin, bifenthrin, bioallethrin, bioallethrin S-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomers], deltamethrin, empenthrin [(EZ)-(1R) isomers), esfenvalerate, etofenprox, fenpropathrin, fenvalerate, flucythrinate, flumethrin, tau-fluvalinate, halfenprox, imiprothrin, kadethrin, permethrin, phenothrin [(1R)-trans isomer), prallethrin, pyrethrine (pyrethrum), resmethrin, silafluofen, tefluthrin, tetramethrin, tetramethrin [(1R) isomers)], tralomethrin and transfluthrin; or DDT; or methoxychlor.

(4) Nicotinergic acetylcholine receptor (nAChR) agonists such as, for example, neonicotinoids, for example acetamiprid, clothianidin, dinotefuran, imidacloprid, nitenpyram, thiacloprid and thiamethoxam; or nicotine.

(5) Nicotinergic acetylcholine receptor (nAChR) allosteric activators such as, for example, spinosyns, for example spinetoram and spinosad.

(6) Chloride channel activators such as, for example, avermectins/milbemycins, for example abamectin, emamectin benzoate, lepimectin and milbemectin.

(7) Juvenile hormone imitators such as, for example, juvenile hormone analogues, for example hydroprene, kinoprene and methoprene; or fenoxycarb; or pyriproxyfen.

(8) Active compounds with unknown or nonspecific mechanisms of action such as, for example,
alkyl halides, for example methyl bromide and other alkyl halides; or
chloropicrin; or sulfuryl fluoride; or borax; or tartar emetic.
(9) selective antifeedants, for example pymetrozine; or flonicamid;
(10) Mite growth inhibitors, for example clofentezine, hexythiazox and diflovidazin; or etoxazole.
(11) Microbial disruptors of the insect gut membrane, for example *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, and BT plant proteins: Cry1Ab, Cry1Ac, Cry1Fa, Cry2Ab, mCry3A, Cry3Ab, Cry3Bb, Cry34/35Ab1.
(12) Oxidative phosphorylation inhibitors, ATP disruptors such as, for example, diafenthiuron; or
organotin compounds, for example azocyclotin, cyhexatin and fenbutatin oxide; or
propargite; or tetradifon.
(13) Oxidative phosphorylation decouplers acting by interrupting the H proton gradient such as, for example, chlorfenapyr, DNOC and sulfluramid.
(14) Nicotinergic acetylcholine receptor antagonists such as, for example, bensultap, cartap hydrochloride, thiocylam, and thiosultap-sodium.
(15) Chitin biosynthesis inhibitors, type 0, such as, for example, bistrifluoron, chlorfluazuron, diflubenzuron, flucycloxuron, flufenoxuron, hexaflumuron, lufenuron, novaluron, noviflumuron, teflubenzuron and triflumuron.
(16) Chitin biosynthesis inhibitors, type 1, such as, for example, buprofezin.
(17) Molting disruptors, dipteran such as, for example, cyromazine
(18) Ecdysone receptor agonists such as, for example, chromafenozide, halofenozide, methoxyfenozide and tebufenozide.
(19) Octopaminergic agonists such as, for example, amitraz.
(20) Complex-111 electron transport inhibitors such as, for example, hydramethylnone; or acequinocyl; or fluacrypyrim.
(21) Complex-I electron transport inhibitors, for example METI acaricides, for example fenazaquin, fenpyroximate, pyrimidifen, pyridaben, tebufenpyrad and tolfenpyrad; or rotenone (Derris).
(22) Voltage-dependent sodium channel blockers, for example indoxacarb; or metaflumizone.
(23) Inhibitors of acetyl-CoA carboxylase such as, for example,
tetronic and tetramic acid derivatives, for example spirodiclofen, spiromesifen and spirotetramat.
(24) Complex-IV electron transport inhibitors such as, for example,
phosphines, for example aluminum phosphide, calcium phosphide, phosphine and zinc phosphide; or cyanide.
(25) Complex-II electron transport inhibitors such as, for example, cyenopyrafen.
(28) Ryanodine receptor effectors such as, for example,
diamides, for example chlorantraniliprole and flubendiamide.
Further active compounds with unknown mechanism of action, for example amidoflumet, azadirachtin, benclothiaz, benzoximate, bifenazate, bromopropylate, chinomethionat, cryolite, cyantraniliprole (Cyazypyr), cyflumetofen, dicofol, diflovidazin, fluensulfone, flufenerim, flufiprole, fluopyram, fufenozide, imidacloprid, iprodione, pyridalyl, pyrifluquinazon and iodomethane; and additionally preparations based on *Bacillus firmus* (1-1582, BioNeem, Votivo), and the following known active compounds:
3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934), 4-{[(6-bromopyrid-3-yl)methyl](2-fluoroethyl)amino}furan-2(5H)-one (known from WO2007/115644), 4-{[(6-fluoropyrid-3-yl)methyl](2,2-difluoroethyl)amino}furan-2(5H)-one (known from WO2007/115644), 4-{[(2-chloro-1,3-thiazol-5-yl)methyl](2-fluoroethyl)amino}furan-2(5H)-one (known from WO2007/115644), 4-{[(6-chloropyrid-3-yl)methyl](2-fluoroethyl)amino}furan-2(5H)-one (known from WO2007/115644), 4-{[(6-chloropyrid-3-yl)methyl](2,2-difluoroethyl)amino}furan-2(5H)-one (known from WO2007/115644), 4-{[(6-chloro-5-fluoropyrid-3-yl)methyl](methyl)amino}furan-2(5H)-one (known from WO2007/115643), 4-{[(5,6-dichloropyrid-3-yl)methyl](2-fluoroethyl)amino}furan-2(5H)-one (known from WO2007/115646), 4-{[(6-chloro-5-fluoropyrid-3-yl)methyl](cyclopropyl)amino}furan-2(5H)-one (known from WO2007/115643), 4-{[(6-chloropyrid-3-yl)methyl](cyclopropyl)amino}furan-2(5H)-one (known from EP-A-0 539 588), 4-{[(6-chloropyrid-3-yl)methyl](methyl)amino}furan-2(5H)-one (known from EP-A-0 539 588), {[1-(6-chloropyridin-3-yl)ethyl](methyl)oxido-$\lambda^4$-sulfanylidene}cyanamide (known from WO2007/149134) and diastereomers thereof {[(1R)-1-(6-chloropyridin-3-yl)ethyl](methyl)oxido-$\lambda^4$-sulfanylidene}cyanamide (A) and {[(1S)-1-(6-chloropyridin-3-yl) ethyl](methyl)oxido-$\lambda^4$-sulfanylidene}cyanamide (B) (likewise known from WO2007/149134) and sulfoxaflor (also known from WO2007/149134) and diastereomers thereof [(R)-methyl (oxido){(1R)-1-[6-(trifluoromethyl)pyridin-3-yl]ethyl}-$\lambda^4$-sulfanylidene]cyanamide (A1) and [(S)-methyl(oxido){(1S)-1-[6-(trifluoromethyl)pyridin-3-yl]ethyl}-$\lambda^4$-sulfanylidene]cyanamide (A2), designated as diastereomer group A (known from WO 2010/074747, WO 2010/074751), [(R)-methyl (oxido){(1S)-1-[6-(trifluoromethyl)pyridin-3-yl]ethyl}-$\lambda^4$-sulfanylidene]cyanamide (B1) and [(S)-methyl(oxido){(1R)-1-[6-(trifluoromethyl)pyridin-3-yl]ethyl}-$\lambda^4$-sulfanylidene]cyanamide (B2), designated as diastereomer group B (likewise known from WO 2010/074747, WO 2010/074751) and 11-(4-chloro-2,6-dimethylphenyl)-12-hydroxy-1,4-dioxa-9-azadispiro[4.2.4.2]tetradec-11-en-10-one (known from WO2006/089633), 3-(4'-fluoro-2,4-dimethylbiphenyl-3-yl)-4-hydroxy-8-oxa-1-azaspiro[4.5]dec-3-en-2-one (known from WO2008/067911), 1-{2-fluoro-4-methyl-5-[(2,2,2-trifluoroethyl)sulfinyl]phenyl}-3-(trifluoromethyl)-1H-1,2,4-triazol-5-amine (known from WO2006/043635), [(3S,4aR,12R,12aS,12bS)-3-[(cyclopropylcarbonyl)oxy]-6,12-dihydroxy-4,12b-dimethyl-11-oxo-9-(pyridin-3-yl)-1,3,4,4a,5,6,6a,12,12a,12b-decahydro-2H,11H-benzo[f]pyran[4,3-b]chromen-4-yl]methyl cyclopropanecarboxylate (known from WO2008/066153), 2-cyano-3-(difluoromethoxy)-N,N-dimethylbenzenesulfonamide (known from WO2006/056433), 2-cyano-3-(difluoromethoxy)-N-methylbenzenesulfonamide (known from WO2006/100288), 2-cyano-3-(difluoromethoxy)-N-ethylbenzenesulfonamide (known from WO2005/035486), 4-(difluoromethoxy)-N-ethyl-N-methyl-1,2-benzothiazol-3-amine 1,1-dioxide (known from WO2007/057407), N-[1-(2,3-dimethylphenyl)-2-(3,5-dimethylphenyl)ethyl]-4,5-dihydro-1,3-thiazol-2-amine (known from WO2008/104503), {1'-[(2E)-3-(4-chlorophenyl)prop-2-en-1-yl]-5-fluorospiro[indol-3,4'-piperidin]-1 (2H)-yl}(2-chloropyridin-4-yl)methanone (known from WO2003/106457), 3-(2,5-dimethylphenyl)-4-hydroxy-8-methoxy-1,8-diazaspiro[4.5]dec-3-en-2-one (known from WO2009/049851), 3-(2,5-dimethylphenyl)-8- methoxy-2-oxo-1,8-diazaspiro[4.5]dec-3-en-4-yl ethyl carbonate (known from WO2009/049851), 4-(but-2-yn-1-yloxy)-6-(3,5-dimethylpiperidin-1-yl)-5-fluoropyrimidine (known from WO2004/099160), (2,2,3,3,4,4,5,5-octafluoropentyl)(3,3,3-trifluoropropyl)malononitrile (known from WO2005/063094), (2,2,3,3,4,4,5,5-octafluoropentyl)(3,3,4,4,4-pentafluorobutyl)malononitrile (known from WO2005/063094), 8-[2-(cyclopropylmethoxy)-4-(trifluoromethyl)phenoxy]-3-[6-(trifluoromethyl)pyridazin-3-yl]-3-azabicyclo[3.2.1]octane (known from WO2007/040280), 2-ethyl-7-methoxy-3-methyl-6-[(2,2,3,3-tetrafluoro-2,3-dihydro-1,4-benzodioxin-6-yl)oxy]quinolin-4-yl methylcarbonate (known from JP2008/110953), 2-ethyl-7-methoxy-3-methyl-6-[(2,2,3,3-tetrafluoro-2,3-dihydro-1,4-benzodioxin-6-yl)oxy]quinolin-4-yl acetate (known from JP2008/110953), PF1364 (CAS Reg. No. 1204776-60-2) (known from JP2010/018586), 5-[5-(3,5-dichlorophenyl)-5-(trifluoromethyl)-4,5-dihydro-1,2-oxazol-3-yl]-2-(1H-1,2,4-triazol-1-yl)benzonitrile (known from WO2007/075459), 5-[5-(2-chloropyridin-4-yl)-5-(trifluoromethyl)-4,5-dihydro-1,2-oxazol-3-yl]-2-(1H-1,2,4-triazol-1-yl)benzonitrile (known from WO2007/075459), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (known from WO2005/085216), 4-{[(6-chloropyridin-3-yl)methyl](cyclopropyl)amino}-1,3-oxazol-2(5H)-one, 4-{[(6-chloropyridin-3-yl)methyl](2,2-difluoroethyl)amino}-1,3-oxazol-2(5H)-one, 4-{[(6-chloropyridin-3-yl)methyl](ethyl)amino}-1,3-oxazol-2(5H)-one, 4-{[(6-chloropyridin-3-yl)methyl](methyl)amino}-1,3-oxazol-2(5H)-one (all known from WO2010/005692), NNI-0711 (known from WO2002/096882), 1-acetyl-N-[4-(1,1,1,3,3,3-hexafluoro-2-methoxypropan-2-yl)-3-isobutylphenyl]-N-isobutyryl-3,5-dimethyl-1H-pyrazole-4-carboxamide (known from WO2002/096882), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-1,2-diethylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO2005/085216), (5RS,7RS; 5RS,7SR)-1-(6-chloro-3-pyridylmethyl)-1,2,3,5,6,7-hexahydro-7-methyl-8-nitro-5-propoxyimidazo[1,2-a]pyridine (known from WO2007/101369), 2-{6-[2-(5-fluoropyridin-3-yl)-1,3-thiazol-5-yl]pyridin-2-yl}pyrimidine (known from WO2010/006713), 2-{6-[2-(pyridin-3-yl)-1,3-thiazol-5-yl]pyridin-2-yl}pyrimidine (known from WO2010/006713), 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide (known from WO2010/069502), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (known from WO2010/069502), N-[2-(tert-butylcarbamoyl)-4-cyano-6-methylphenyl]-1-(3-chloropyridin-2-yl)-3-{[5-(trifluoromethyl)-1H-tetrazol-1-yl]methyl}-1H-pyrazole-5-carboxamide (known from WO2010/069502), N-[2-(tert-butylcarbamoyl)-4-cyano-6-methylphenyl]-1-(3-chloropyridin-2-yl)-3-{[5-(trifluoromethyl)-2H-tetrazol-2-yl]methyl}-1H-pyrazole-5-carboxamide (known from WO2010/069502) and (1E)-N-[(6-chloropyridin-3-yl)methyl]-N'-cyano-N-(2,2-difluoroethyl)ethanimidamide (known from WO2008/009360).

In a preferred embodiment of the invention, a penetrant is additionally added to the crop protection compositions to enhance the action. Suitable penetrants also include, for example, substances which promote the availability of the compounds of the formula (I) in the spray coating. These include, for example, mineral and vegetable oils. Suitable oils are all mineral or vegetable oils—modified or otherwise—which can usually be used in agrochemical compositions. By way of example, mention may be made of sunflower oil, rapeseed oil, olive oil, castor oil, colza oil, corn seed oil, cottonseed oil and soybean oil or the esters of said oils. Preference is given to rapeseed oil, sunflower oil and their methyl or ethyl esters, especially rapeseed oil methyl ester.

The concentration of penetrant in the compositions of the invention can be varied within a wide range. In the case of a formulated crop protection composition, it is generally 1 to 95% by weight, preferably 1 to 55% by weight, particularly preferably 15-40% by weight. In the ready-to-use compositions (spray liquors), the concentrations are generally between 0.1 and 10 g/l, preferably between 0.5 and 5 g/l.

When used as insecticides, the active compounds according to the invention may also be present in their commercially available formulations and in the use forms, prepared from these formulations, as a mixture with synergists. Synergists are compounds which enhance the action of the active compounds, without any need for the synergist added to be active itself.

When used as insecticides, the active compounds according to the invention can furthermore be present in their commercially available formulations and in the use forms, prepared from these formulations, as a mixture with inhibitors which reduce degradation of the active compound after use in the environment of the plant, on the surface of parts of plants or in plant tissues.

The active compound content of the use forms prepared from the commercially available formulations may vary within wide limits. The active compound concentration of the use forms may be from 0.00000001 to 95% by weight of active compound, preferably between 0.00001 and 1% by weight.

The compounds are employed in a customary manner appropriate for the use forms.

All plants and plant parts can be treated in accordance with the invention. Plants are understood here to mean all plants and plant populations, such as wanted and unwanted wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Examples which may be mentioned are the important crop plants, such as cereals (wheat, rice), corn, soya, potatoes, sugar beet, tomatoes, peas and other vegetable species, cotton, tobacco, oilseed rape and also fruit plants (with the fruits apples, pears, citrus fruits and grapes). Parts of plants are to be understood as meaning all above-ground and below-ground parts and organs of plants, such as shoot, leaf, flower and root, examples which may be mentioned being leaves, needles, stems, trunks, flowers, fruitbodies, fruits and seeds and also roots, tubers and rhizomes. The plant parts also include harvested material and vegetative and generative propagation material, for example cuttings, tubers, rhizomes, slips and seeds.

Treatment according to the invention of the plants and plant parts with the active compounds is carried out directly or by allowing the compounds to act on their surroundings, environment or storage space by the customary treatment methods, for example by immersion, spraying, evaporation, fogging, scattering, painting on, injection and, in the case of propagation material, in particular in the case of seeds, also by applying one or more coats.

As already mentioned above, it is possible to treat all plants and their parts in accordance with the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering, if appropriate in combination with conventional methods (Genetically Modified Organisms), and parts thereof are treated. The terms "parts" or "parts of plants" or "plant parts" have been explained above.

More preferably, plants of the plant cultivars which are commercially available or are in use are treated in accordance with the invention. Plant cultivars are understood to mean plants having new properties ("traits") and which have been obtained by conventional breeding, by mutagenesis or by recombinant DNA techniques. They may be cultivars, biotypes and genotypes.

Depending on the plant species or plant cultivars, and the location and growth conditions (soils, climate, vegetation period, diet) thereof, the inventive treatment may also result in superadditive ("synergistic") effects. For example, possibilities include reduced application rates and/or broadening of the activity spectrum and/or an increase in the activity of the compounds and compositions usable in accordance with the invention, better plant growth, increased tolerance to high or low temperatures, increased tolerance to drought or to levels of water or soil salinity, enhanced flowering performance, easier harvesting, accelerated ripening, higher harvest yields, higher quality and/or higher nutritional value of the harvested products, increased storage life and/or processibility of the harvested products, which exceed the effects normally to be expected.

The active compounds according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example *Pulex* spp., *Ctenocephalides* spp. (*Ctenocephalides canis, Ctenocephalides felis*), *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example *Blatta orientalis, Periplaneta americana, Blattella germanica* and *Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compounds of the formula (I) according to the invention are also suitable for controlling arthropods which attack agricultural livestock, for example cattle, sheep, goats, horses, pigs, donkeys, camels, buffaloes, rabbits, chickens, turkeys, ducks, geese, honey-bees, other domestic animals such as, for example, dogs, cats, caged birds, aquarium fish, and experimental animals, for example hamsters, guinea pigs, rats and mice. The control of these arthropods is intended to reduce cases of death and reduced productivity (of meat, milk, wool, hides, eggs, honey etc.), and so more economic and easier animal husbandry is possible by use of the active compounds according to the invention.

The active compounds according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of molded articles containing the active compound, such as collars, ear marks, tail marks, limb bands, halters, marking devices and the like.

When used for livestock, poultry, domestic animals and the like, the active compounds of the formula (I) can be used as formulations (for example powders, emulsions, flowables) comprising the active compounds in an amount of 1 to 80% by weight, either directly or after 100 to 10 000-fold dilution, or they may be used as a chemical bath.

It has also been found that the compounds according to the invention have strong insecticidal action against insects which destroy industrial materials.

Preferred but nonlimiting examples include the following insects:

beetles, such as *Hylotrupes bajulus, Chlorophorus pilosis, Anobium punctatum, Xestobium rufovillosum, Ptilinus pectinicornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate*

*monachus, Bostrychus capucins, Heterobostrychus brunneus, Sinoxylon* spec. *Dinoderus minutus;*

Dermapterans, such as *Sirex juvencus, Urocerus gigas, Urocerus gigas taignus, Urocerus augur;*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;* bristletails, such as *Lepisma saccarina.*

Industrial materials in the present connection are understood to mean inanimate materials, such as preferably plastics, adhesives, sizes, papers and cards, leather, wood, processed wood products and coating compositions.

The ready-to-use compositions may optionally also comprise other insecticides, and optionally one or more fungicides.

With respect to possible additional partners for mixing, reference is made to the insecticides and fungicides mentioned above.

Moreover, the compounds according to the invention can be employed for protecting objects which come into contact with saltwater or brackish water, in particular hulls, screens, nets, buildings, moorings and signalling systems, against fouling.

Furthermore, the compounds according to the invention can be used alone or in combinations with other active compounds as antifouling compositions.

The active compounds are also suitable for controlling animal pests in the domestic sector, in the hygiene sector and in the protection of stored products, especially insects, arachnids and mites, which are found in enclosed spaces, for example homes, factory halls, offices, vehicle cabins and the like.

They can be used to control these pests alone or in combination with other active compounds and auxiliaries in domestic insecticide products. They are effective against sensitive and resistant species, and against all developmental stages. These pests include:

From the order of the Scorpionidea, for example, *Buthus occitanus.*

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, *Aviculariidae, Araneidae.*

From the order of the *Opiliones,* for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Pemphigus* spp., *Phylloera vastatrix, Phthirus pubis.*

From the order of the Heteroptera, for example, *Cimex hemipterus, Cimex lectularius, Rhodinus prolixus, Triatoma infestans.*

In the field of household insecticides, they are used alone or in combination with other suitable active compounds, such as phosphoric acid esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive evaporation systems, moth papers, moth bags and moth gels, as granules or dusts, in baits for spreading or in bait stations.

The compounds of the formula (I) according to the invention (active compounds) have excellent herbicidal activity against a broad spectrum of economically important mono- and dicotyledonous annual harmful plants. The active compounds act efficiently even on perennial harmful plants which produce shoots from rhizomes, root stocks and other perennial organs and which are difficult to control.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The advantageous effect of the compatibility with crop plants of the active compound combinations according to the invention is particularly pronounced at certain concentration ratios. However, the weight ratios of the active compounds in the active compound combinations can be varied within relatively wide ranges. In general, from 0.001 to 1000 parts by weight, preferably from 0.01 to 100 parts by weight, particularly preferably 0.05 to 20 parts by weight, of one of the compounds (antidotes/safeners) which improves crop plant compatibility mentioned above under (b') are present per part by weight of active compound of the formula (I).

The active compounds according to the invention are generally applied in the form of finished formulations. However, the active compounds contained in the active compound combinations can, as individual formulations, also be mixed during use, i.e. be applied in the form of tank mixes.

For certain applications, in particular by the post-emergence method, it may furthermore be advantageous to include, as further additives in the formulations, mineral or vegetable oils which are tolerated by plants (for example the commercial preparation "Rako Binol"), or ammonium salts, such as, for example, ammonium sulfate or ammonium thiocyanate.

The novel active compound combinations can be used as such, in the form of their formulations or in the use forms prepared therefrom by further dilution, such as ready-to-use solutions, suspensions, emulsions, powders, pastes and granules. They are used in a customary manner, for example by watering, spraying, atomizing, dusting or broadcasting.

The application rates of the active compound combinations according to the invention can be varied within a certain range; they depend, inter alia, on the weather and on soil factors. In general, the application rates are between 0.001 and 5 kg per ha, preferably between 0.005 and 2 kg per ha, particularly preferably between 0.01 and 0.5 kg per ha.

Depending on their properties, the safeners to be used according to the invention can be used for pretreating the seed of the crop plant (seed dressing) or can be introduced into the seed furrows prior to sowing or be used separately prior to the herbicide or together with the herbicide, before or after emergence of the plants.

Examples of plants which may be mentioned are the important crop plants, such as cereals (wheat, barley, rice), corn, soya, potatoes, cotton, oilseed rape, beet, sugar cane and also fruit plants (with the fruits apples, pears, citrus fruits and grapevines), greater emphasis being given to cereals, corn, soya, potatoes, cotton and oilseed rape.

The active compounds according to the invention can be used to treat all plants and parts of plants. Plants are understood here to mean all plants and plant populations, such as wanted and unwanted wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. The plant parts also include harvested material and vegetative and generative propagation material, for example cuttings, tubers, rhizomes, slips and seeds.

Treatment according to the invention of the plants and plant parts with the active compounds is carried out directly or by allowing the compounds to act on their surroundings, environment or storage space by the customary treatment methods, for example by immersion, spraying, evaporation, fogging, scattering, painting on, injection and, in the case of propagation material, in particular in the case of seeds, also by applying one or more coats.

The present invention therefore also relates to a method for controlling unwanted plants or for regulating the growth of plants, preferably in crops of plants, where one or more compound(s) according to the invention is/are applied to the plants (for example harmful plants such as mono- or dicotyledonous weeds or undesired crop plants), to the seeds (for example grains, seeds or vegetative propagules such as tubers or shoot parts with buds) or to the area on which the plants grow (for example the area under cultivation). The compounds according to the invention can be applied, for example, prior to sowing (if appropriate also by incorporation into the soil), prior to emergence or after emergence. Specific examples may be mentioned of some representatives of the mono- and dicotyledonous weed flora which can be controlled by the compounds according to the invention, without the enumeration being restricted to certain species.

Monocotyledonous Harmful Plants of the Genera:
Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.

Dicotyledonous Weeds of the Genera:
Abutilon, Amaranthus, Ambrosia, Anoda, Anthemis, Aphanes, Artemisia, Atriplex, Bettis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.

The plants listed can be treated in accordance with the invention in a particularly advantageous manner with the compounds of the general formula I and/or the active compound mixtures according to the invention. The preferred ranges stated above for the active compounds or mixtures also apply to the treatment of these plants. Particular emphasis is given to the treatment of plants with the compounds or mixtures specifically mentioned in the present text.

If the compounds according to the invention are applied to the soil surface before germination, the weed seedlings are either prevented completely from emerging or else the weeds grow until they have reached the cotyledon stage, but then their growth stops, and, eventually, after three to four weeks have elapsed, they die completely.

If the active compounds are applied post-emergence to the green parts of the plants, growth stops after the treatment, and the harmful plants remain at the growth stage of the point of time of application, or they die completely after a certain time, so that in this manner competition by the weeds, which is harmful to the crop plants, is eliminated very early and in a sustained manner Although the compounds according to the invention display an outstanding herbicidal activity against mono- and dicotyledonous weeds, crop plants of economically important crops, for example dicotyledonous crops of the genera Arachis, Beta, Brassica, Cucumis, Cucurbita, Helianthus, Daucus, Glycine, Gossypium, Ipomoea, Lactuca, Linum, Lycopersicon, Miscanthus, Nicotiana, Phaseolus, Pisum, Solanum, Vicia, or monocotyledonous crops of the genera Allium, Ananas, Asparagus, Avena, Hordeum, Oryza, Panicum, Saccharum, Secale, Sorghum, Triticale, Triticum, Zea, are damaged only to an insignificant extent, or not at all, depending on the structure of the respective compound according to the invention and its application rate. This is why the present compounds are highly suitable for the selective control of unwanted plant growth in plant crops such as agriculturally useful plants or ornamental plants.

Moreover, the compounds according to the invention (depending on their respective structure and the application rate applied) have outstanding growth-regulatory properties in crop plants. They intervene in the plant's own metabolism with a regulatory effect, and can thus be used to control plant constituents and to facilitate harvesting, for example by triggering desiccation and stunted growth. Moreover, they are also suitable for generally controlling and inhibiting unwanted vegetative growth without destroying the plants in the process. Inhibiting vegetative growth plays a major role for many mono- and dicotyledonous crops, since, for example, this can reduce or completely prevent lodging.

As already mentioned above, it is possible to treat all plants and their parts in accordance with the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering, if appropriate in combination with conventional methods (Genetically Modified Organisms), and parts thereof are treated. The terms "parts" or "parts of plants" or "plant parts" have been explained above.

More preferably, plants of the plant cultivars which are commercially available or are in use are treated in accordance with the invention. Plant cultivars are understood to mean plants having new properties ("traits") and which have been obtained by conventional breeding, by mutagenesis or by recombinant DNA techniques. They may be cultivars, biotypes and genotypes.

Depending on the plant species or plant cultivars, and the location and growth conditions (soils, climate, vegetation period, diet) thereof, the inventive treatment may also result in superadditive ("synergistic") effects. For example, possibilities include reduced application rates and/or broadening of the activity spectrum and/or an increase in the activity of the compounds and compositions usable in accordance with the invention, better plant growth, increased tolerance to high or low temperatures, increased tolerance to drought or to levels of water or soil salinity, enhanced flowering performance, easier harvesting, accelerated ripening, higher harvest yields, higher quality and/or higher nutritional value of the harvested products, increased storage life and/or processibility of the harvested products, which exceed the effects normally to be expected.

Owing to their herbicidal and plant growth-regulating properties, the active compounds can also be used to control weed plants in crops of known genetically modified plants or of those yet to be developed. In general, the transgenic plants are notable for special advantageous properties, for example for resistances resistances to certain pesticides, in particular certain herbicides, resistances to plant diseases or organisms that cause plant diseases, such as certain insects, nematodes or microorganisms such as fungi, bacteria or viruses. Other special properties relate, for example, to the harvested material with regard to quantity, quality, storability, composition and specific constituents. For instance, there are known transgenic plants with an elevated starch content or altered starch quality, or with a different fatty acid composition in the harvested material. Further special properties may be tolerance or resistance to abiotic stress factors, for example heat, cold, drought, salinity and ultraviolet radiation. The active compounds can also be used in transgenic plants distinguished by higher yields, for example an improved photosynthesis performance or an improved nutrient uptake.

Preference is given to the use of the inventive compounds of the formula (I) and/or salts thereof in economically important transgenic crops of useful plants and ornamental plants, for example of cereals such as wheat, barley, rye, oats, *sorghum* and millet, rice, cassava and corn, or else crops of sugar beet, cotton, soya, oilseed rape, potatoes, tomatoes, peas and other vegetables.

The compounds of the formula (I) can preferably be used as herbicides in crops of useful plants which are resistant, or have been made resistant by recombinant means, to the phytotoxic effects of the herbicides.

Conventional ways of producing novel plants which have modified properties in comparison to plants which have occurred to date consist, for example, in traditional breeding methods and the generation of mutants. Alternatively, novel plants with altered properties can be generated with the aid of recombinant methods (see, for example, EP 0221044, EP 0131624). For example, there have been many descriptions of:

genetic modifications of crop plants for the purpose of modifying the starch synthesized in the plants (for example WO 92/011376 A, WO 92/014827 A, WO 91/019806 A), transgenic crop plants which are resistant to certain herbicides of the glufosinate type (cf., for example, EP 0242236 A, EP 0242246 A) or of the glyphosate type (WO 92/000377A) or of the sulfonylurea type (EP 0257993 A, U.S. Pat. No. 5,013,659) or to combinations or mixtures of these herbicides through "gene stacking", such as transgenic crop plants, for example corn or soya with the tradename or the designation Optimum™ GAT™ (glyphosate ALS tolerant). Also described were transgenic plants resistant to synthetic auxins (for example 2,4 D) HRAC mode of action Class O and Aryloxy-phenoxy Propionate (fops, HRAC, Class A) (DHT, Dow Agroscience Herbicide Tolerance Trait), transgenic crop plants, for example cotton, which is capable of producing *Bacillus thuringiensis* toxins (Bt toxins), which make the plants resistant to certain pests (EP 0142924 A, EP 0193259 A), transgenic crop plants having a modified fatty acid composition (WO 91/013972 A), genetically modified plants having novel insect resistances based, for example, on the expression of toxins from *Photorhabdus, Xenorhabdus* symbionts from entomopathogenic nematodes and toxins from spiders, scorpions, ants, parasitic wasps, genetically modified crop plants with novel constituents or secondary metabolites, for example novel phytoalexins, which bring about an increased disease resistance (EP 0309862 A, EP 0464461 A), genetically modified plants with reduced photorespiration which feature higher yields and higher stress tolerance (EP 0305398 A), transgenic crop plants which produce pharmaceutically or diagnostically important proteins ("molecular pharming"), transgenic crop plants which are notable for higher yields or better quality, transgenic crop plants distinguished by increased tolerances to abiotic and biotic stress factors, and transgenic crop plants which are notable for a combination, for example, of the above-mentioned novel properties ("gene stacking").

Numerous molecular-biology techniques which can be used to produce novel transgenic plants with modified properties are known in principle; see, for example, I. Potrykus and G. Spangenberg (eds.) Gene Transfer to Plants, Springer Lab Manual (1995), Springer Verlag Berlin, Heidelberg, or Christou, "Trends in Plant Science" 1 (1996) 423-431.

To carry out such recombinant manipulations, nucleic acid molecules which allow mutagenesis or a sequence change by recombination of DNA sequences can be introduced into plasmids. With the aid of standard methods, it is possible, for example, to undertake base exchanges, remove part sequences or add natural or synthetic sequences. For the joining of the DNA fragments to one another, adaptors or linkers can be attached to the fragments; see, for example, Sambrook et al., 1989, Molecular Cloning, A Laboratory Manual, 2nd ed. Cold Spring Harbor Laboratory Press, Cold Spring Harbor, N.Y.; or Winnacker "Gene and Klone", VCH Weinheim 2nd edition 1996.

For example, the generation of plant cells with a reduced activity of a gene product can be achieved by expressing at least one corresponding antisense RNA, a sense RNA for achieving a cosuppression effect or by expressing at least one suitably constructed ribozyme which specifically cleaves transcripts of the abovementioned gene product.

To this end, it is possible to use DNA molecules which encompass the entire coding sequence of a gene product inclusive of any flanking sequences which may be present, and also DNA molecules which only encompass portions of the coding sequence, it being necessary for these portions to be long enough to have an antisense effect in the cells. The use of DNA sequences which have a high degree of homology to the coding sequences of a gene product, but are not completely identical to them, is also possible.

When expressing nucleic acid molecules in plants, the protein synthesized may be localized in any desired compartment of the plant cell. However, to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants can be plants of any desired plant species, i.e. not only monocotyledonous, but also dicotyledonous, plants.

Thus, transgenic plants can be obtained whose properties are altered by overexpression, suppression or inhibition of homologous (=natural) genes or gene sequences or the expression of heterologous (=foreign) genes or gene sequences.

It is preferred to employ the compounds (I) according to the invention in transgenic crops which are resistant to growth regulators such as, for example, 2,4 D, dicamba, or against herbicides which inhibit essential plant enzymes, for example acetyl CoA carboxylases, acetolactate synthases (ALS), EPSP synthases, glutamine synthases (GS) or hydroxyphenylpyruvate dioxygenases (HPPD), or against herbicides from the group of the FOPs, sulfonylureas, glyphosate, glufosinate or benzoylisoxazoles and analogous active compounds, or against any combinations of these active compounds.

Particularly preferably, the compounds according to the invention can be used in transgenic crop plants which are resistant to a combination of glyphosates and glufosinates, glyphosates and sulfonylureas or imidazolinones. The compounds according to the invention can be used with very very particular preference in transgenic crop plants, for example corn or soya with the trade name or the designation Optimum™ GAT™ (glyphosate ALS tolerant). Furthermore and particularly preferably, the compounds according to the invention can be employed in transgenic plants resistant to synthetic auxins (for example 2,4 D) having "HRAC mode of action Class 0" and aryloxyphenoxy propionate (fops) having "HRAC mode of action Class A" (for example DHT, Dow Agroscience Herbicide Tolerance Trait).

When the active compounds according to the invention are used in transgenic crops, effects are frequently observed—in addition to the effects on harmful plants which can be observed in other crops—which are specific for the application in the transgenic crop in question, for example a modified or specifically widened spectrum of weeds which can be controlled, modified application rates which may be employed for application, preferably good combinability with the herbicides to which the transgenic crop is resistant, and an effect on growth and yield of the transgenic crop plants.

The invention therefore also provides for the use of the inventive compounds of the formula (I) as herbicides for control of harmful plants in transgenic crop plants.

The inventive compounds can be used in the form of wettable powders, emulsifiable concentrates, sprayable solutions, dusting products or granules in the customary preparations. The invention therefore also provides herbicidal and plant growth-regulating compositions which comprise the inventive compounds.

The inventive compounds can be formulated in various ways, according to the biological and/or physicochemical parameters required. Examples of possible formulations include: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for broadcasting and soil application, granules (GR) in the form of microgranules, sprayable granules, coated granules and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical Technology], Volume 7, C. Hanser Verlag Munich, 4. ed. 1986; Wade van Valkenburg, "Pesticide Formulations", Marcel Dekker, N.Y., 1973; K. Martens, "Spray Drying" Handbook, 3rd ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd ed., Darland Books, Caldwell N.J., H. v. Olphen, "Introduction to Clay Colloid Chemistry"; 2nd ed., J. Wiley & Sons, N.Y.; C. Marsden, "Solvents Guide"; 2nd ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active Ethylene Oxide Adducts], Wiss. Verlagsgesell, Stuttgart 1976; Winnacker-Küchler, "Chemische Technologie" [Chemical Technology], volume 7, C. Hanser Verlag Munich, 4th ed. 1986.

Based on these formulations, it is also possible to produce combinations with other pesticidally active compounds, such as, for example, insecticides, acaricides, herbicides, fungicides, and also with safeners, fertilizers and/or growth regulators, for example in the form of a finished formulation or as a tank mix.

Active compounds which can be employed in combination with the compounds according to the invention in mixed formulations or in the tank mix are, for example, known active compounds which are based on the inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoen desaturase, photosystem I, photosystem II, protoporphyrinogen oxidase, as are described in, for example, Weed Research 26 (1986) 441-445 or "The Pesticide Manual", 13th edition, The British Crop Protection Council and the Royal Soc. of Chemistry, 2003 and the literature cited therein.

Known herbicides or plant growth regulators which may be mentioned as being suitable for being combined with the compounds according to the invention are, for example, the following active compounds:

acetochlor, acibenzolar, acibenzolar-5-methyl, acifluorfen, acifluorfen-sodium, aclonifen, alachlor, allidochlor, alloxydim, alloxydim-sodium, ametryn, amicarbazone, amidochlor, amidosulfuron, aminopyralid, amitrole, ammonium sulfamate, ancymidol, anilofos, asulam, atrazine, azafenidin, azimsulfuron, aziprotryn, BAH-043, BAS-140H, BAS-693H, BAS-714H, BAS-762H, BAS-776H, BAS-800H, beflubutamid, benazolin, benazolin-ethyl, bencarbazone, benfluralin, benfuresate, bensulide, bensulfuron-methyl, bentazone, benzfendizone, benzobicyclon, benzofenap, benzofluor, benzoylprop, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat chloride, chlornitrofen, chlorophthalim, chlorthal-dimethyl, chlorotoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dimefuron, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat dibromide, dithiopyr, diuron, DNOC, eglinazine-ethyl, endothal, EPTC, esprocarb, ethalfluralin, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]phenyl]ethanesulfonamide, fenoprop, fenoxaprop, fenoxaprop-P, fenoxaprop-ethyl, fenoxaprop-P-ethyl, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, fluorochloridone, fluoroxypyr, fluoroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, L-glufosinate, L-glufosinate-ammonium, glufosinate-ammonium, glyphosate, glyphosate-isopropylammonium, H-9201, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HNPC-9908, HOK-201, HW-02, imazamethabenz, imazamethabenz-methyl, imazamox, imazapic, imazapyr, imazaquin, imazethapyr, imazosulfuron, inabenfide, indanofan, indoleacetic acid (IAA), 4-indol-3-ylbutyric acid (IBA), iodosulfuron, iodosulfuron-methyl-sodium, ioxynil, isocarbamid, isopralin, isoproturon, isouron, isoxaben, isoxachlortole, isoxaflutole, isoxapyrifop, IDH-100, KUH-043, KUH-071, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat chloride, mesosulfuron, mesosulfuron-methyl, mesotrione, methabenzthiazuron, metam, metamifop, metamitron, metazachlor, methazole, methoxyphenone, methyldymron, 1-methylcyclopropene, methyl isothiocyanate, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulfate, monolinuron, monosulfuron, monuron, MT 128, MT-5950, i.e. N-[3-chloro-4-(1-methylethyl)phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolate-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazole, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazole, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron-ethyl, pyrazoxyfen, pyribambenz, pyribambenz-isopropyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, secbumeton, sethoxydim, siduron, simazine, simetryn, SN-106279, sulcotrione, sulfallate (CDEC), sulfentrazone, sulfometuron, sulfometuron-methyl, sulfosate (glyphosate-trimesium), sulfosulfuron, SYN-523, SYP-249, SYP-298, SYP-300, tebutam, tebuthiuron, tecnazene, tefuryltrione, tembotrione, tepraloxydim, terbacil, terbucarb, terbuchlor, terbumeton, terbuthylazine, terbutryn, TH-547, thenylchlor, thiafluamide, thiazafluoron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0166, ZJ-0270, ZJ-0543, or ZJ-0862 and also the following compounds

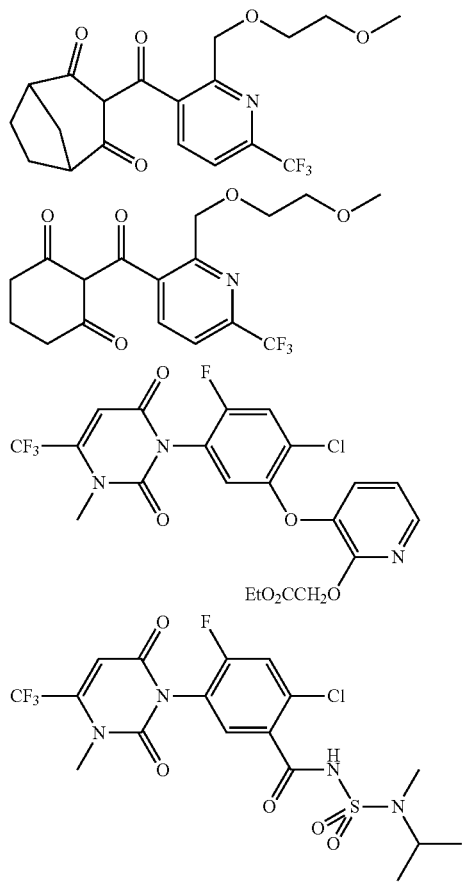

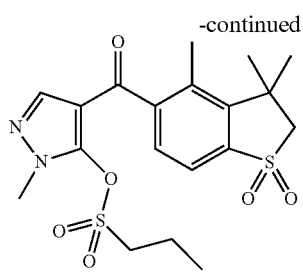

Compounds are referred to either by the "common name" in accordance with the International Organization for Standardization (ISO) or by their chemical name or code number, and in each case include all use forms, such as acids, salts, esters or modifications, such as isomers, stereoisomers and optical isomers. One or else more use forms or modifications are mentioned by way of example.

Wettable powders are preparations which can be dispersed uniformly in water and, as well as the active compound, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurinate. To produce the wettable powders, the herbicidally active compounds are ground finely, for example in customary apparatus such as hammer mills, blower mills and air-jet mills, and simultaneously or subsequently mixed with the formulation assistants.

Emulsifiable concentrates are produced by dissolving the active compound in an organic solvent, for example butanol, cyclohexanone, dimethylformamide, xylene, or else relatively high-boiling aromatics or hydrocarbons or mixtures of the organic solvents, with addition of one or more ionic and/or nonionic surfactants (emulsifiers). The emulsifiers used may be, for example: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusting products are obtained by grinding the active compound with finely distributed solid substances, for example talc, natural clays, such as kaolin, bentonite and pyrophyllite, or diatomaceous earth.

Suspension concentrates may be water- or oil-based. They may be prepared, for example, by wet grinding by means of commercial bead mills and optional addition of surfactants as have, for example, already been listed above for the other formulation types.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be produced either by spraying the active compound onto adsorptive granulated inert material or by applying active compound concentrates by means of adhesives, for example polyvinyl alcohol, sodium polyacrylate or mineral oils, to the surface of carrier substances, such as sand,

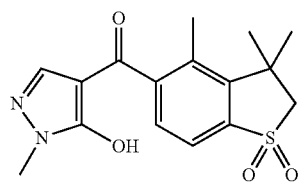

kaolinites or granulated inert material. Suitable active compounds can also be granulated in the manner customary for the production of fertilizer granules—if desired as a mixture with fertilizers.

Water-dispersible granules are prepared generally by the customary processes such as spray-drying, fluidized bed granulation, pan granulation, mixing with high-speed mixers and extrusion without solid inert material.

For the production of pan granules, fluidized bed granules, extruder granules and spray granules, see, for example, processes in "Spray-Drying Handbook" 3rd ed. 1979, G. Goodwin Ltd., London; J. E. Browning, "Agglomeration", Chemical and Engineering 1967, pages 147 ff.; "Perry's Chemical Engineer's Handbook", 5th Ed., McGraw—Hill, New York 1973, pp. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th ed., Blackwell Scientific Publications, Oxford, 1968, pages 101-103.

The agrochemical formulations contain generally 0.1 to 99% by weight, especially 0.1 to 95% by weight, of inventive compounds.

In wettable powders, the active compound concentration is, for example, about 10 to 90% by weight; the remainder to 100% by weight consists of the customary formulation constituents. In emulsifiable concentrates, the active compound concentration may be about 1 to 90% by weight and preferably 5 to 80% by weight. Dust-type formulations contain from 1 to 30% by weight of active compound, preferably usually from 5 to 20% by weight of active compound; sprayable solutions contain from about 0.05 to 80% by weight, preferably from 2 to 50% by weight of active compound. In the case of water-dispersible granules, the active compound content depends partially on whether the active compound is present in liquid or solid form and on which granulation auxiliaries, fillers, etc., are used. In the water-dispersible granules, the content of active compound is, for example, between 1 and 95% by weight, preferably between 10 and 80% by weight.

In addition, the active compound formulations mentioned optionally comprise the respective customary tackifiers, wetting agents, dispersants, emulsifiers, penetrants, preservatives, antifreeze agents and solvents, fillers, carriers and dyes, defoamers, evaporation inhibitors and agents which influence the pH and the viscosity.

The treatment method according to the invention is preferably employed for genetically modified organisms such as, for example, plants or plant parts.

Genetically modified plants, so-called transgenic plants, are plants in which a heterologous gene has been stably integrated into the genome.

The expression "heterologous gene" essentially means a gene which is provided or assembled outside the plant and when introduced in the nuclear, chloroplastic or hypochondrial genome gives the transformed plant new or improved agronomic or other properties by expressing a protein or polypeptide of interest or by downregulating or silencing other gene(s) which are present in the plant (using for example antisense technology, cosuppression technology or RNAi technology [RNA interference]). A heterologous gene that is present in the genome is also called a transgene. A transgene that is defined by its particular location in the plant genome is called a transformation or transgenic event.

Depending on the plant species or plant varieties, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are suitable for mobilizing the defence system of the plant against attack by unwanted phytopathogenic fungi and/or microorganisms and/or viruses. This may, if appropriate, be one of the reasons for the enhanced activity of the combinations according to the invention, for example against fungi. Plant-strengthening (resistance-inducing) substances are to be understood as meaning, in the present context, also those substances or combinations of substances which are capable of stimulating the defence system of plants in such a way that, when subsequently inoculated with unwanted phytopathogenic fungi and/or microorganisms and/or viruses, the treated plants display a substantial degree of resistance to these unwanted phytopathogenic fungi and/or microorganisms and/or viruses. In the present case, unwanted phytopathogenic fungi and/or microorganisms and/or viruses are understood as meaning phytopathogenic fungi, bacteria and viruses. Thus, the substances according to the invention can be employed for protecting plants against attack by the abovementioned pathogens within a certain period of time after the treatment. The period within which protection is achieved generally extends for from 1 to 10 days, preferably 1 to 7 days, after the treatment of the plants with the active compounds.

Plants and plant varieties which are preferably treated according to the invention include all plants which have genetic material which imparts particularly advantageous, useful traits to these plants (whether obtained by breeding and/or biotechnological means).

Plants which are furthermore preferably treated according to the invention are resistant against one or more biotic stress factors, i.e. said plants have a better defence against animal and microbial pests, such as against nematodes, insects, mites, phytopathogenic fungi, bacteria, viruses and/or viroids.

In addition to the plants and plant varieties mentioned above, is also possible to treat those according to the invention which are resistant to one or more abiotic stress factors.

The abiotic stress conditions may include, for example, drought, cold and hot conditions, osmotic stress, waterlogging, elevated soil salinity, elevated exposure to minerals, ozone conditions, strong light conditions, limited availability of nitrogen nutrients, limited availability of phosphorus nutrients or avoidance of shade.

Plants and plant varieties which can likewise be treated in accordance with the invention are those plants which are characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristics of heterosis, or hybrid vigor, which results in generally higher yield, increased vigor, better health and better resistance towards biotic and abiotic stress factors. Such plants are typically made by crossing an inbred male-sterile parent line (the female parent) with another inbred male-fertile parent line (the male parent). Hybrid seed is typically harvested from the male-sterile plants and sold to growers. Male-sterile plants can sometimes (e.g. in corn) be produced by detasseling (i.e. the mechanical removal of the male reproductive organs or male flowers) but, more typically, male sterility is the result of genetic determinants in the plant genome. In that case, and especially when seed is the desired product to be harvested from the hybrid plants, it is typically useful to ensure that male fertility in hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for *Brassica* species. However, genetic determinants for male sterility can also be located in the nuclear genome. Male sterile plants can also be obtained by plant biotechnology methods such as genetic engineering. A particularly useful means for obtaining male-sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar.

Plants or plant varieties (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium*, the CP4 gene of the bacterium *Agrobacterium* sp., the genes encoding a petunia EPSPS, a tomato EPSPS, or an *Eleusine* EPSPS. It can also be a mutated EPSPS. Glyphosate-tolerant plants can also be obtained by expressing a gene that encodes a glyphosate oxidoreductase enzyme. Glyphosate-tolerant plants can also be obtained by expressing a gene that encodes a glyphosate acetyl transferase enzyme. Glyphosate-tolerant plants can also be obtained by selecting plants naturally-occurring mutations of the above-mentioned genes.

Other herbicide-resistant plants are for example plants which have been made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is, for example, an enzyme encoding a phosphinothricin acetyltransferase (such as the bar or pat protein from *Streptomyces* species for example). Plants expressing an exogenous phosphinothricin acetyltransferase have been described.

Further herbicide-tolerant plants are also plants that have been made tolerant to the herbicides inhibiting the enzyme hydroxyphenylpyruvate dioxygenase (HPPD). Hydroxyphenylpyruvate dioxygenases are enzymes that catalyze the reaction in which para-hydroxyphenylpyruvate (HPP) is transformed into homogentisate. Plants tolerant to HPPD inhibitors can be transformed with a gene encoding a naturally occurring resistant HPPD enzyme, or a gene encoding a mutated HPPD enzyme. Tolerance to HPPD inhibitors can also be obtained by transforming plants with genes encoding certain enzymes enabling the formation of homogentisate despite the inhibition of the native HPPD enzyme by the HPPD inhibitor. Tolerance of plants to HPPD inhibitors can also be improved by transforming plants with a gene encoding a prephenate dehydrogenase enzyme in addition to a gene encoding an HPPD-tolerant enzyme.

Further herbicide-resistant plants are plants that have been made tolerant to acetolactate synthase (ALS) inhibitors. Known ALS inhibitors include, for example, sulfonylurea, imidazolinone, triazolopyrimidines, pyrimidinyl oxy(thio)benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides. The production of sulfonylurea-tolerant plants and imidazolinone-tolerant plants is described in international publication WO 1996/033270. Further sulfonylurea- and imidazolinone-tolerant plants are also described, for example in WO 2007/024782.

Further herbicide-resistant plants are plants that have been made tolerant to ACCase inhibitors.

Other plants tolerant to imidazolinone and/or sulfonylurea can be obtained by induced mutagenesis, by selection in cell cultures in the presence of the herbicide or by mutation breeding.

Plants or plant varieties (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

In the present context, the term "insect-resistant transgenic plant" includes any plant containing at least one transgene comprising a coding sequence encoding the following:

1) an insecticidal crystal protein from *Bacillus thuringiensis* or an insecticidal portion thereof, such as the insecticidal crystal proteins described online at: http://www.lifesci.sussex.ac.uk/Home/Neil_Crickmore/Bt/, or insecticidal portions thereof, e.g., proteins of the Cry protein classes Cry1Ab, Cry1Ac, Cry1F, Cry2Ab, Cry3Ae, or Cry3Bb or insecticidal portions thereof; or
2) a crystal protein from *Bacillus thuringiensis* or a portion thereof which is insecticidal in the presence of a second other crystal protein from *Bacillus thuringiensis* or a portion thereof, such as the binary toxin made up of the Cy34 and Cy35 crystal proteins; or 3) a hybrid insecticidal protein comprising portions of two different insecticidal crystal proteins from *Bacillus thuringiensis*, such as a hybrid of the proteins of 1) above or a hybrid of the proteins of 2) above, for example the Cry1A.105 protein produced by corn event MON98034 (WO 2007/027777); or 4) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation, such as the Cry3Bb1 protein in corn events MON863 or MON88017, or the Cry3A protein in corn event MIR604; or 5) an insecticidal secreted protein from *Bacillus thuringiensis* or *Bacillus cereus*, or an insecticidal portion thereof, such as the vegetative insecticidal proteins (VIP) listed at: http://www.lifesci.sussex.ac.uk/Home/Neil_Crickmore/Bt/vip.html, for example proteins from the VIP3Aa protein class; or 6) a secreted protein from *Bacillus thuringiensis* or *Bacillus cereus* which is insecticidal in the presence of a second secreted protein from *Bacillus thuringiensis* oder *B. cereus*, such as the binary toxin made up of the VIP1A and VIP2A proteins.

7) a hybrid insecticidal protein comprising portions from different secreted proteins from *Bacillus thuringiensis* or *Bacillus cereus*, such as a hybrid of the proteins in 1) above or a hybrid of the proteins in 2) above; or 8) a protein of any one of points 1) to 3) above wherein some, particularly 1 to 10, amino acids have been replaced by another amino acid to obtain a higher insecticidal activity to a target insect species, and/or to expand the range of the target insect species affected, and/or because of changes induced in the encoding DNA during cloning or transformation (while still encoding an insecticidal protein), such as the VIP3Aa protein in cotton event COT 102.

Of course, insect-resistant transgenic plants, as used herein, also include any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected or to delay insect resistance development to the plants, by using different proteins insecticidal to the same target insect species but having a different mode of action, such as binding to different receptor binding sites in the insect.

Plants or plant varieties (obtained by plant biotechnology methods such as genetic engineering) which may also be treated according to the invention are tolerant to abiotic stress factors. Such plants can be obtained by genetic transformation, or by selection of plants containing a mutation imparting such stress resistance. Particularly useful stress-tolerant plants include the following:

a. plants which contain a transgene capable of reducing the expression and/or the activity of the poly(ADP-ribose) polymerase (PARP) gene in the plant cells or plants;

b. plants which contain a stress tolerance-enhancing transgene capable of reducing the expression and/or the activity of the PARG encoding genes of the plants or plant cells;

c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase.

Plants or plant varieties (obtained by plant biotechnology methods such as genetic engineering) which may also be treated according to the invention show altered quantity, quality and/or storage stability in the harvested product and/or altered properties of specific components of the harvested product such as, for example:

1) Transgenic plants which synthesize a modified starch, which in its physical-chemical characteristics, in particular the amylose content or the amylose/amylopectin ratio, the degree of branching, the average chain length, the side chain distribution, the viscosity behavior, the gelling strength, the starch grain size and/or the starch grain morphology, is changed in comparison with the synthesized starch in wild-type plant cells or plants, so that this modified starch is better suited for special applications.

2) Transgenic plants which synthesize non-starch carbohydrate polymers or which synthesize non-starch carbohydrate polymers with altered properties in comparison to wild-type plants without genetic modification. Examples are plants which produce polyfructose, especially of the inulin and levan type, plants which produce alpha-1,4-glucans, plants which produce alpha-1,6-branched alpha-1,4-glucans, and plants producing alternan.

3) Transgenic plants which produce hyaluronan.

Plants or plant varieties (obtained by plant biotechnology methods such as genetic engineering) which may also be treated according to the invention are plants, such as cotton plants, with altered fiber characteristics. Such plants can be obtained by genetic transformation, or by selection of plants containing a mutation imparting such altered fiber characteristics and include:

a) plants, such as cotton plants, containing an altered form of cellulose synthase genes;

b) plants, such as cotton plants, containing an altered form of rsw2 or rsw3 homologous nucleic acids;

c) plants, such as cotton plants, with increased expression of sucrose phosphate synthase;

d) plants, such as cotton plants, with increased expression of sucrose synthase;

e) plants, such as cotton plants, wherein the timing of the plasmodesmatal gating at the basis of the fiber cell is altered, e.g. through downregulation of fiber-selective β-1,3-glucanase;

f) plants, such as cotton plants, having fibers with altered reactivity, e.g. through the expression of the N-acetylglucosaminetransferase gene including nodC and chitin synthase genes.

Plants or plant varieties (obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants containing a mutation imparting such altered oil characteristics, and include:

a) plants, such as oilseed rape plants, producing oil having a high oleic acid content;

b) plants, such as oilseed rape plants, which produce oil having a low linolenic acid content;

c) plants, such as oilseed rape plants, producing oil having a low level of saturated fatty acids.

Particularly useful transgenic plants which may be treated according to the invention are plants which comprise one or more genes which encode one or more toxins and are the transgenic plants available under the following trade names: YIELD GARD® (for example corn, cotton, soya beans), KnockOut® (for example corn), BiteGard® (for example corn), BT-Xtra® (for example corn), StarLink® (for example corn), Bollgard® (cotton), Nucotn® (cotton), Nucotn 33B® (cotton), NatureGard® (for example corn), Protecta® and NewLeaf® (potatoes). Examples of herbicide-tolerant plants which may be mentioned are corn varieties, cotton varieties and soybean varieties which are available under the following trade names: Roundup Ready® (glyphosate tolerance, for example corn, cotton, soya bean), Liberty Link® (phosphinotricin tolerance, for example oilseed rape), IMI® (imidazolinone tolerance) and SCS® (sulfonylurea tolerance), for example corn. Herbicide-resistant plants (plants bred in a conventional manner for herbicide tolerance) which should be mentioned include the varieties sold under the Clearfield® name (for example corn).

Particularly useful transgenic plants which may be treated according to the invention are plants containing transformation events, or a combination of transformation events, and that are listed for example in the databases for various national or regional regulatory agencies (see for example http://gmoinfo.jrc.it/gmp_browse.aspx and http://www.ag-bios.com/dbase.php).

The term "active compounds" or "compounds" always also includes the active compound combinations mentioned here.

PREPARATION EXAMPLES

Example I-a-1

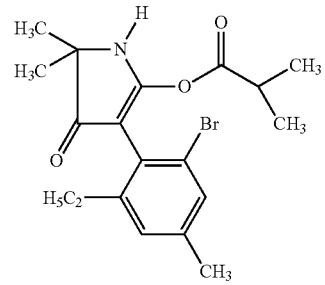

2 g (2.7 mmol) of the compound according to Example I-1-a-6 from WO 07/068,427, together with 0.29 (2.7 mmol) of 2-methylpropionyl chloride, are initially charged in 53 ml of toluene at room temperature. At this temperature, 0.36 g (3.5 mmol) of triethylamine is added dropwise very slowly. The mixture is concentrated and taken up in heptane/ethyl acetate, and the product then precipitates as a solid while the isomeric acylation product remains in solution.

Yield: 0.74 g (70% of theory), m.p. 130° C.

1H-NMR (CDCl$_3$, 400 MHz): 7.25 (d, 1H), 7.00 (d, 1H), 6.55 (sbr, 1H), 2.65 (sept, 1H), 2.50 (q, 2H), 2.30 (s, 3H), 1.25 (s, 3H), 1.20 (s, 3H), 1.17 (d, 3H), 1.15 (d, 3H), 1.10 (tr, 3H) ppm.

13C-NMR (CDCl$_3$, 400 MHz): 198.8 ppm (keto group).

The following compounds of the formula (I-a) are obtained analogously to Example (1-a-1) and following the general preparation instructions

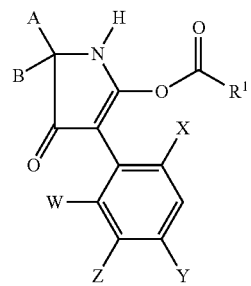

(I-a)

| Ex. No | W | X | Y | Z | A | B | R$^1$ | M.p. ° C. | Isomer |
|---|---|---|---|---|---|---|---|---|---|
| I-a-2 | CH$_3$ | OCH$_3$ | CH$_3$ | H | —(CH$_2$)$_2$—CHOCH$_3$—(CH$_2$)$_2$— | | t-C$_4$H$_9$ | 124* | β |
| I-a-3 | H | C$_2$H$_5$ | Br | H | —(CH$_2$)$_2$—CHCH$_3$—(CH$_2$)$_2$— | | t-C$_4$H$_9$ | * | β |
| I-a-4 | C$_2$H$_5$ | Cl | Cl | H | —(CH$_2$)$_2$—CHCH$_3$—(CH$_2$)$_2$— | | t-C$_4$H$_9$ | * | β |
| I-a-5 | CH$_3$ | C$_2$H$_5$ | Br | H | —(CH$_2$)$_2$—CHOCH$_3$—(CH$_2$)$_2$— | | t-C$_4$H$_9$ | * | β |
| I-a-6 | H | C$_2$H$_5$ | CH$_3$ | H | —(CH$_2$)$_2$—CHCH$_3$—(CH$_2$)$_2$— | | t-C$_4$H$_9$ | * | β |
| I-a-7 | CH$_3$ | C$_2$H$_5$ | Br | H | —(CH$_2$)$_2$—CHCH$_3$—(CH$_2$)$_2$— | | t-C$_4$H$_9$ | * | β |
| I-a-8 | C$_2$H$_5$ | Br | Br | H | —(CH$_2$)$_5$— | | t-C$_4$H$_9$ | 136 | - |
| I-a-9 | C$_2$H$_5$ | OCH$_3$ | Cl | H | —(CH$_2$)$_2$—CHOCH$_3$—(CH$_2$)$_2$— | | t-C$_4$H$_9$ | 146 | β |
| I-a-10 | C$_2$H$_5$ | OCH$_3$ | Cl | H | —(CH$_2$)$_5$— | | t-C$_4$H$_9$ | 204 | |
| I-a-11 | C$_3$H$_7$ | Br | Br | H | CH$_3$ | CH$_3$ | t-C$_4$H$_9$ | * | |
| I-a-12 | C$_2$H$_5$ | OCH$_3$ | Cl | H | —(CH$_2$)$_2$—CHCH$_3$—(CH$_2$)$_2$— | | t-C$_4$H$_9$ | dec. | β |
| I-a-13 | C$_2$H$_5$ | Br | CH$_3$ | H | CH$_3$ | CH$_3$ | t-C$_4$H$_9$ | 150 | |
| I-a-14 | C$_2$H$_5$ | Cl | Br | H | —(CH$_2$)$_5$— | | t-C$_4$H$_9$ | 234 | |
| I-a-15 | C$_2$H$_5$ | OCH$_3$ | Cl | H | —(CH$_2$)$_5$— | | t-C$_4$H$_9$ | 166 | |
| I-a-16 | H | CH$_3$ | H | CH$_3$ | —(CH$_2$)$_2$—CHOCH$_3$—(CH$_2$)$_2$— | | —C(CH$_3$)$_2$C$_2$H$_5$ | * | β |

(I-a-2)
*1H NMR (400 MHz, CDCl$_3$): 6.70 (d, 1H), 6.50 (d, 1H), 3.70 (s, 3H), 3.35 (s, 3H), 3.30 (m, 1H), 2.30 (s, 3H), 2.25 (s, 3H), 1.20 (s, 9H) ppm.
(I-a-3)
*1H NMR (300 MHz, CDCl$_3$): 7.39 (d, 1H), 7.26 (dd, 1H), 6.88 (d, 1H), 6.72 (s broad, 1H), 2.47 (m, 2H), 2.15 (s, 3H), 1.82 (m, 4H), 1.65 (multiple signals broad, 3H), 1.19 (s, 9H), 1.11 (t, 3H), 1.05 (m, 1H), 0.96 (d, 3H), 0.95 (m, 1H) ppm.

-continued

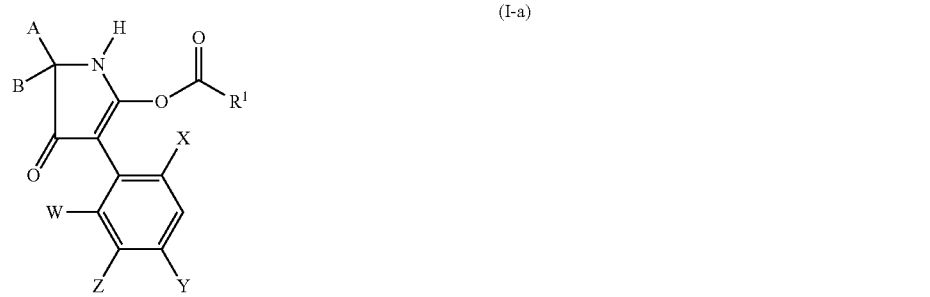

(I-a)

| Ex. No | W | X | Y | Z | A | B | R¹ | M.p. °C. | Isomer |
|---|---|---|---|---|---|---|---|---|---|

(I-a-4)
*1H NMR (300 MHz, CDCl₃): 7.29 (s, 1H), 7.13 (s, 1H), 6.91 (s broad, 1H), 2.56 (q, 2H), 1.92 (m, 4H), 1.60 (multiple signals broad, 3H), 1.19 (s, 9H), 1.09 (t, 3H), 1.07 (m, 1H), 0.97 (d, 3H), 0.87 (m, 1H) ppm.
(I-a-5)
*1H NMR (300 MHz, CDCl₃): 7.18 (s, 2H), 6.82 (s broad, 1H), 3.21 (s, 3H), 3.15 (m ,1H), 2.42 (m, 2H), 2.24 (m, 2H), 2.11 (s, 3H), 1.95 (m, 2H), 1.67 (m, 2H), 1.40 (m, 2H), 1.12 (s, 9H), 1.07 (t, 3H) ppm.
(I-a-6)
*1H NMR (300 MHz, CDCl₃): 7.01 (s, 1H), 6.98 (s, 2H), 6.72 (s broad, 1H), 2.46 (m, 2H), 2.15 (s, 3H), 1.82 (m, 4H), 1.65 (multiple signals broad, 3H), 1.18 (s, 9H), 1.09 (t, 3H), 1.05 (m, 1H), 0.96 (d, 3H), 0.7 (m, 1H) ppm.
(I-a-7)
*1H NMR (300 MHz, CDCl₃): 7.18 (s, 2H), 6.78 (s broad, 1H), 2.43 (m, 2H), 2.11 (s, 3H), 1.92 (m, 4H), 1.60 (multiple signals broad, 3H), 1.13 (s, 9H), 1.07 (t, 3H), 1.05 (m, 2H), 0.97 (d, 3H) ppm.
(I-a-8)
*1H NMR (300 MHz, CDCl₃): 7.60 (d, 1H), 7.30 (d, 1H), 7.00 (sbr, 1H), 2.50 (q, 2H), 2.00-1.50 (m, 8H), 1.50-1.30 (m, 2H), 1.20 (s, 9H), 1.10 (tr, 3H) ppm.
(I-a-9)
*1H NMR (400 MHz, CDCl₃): 6.90 (d, 1H), 6.70 (d, 1H), 3.70 (s, 3H), 3.35 (s, 3H), 3.30 (m, 1H), 2.50 (m, 2H), 1.20 (s, 9H) ppm.
(I-a-10)
*1H NMR (400 MHz, CDCl₃): 6.90 (d, 1H), 6.70 (d, 1H), 3.70 (s, 3H), 2.65 (q, 2H), 2.00-1.30 (m, 10H), 1.30-1.20 (m, 6H) ppm.
(I-a-11)
*1H NMR (400 MHz, CDCl₃): 7.60 (d, 1H), 7.35 (d, 1H), 2.50 (m, 2H), 1.25 (s, 6H), 1.15 (m, 9H) ppm.
(I-a-12)
*1H NMR (300 MHz, CDCl₃): 6.85 (d, 1H), 6.70 (d, 1H), 3.70 (s, 3H), 2.65 (sept, 1H), 2.50 (dq, 2H), 2.00-1.80 (m, 4H), 1.70-1.40 (m, 5H), 1.175 (d, 3H), 1.150 (d, 3H), 1.10 (tr, 3H), 0.95 (d, 3H) ppm.
(I-a-13)
*1H NMR (400 MHz, CDCl₃): 7.30 (d, 1H), 7.05 (d, 1H), 6.55 (sbr, 1H), 2.55 (q, 2H), 2.30 (s, 3H), 1.50 (s, 3H), 1.45 (s, 3H), 1.20 (tr, 3H), 1.10 (s, 9H) ppm.
(I-a-14)
*1H NMR (300 MHz, CDCl₃): 7.40 (d, 1H), 7.30 (d, 1H), 6.95 (sbr, 1H), 2.50 (q, 2H), 2.00-1.60 (m, 8H), 1.50-1.30 (m, 2H), 1.20 (s, 9H), 1.10 (tr, 3H) ppm.
(I-a-16)
*1H-NMR (400 MHz, d₆-DMSO): 0.54 (t, 3H), 1.04 (s, 6H), 1.40-1.57 (m, 6H), 1.65-1.72 (m, 2H), 2.05 (s, 3H), 2.19 (s, 3H), 3.21-3.29 (m + s, 1H +3H), 6.74 (s, 1H), 6.92-6.94 (d, 1H), 7.01-7.03 (d, 1H), 9.05 (sbr, 1H), ppm.

Example (I-b-1)

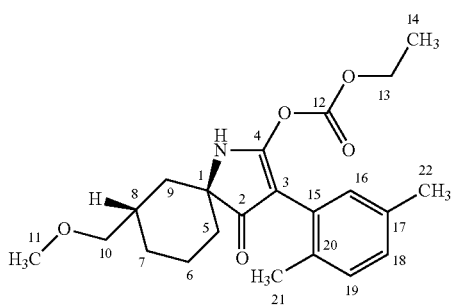

631 mg (2 mmol) of the compound according to Example (I-1-a-6), known from WO 07/048,545, are initially charged in 20 ml of dichloromethane, and 0.28 ml (2 mmol) of triethylamine is added. At 20° C., 0.22 ml (2 mmol) of ethyl chloroformate in 5 ml of dichloromethane is added dropwise, and the mixture is stirred for 1 h. The solvent is evaporated and the residue is chromatographed on silica gel using methylene chloride/ethyl acetate.

Yield 0.3 g (31% of theory) of melting point 238° C.

¹³C-NMR (600 MHz, CDCl₃): δ=14.2 (C-14), 19.7 (C-21), 21.0 (C-22), 22.9 (C-6), 28.9 (C-7), 35.4 (C-5, C-8), 36.9 (C-9), 59.1 (C-11), 67.5 (C-13), 69.1 (C-1), 78.7 (C-10), 100.6 (C-3), 129.2 (C-18), 130.4 (C-15), 130.9 (C-19), 132.0 (C-16), 135.9 (C-17), 136.0 (C-20), 150.5 (C-12), 170.2 (C-4), 200.0 (C-2) ppm.

Also isolated is 0.2 g (20% of theory) of the product Example I-1-c-2, known from WO 07/048,545.

The following compounds of the formula (I-b-1) are obtained analogously to Example (I-b-1) and following the general preparation instructions

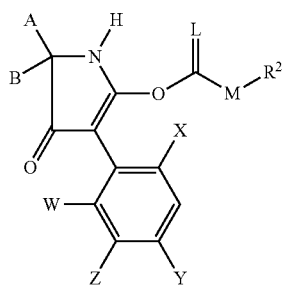

(I-b)

where L = O

| Ex. no. | W | X | Y | Z | A | B | M | R² | M.p. °C | Isomer |
|---|---|---|---|---|---|---|---|---|---|---|
| I-b-2 | $CH_3$ | $C_2H_5$ | J | H | —$(CH_2)_2$—$CHOCH_3$—$(CH_2)_2$— | | O | $C_2H_5$ | * | β |
| I-b-3 | $CH_3$ | $CH_3$ | $CH_3$ | H | —$(CH_2)_2$—CH—$(CH_2)_2$—<br>\|<br>$CH_2OCH_3$ | | O | $C_2H_5$ | 174, * | β |
| I-b-4 | H | $CH_3$ | Cl | $CH_3$ | —$(CH_2)_2$—CH—$(CH_2)_2$—<br>\|<br>$CH_2OCH_3$ | | O | $C_2H_5$ | 66 | β |
| I-b-5 | $C_2H_5$ | $c$-$C_3H_5$ | $CH_3$ | H | $CH_3$ | $CH_3$ | O | $C_2H_5$ | * | — |

I-b-2
* $^1$H-NMR (400 MHz, $CD_3CN$): δ = 1.02 (t, 3H, Ar—$CH_2CH_3$), 1.20 (t, 3H, $OCH_2CH_3$), 1.29-1.44 (m, 2H), 1.66-1.89 (m, 4H), 2.05 (s, 3H, Ar—$CH_3$), 2.36-2.45 (m, 2H), 3.25-3.30 (m, 1H, $CHOCH_3$), 3.32 (s, 3H, $OCH_3$), 4.16-4.21 (q, 2H, $OCH_2CH_3$), 7.05 (s, br, 1H, NH), 7.46 (s, 2H, ArH) ppm.

I-b-3
* $^1$H-NMR (400 MHz, $CD_3CN$): δ = 1.19 (t, 3H, $OCH_2CH_3$), 1.21-1.27 ("dt", 2H), 1.61-1.96 (m, 6H), 2.05 (s, 6H, Ar—$CH_3$), 2.24 (s, 3H, Ar—$CH_3$), 2.87-2.91 (d, 2H), 3.23-3.25 (d, 2H, $CHCH_2O$), 3.29 (s, 3H, $OCH_3$), 6.77 (s, br, 1H, NH), 6.86 (s, 2H, ArH) ppm.

(I-b-5)
* 1H NMR (400 MHz, $CDCl_3$): 6.90 (d, 1H), 6.70 (d, 1H), 6.36 (s, broad, 1H), 4.29 (q, 2H), 2.48 (m, 2H), 2.29 (s, 3H), 1.78 (m, 1H), 1.45 (dd, 6H), 1.32 (t, 3H), 1.11 (dt, 3H), 0.8-0.4 (multiple signals, 4H) ppm.

Example 1

Phaedon Test (PHAECO Spray Treatment)

| Solvents: | 78.0 parts by weight of acetone |
| | 1.5 parts by weight of dimethylformamide |
| Emulsifier: | 0.5 parts by weight of alkylaryl polyglycol ether |

To produce a suitable preparation of active compound, 1 part by weight of active compound is mixed with the stated amount of solvent and emulsifier, and the concentrate is diluted with emulsifier-containing water to the desired concentration. Discs of Chinese cabbage (*Brassica pekinensis*) are sprayed with an active compound preparation of the desired concentration and, after drying, populated with larvae of the mustard beetle (*Phaedon cochleariae*).

After 7 days, the effect in % is determined 100% means that all beetle larvae have been killed; 0% means that none of the beetle larvae have been killed.

In this test, for example, the following compounds of the Preparation Examples show, at an application rate of 500 g/ha, an effect of 83%: Ex. I-a-1, I-a-11, I-a-13, I-b-2

In this test, for example, the following compounds of the Preparation Examples show, at an application rate of 500 g/ha, an effect of 100%: Ex. I-a-2, I-a-14, I-b-1, I-b-3.

Example 2

Spodoptera Frugiperda Test (SPODFR Spray Treatment)

| Solvents: | 78.0 parts by weight of acetone |
| | 1.5 parts by weight of dimethylformamide |
| Emulsifier: | 0.5 parts by weight of alkylaryl polyglycol ether |

To produce a suitable preparation of active compound, 1 part by weight of active compound is mixed with the stated amount of solvent and emulsifier, and the concentrate is diluted with emulsifier-containing water to the desired concentration. Discs of corn leaves (*Zea mays*) are sprayed with an active compound preparation of the desired concentration and, after drying, populated with caterpillars of the armyworm (*Spodoptera frugiperda*).

After 7 days, the effect in % is determined. 100% means that all caterpillars have been killed; 0% means that none of the caterpillars have been killed.

In this test, for example, the following compounds of the Preparation Examples show, at an application rate of 500 g/ha, an effect of 100%: Ex. I-a-2, I-b-3.

Example 3

Myzus Test (MYZUPE Spray Treatment)

| Solvents: | 78 parts by weight of acetone |
| | 1.5 parts by weight of dimethylformamide |
| Emulsifier: | 0.5 parts by weight of alkylaryl polyglycol ether |

To produce a suitable preparation of active compound, 1 part by weight of active compound is mixed with the stated amount of solvent and emulsifier, and the concentrate is diluted with emulsifier-containing water to the desired concentration. Discs of Chinese cabbage (*Brassica pekinensis*) infected by all stages of the green peach aphid (*Myzus persicae*) are sprayed with an active compound preparation of the desired concentration.

After 5 days, the effect in % is determined 100% means that all of the aphids have been killed; 0% means that none of the aphids have been killed.

In this test, for example, the following compounds of the Preparation Examples show, at an application rate of 500 g/ha, an effect of 80%: Ex. I-a-9, I-a-13

In this test, for example, the following compounds of the Preparation Examples show, at an application rate of 500 g/ha, an effect of 90%: Ex. I-a-1, I-a-14, I-b-3, I-b-4

In this test, for example, the following compounds of the Preparation Examples show, at an application rate of 500 g/ha, an effect of 100%: Ex. I-a-2, I-a-16, I-b-1, I-b-2, I-b-5.

Example 4

Tetranychus Test (TETRUR Spray Treatment)

| | |
|---|---|
| Solvents: | 78.0 parts by weight of acetone |
| | 1.5 parts by weight of dimethylformamide |
| Emulsifier: | 0.5 parts by weight of alkylaryl polyglycol ether |

To produce a suitable preparation of active compound, 1 part by weight of active compound is mixed with the stated amount of solvent and emulsifier, and the concentrate is diluted with emulsifier-containing water to the desired concentration. Discs of bean leaves (*Phaseolus vulgaris*) which are infested by all stages of the greenhouse red spider mite (*Tetranychus urticae*) are sprayed with an active compound preparation of the desired concentration.

After 5 days, the effect in % is determined. 100% means that all of the spider mites have been killed; 0% means that none of the spider mites have been killed.

In this test, for example, the following compounds of the Preparation Examples show, at an application rate of 100 g/ha, an effect of 80%: Ex. I-b-2

In this test, for example, the following compounds of the Preparation Examples show, at an application rate of 100 g/ha, an effect of 90%: Ex. I-b-3

In this test, for example, the following compounds of the Preparation Examples show, at an application rate of 100 g/ha, an effect of 100%: Ex. I-b-1

In this test, for example, the following compounds of the Preparation Examples show, at an application rate of 500 g/ha, an effect of 90%: Ex. I-a-14, I-a-16.

Example 5

Nilaparvata Lugens Test (NILALU Hydroponic Treatment)

| | |
|---|---|
| Solvents: | 78.0 parts by weight of acetone |
| | 1.5 parts by weight of dimethylformamide |
| Emulsifier: | 0.5 parts by weight of alkylaryl polyglycol ether |

To produce a suitable preparation of active compound, 1 part by weight of active compound is mixed with the stated amount of solvent and emulsifier, and the concentrate is diluted with emulsifier-containing water to the desired concentration.

The active compound preparation is pipetted into water. The stated concentration refers to the amount of active compound per volume unit of water (mg/l=ppm), the sample is then infected with the brown planthopper (*Nilaparvata lugens*).

After 7 days, the effect in % is determined 100% means that all of the planthoppers have been killed; 0% means that none of the planthoppers have been killed.

In this test, for example, the following compounds of the Preparation Examples show, at an application rate of 20 ppm, an effect of 100%: Ex. I-a-13.

Example 6

Meloidogyne Incognita Test (MELGIN)

| | |
|---|---|
| Solvent: | 80.0 parts by weight of acetone |

To prepare a suitable active compound preparation, 1 part by weight of active compound is mixed with the stated amounts of solvent and the concentrate is diluted with water to the desired concentration.

Containers are filled with sand, solution of active compound, *Meloidogyne incognita* egg/larvae suspension and lettuce seeds. The lettuce seeds germinate and the plants develop. On the roots, galls are formed.

After 14 days, the nematicidal effect in % is determined by the formation of galls. 100% means that no galls have been found; 0% means that the number of galls on the treated plants corresponds to the untreated control.

In this test, for example, the following compounds of the Preparation Examples show, at an application rate of 20 ppm, an effect of 100%: Ex. I-a-2.

Example 7

Boophilus Microplus Test (BOOPMI Injection)

| | |
|---|---|
| Solvent: | dimethyl sulfoxide |

To prepare an appropriate active compound formulation, 10 mg of active compound are mixed with 0.5 ml of solvent and the concentrate is diluted with solvent to the desired concentration. The solution of active compound is injected into the abdomen (*Boophilus microplus*), and the animals are transferred into dishes and kept in a climatized room. The activity is assessed by deposition of fertile eggs.

After 7 days, the effect in % is determined. 100% means that none of the ticks has laid any fertile eggs.

In this test, for example, the following compounds of the Preparation Examples show an efficacy of 80% at an application rate of 20 µg/animal: Ex. I-a-14

In this test, for example, the following compounds of the Preparation Examples show an efficacy of 95% at an application rate of 20 µg/animal: Ex. I-b-1

In this test, for example, the following compounds of the Preparation Examples show an efficacy of 100% at an application rate of 20 µg/animal: Ex. I-b-3.

Example 8

Lucilia Cuprina Test (LUCICU)

| | |
|---|---|
| Solvent: | dimethyl sulfoxide |

To prepare an appropriate active compound formulation, 10 mg of active compound are mixed with 0.5 ml of dimethyl sulfoxide and the concentrate is diluted with water to the desired concentration. Vessels containing horse meat treated with the active compound preparation of the desired concentration are populated with about 20 *Lucilia* cuprina larvae.

After 2 days, the kill in % is determined. 100% means that all of the larvae have been killed; 0% means that none of the larvae have been killed.

In this test, for example, the following compounds of the Preparation Examples show an efficacy of 90% at an application rate of 100 ppm: Ex. I-b-3.

Example 9a

1. Herbicidal Pre-Emergence Action

Seeds of monocotyledonous and dicotyledonous weed plants and crop plants are placed in wood-fiber pots in sandy loam and covered with soil. The test compounds, formulated in the form of wettable powders (WP), are then, as an aqueous suspension with a water application rate of 600 l/ha (converted), with 0.2% of wetting agent added, applied at various dosages to the surface of the covering soil.

After the treatment, the pots are placed in a greenhouse and kept under good growth conditions for the test plants. The visual assessment of the damage to the test plants is carried out after a trial period of about 3 weeks by comparison with untreated controls (herbicidal activity in percent: 100% activity=the plants have died, 0% activity=like control plants).

In addition to the compounds mentioned above, the following compounds show an activity of 90-100% against *Alopecurus myosuroides, Digitaria sanguinalis, Echinocloa crus-galli, Lolium multiflorum, Setaria viridis* and *Sorghum halapense* when applied by the pre-emergence method at 320 g/ha of a.i.: I-a-2, I-a-10, I-a-11, I-a-12.

In addition to the compounds mentioned above, the following compounds show an activity of 90-100% against *Alopecurus myosuroides, Echinocloa crus-galli, Lolium multiflorum* and *Setaria viridis* when applied by the pre-emergence method at 320 g/ha of a.i.: I-a-15, I-b-2, I-b-5.

2. Herbicidal Post-Emergence Action

Seeds of monocotyledonous and dicotyledonous weed and crop plants are placed in sandy loam in wood-fiber pots, covered with soil and cultivated in a greenhouse under good growth conditions. 2 to 3 weeks after sowing, the test plants are treated at the one-leaf stage. The test compounds, formulated as wettable powders (WP), are then, with a water application rate of 600 l/ha (converted), with 0.2% of wetting agent added, sprayed at various dosages onto the green parts of the plants. After the test plants have been kept in the greenhouse under optimum growth conditions for about 3 weeks, the activity of the preparations is rated visually in comparison to untreated controls (herbicidal activity in percent: 100% activity=the plants have died, 0% activity=like control plants).

In addition to the compounds mentioned above, the following compounds show an activity of 90-100% against *Alopecurus myosuroides, Avena fatua, Digitaria sanguinalis, Echinocloa crus-galli, Lolium multiflorum, Setaria viridis* and *Sorghum halapense* when applied by the post-emergence method at 320 g/ha: I-a-2, I-a-4, I-a-5, I-a-7, I-a-9, I-a-10, I-a-11, I-a-12, I-a-13, I-a-15.

In addition to the compounds mentioned above, the following compounds show an activity of 90-100% against *Alopecurus myosuroides, Avena* fatua, *Echinocloa crus-galli, Lolium multiflorum* and *Setaria viridis* when applied by the post-emergence method at 80 g/ha: I-a-1, I-b-2.

Example 9b

Comparative Data

1. Herbicidal Pre-Emergence Action (Pre)

Seeds of monocotyledonous and dicotyledonous weed plants and crop plants are placed in wood-fiber pots in sandy loam and covered with soil. The test compounds, formulated in the form of wettable powders (WP) or emulsion concentrates (EC), are then, as an aqueous suspension with a water application rate of 600-800 l/ha (converted), with 0.1-0.2% of wetting agent added, applied at various dosages to the surface of the covering soil.

After the treatment, the pots are placed in a greenhouse and kept under good growth conditions for the test plants. The visual assessment of the damage to the test plants is carried out after a trial period of about 3 weeks by comparison with untreated controls (herbicidal activity in percent: 100% activity=the plants have died, 0% activity=like control plants).

In this test, for example, the following compounds of the Preparation Examples show superior efficacy to the prior art: see table 2. Herbicidal Post-Emergence Action (Post)

Seeds of monocotyledonous and dicotyledonous weed and crop plants are placed in sandy loam in wood-fiber pots, covered with soil and cultivated in a greenhouse under good growth conditions. 2-3 weeks (stages 10-13 according to the BBCH scale) after sowing, the test plants are treated at a height of 5-10 cm. The test compounds, formulated as wettable powders (WP) or emulsion concentrates (EC), are then, with a water application rate of 600-800 l/ha (converted), with 0.1-0.2% of wetting agent added, sprayed at various dosages onto the green parts of the plants. After the test plants have been kept in the greenhouse under optimum growth conditions for about 3 weeks, the activity of the preparations is rated visually in comparison to untreated controls (herbicidal activity in percent: 100% activity=the plants have died, 0% activity=like control plants).

In this test, for example, the following compounds of the Preparation Examples show superior efficacy to the prior art: see tables

| Active compound | Structure | Test | Concentration | % Activity | | | | | |
|---|---|---|---|---|---|---|---|---|---|
| | | | | AVEFA | LOLMU | SETVI | CHEAL | VIOTR | VERPE |
| I-b-12 known from WO 04/065366 | 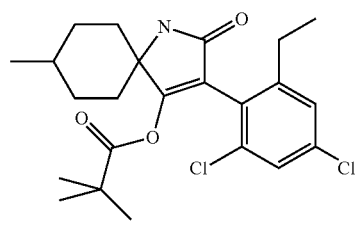 [SMILES: CCc1cc(Cl)cc(Cl)c1C1=C(OC(=O)C(C)(C)C)C2(CCC(C)CC2)NC1=O] | Pre | 320 g/ha | 0 | 40 | 40 | 0 | 0 | 0 |

-continued

| Active compound | Structure | Test | Concentration | % Activity | | | | | |
|---|---|---|---|---|---|---|---|---|---|
| | | | | AVEFA | LOLMU | SETVI | CHEAL | VIOTR | VERPE |
| I-a-4 according to the invention | 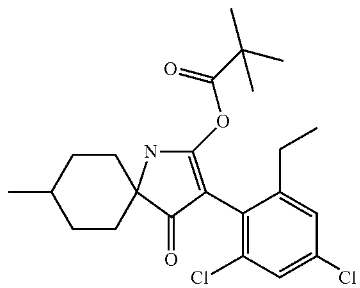 [SMILES: CCc1cc(Cl)cc(Cl)c1C1=C(OC(=O)C(C)(C)C)NC2(CCC(C)CC2)C1=O] | Pre | 320 g/ha | 50 | 100 | 90 | 50 | 70 | 40 |

| Active compound/ structure | Test | Concentration | % Activity | | | | | | | | | | |
|---|---|---|---|---|---|---|---|---|---|---|---|---|---|
| | | | ORYSA | TRZAS | ZEAMX | ALOMY | AVEFA | DIGSA | ECHCG | LOLMU | SETVI | SORHA | VERPE |
| I-b-12 known from WO 04/065366 | Post | 80 g/ha | 0 | 0 | 0 | 0 | 0 | 30 | 40 | 0 | 30 | 0 | 0 |
| I-a-4 according to the invention | Post | 80 g/ha | 100 | 100 | 100 | 100 | 100 | 100 | 100 | 100 | 100 | 100 | 60 |

| Active compound | Structure | Test | Concentration | % Activity ECHCG |
|---|---|---|---|---|
| I-a-5 according to the invention | 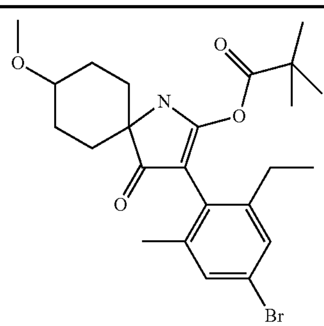 | Post | 20 g/ha | 80 |

-continued

| Active compound | Structure | Test | Concentration | % Activity ECHCG |
|---|---|---|---|---|
| I-b-2 known from WO 05/006125 | 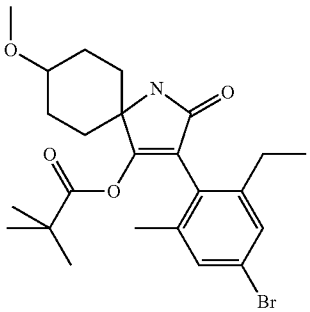 [SMILES: CCc1cc(Br)cc(C)c1C1=C(OC(=O)C(C)(C)C)C2(CCC(OC)CC2)NC1=O] | Post | 20 g/ha | 50 |

| Active compound | Structure | Test | Concentration | % Activity | | | | | |
|---|---|---|---|---|---|---|---|---|---|
| | | | | AVESA | LOLMU | SETVI | AMARE | SINAL | STEME |
| I-a-9 according to the invention | 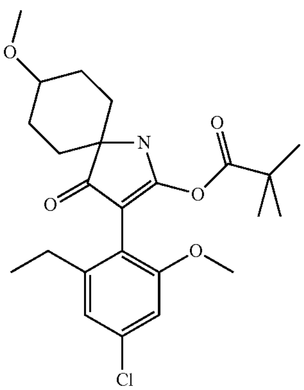 [SMILES: CCc1cc(Cl)cc(OC)c1C1=C(OC(=O)C(C)(C)C)NC2(CCC(OC)CC2)C1=O] | Post | 320 g/ha | 90 | 100 | 100 | 40 | 60 | 40 |
| known from WO 04/080962 | 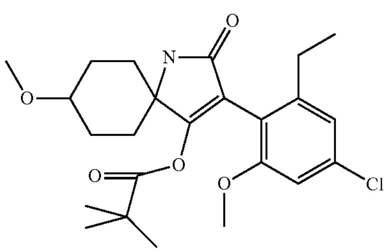 [SMILES: CCc1cc(Cl)cc(OC)c1C1=C(OC(=O)C(C)(C)C)C2(CCC(OC)CC2)NC1=O] | Post | 320 g/ha | 0 | 0 | 0 | 0 | 0 | 0 |

| Active compound | Structure | Test | Concentration | % Activity | | | | | |
|---|---|---|---|---|---|---|---|---|---|
| | | | | ORYSA | TRZAS | ZEAMX | AVEFA | TRZAS | ALOMY | LOLMU |
| known from WO 04/08096 | | Post Post | 80 g/ha 20 g/ha | 0 | 0 | 20 | 20 | 0 | 40 | 50 |

-continued

| Active compound | Structure | Test | Concentration | % Activity ORYSA | TRZAS | ZEAMX | AVEFA | TRZAS | ALOMY | LOLMU |
|---|---|---|---|---|---|---|---|---|---|---|
| I-a-10 according to the invention | 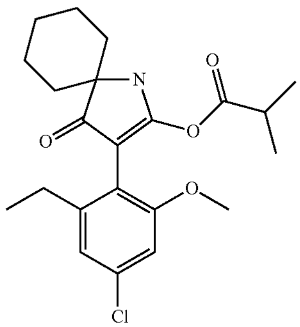 [SMILES: CCc1cc(Cl)cc(OC)c1C1=C(OC(=O)C(C)C)NC2(CCCCC2)C1=O] | Post Post | 80 g/ha 20 g/ha | 60 | 90 | 100 | 100 | 80 | 90 | 100 |

| Active compound/ structure | Test | Concentration | % Activity ORYSA | TRZAS | ZEAMX | ALOMY | AVEFA | DIGSA | ECHCG | LOLMU | SETVI | SORHA | SORHA |
|---|---|---|---|---|---|---|---|---|---|---|---|---|---|
| I-b-41 known from WO 04/065366 | Post | 80 g/ha | 0 | 0 | 0 | 0 | 0 | 0 | 80 | 0 | 0 | 0 | 0 |
| I-a-14 according to the invention | Post | 80 g/ha | 80 | 90 | 100 | 80 | 100 | 100 | 100 | 100 | 100 | 100 | 90 |

| Active compound | Structure | Test | Concentration | % Activity SETVI |
|---|---|---|---|---|
| I-1-c-1 known from WO 06/029799 | 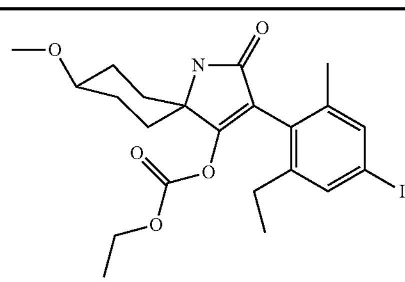 | Pre | 20 g/ha | 20 |

| Active compound | Structure | Test | Concentration | % Activity SETVI |
|---|---|---|---|---|
| I-b-2 according to the invention | 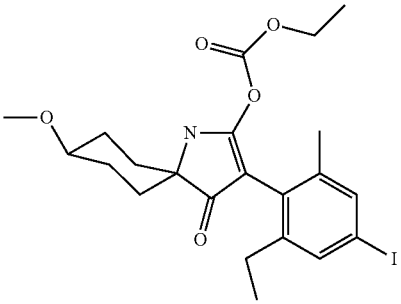 [SMILES: CCOC(=O)OC1=C(c2c(C)cc(I)cc2CC)C(=O)C2(CCC(OC)CC2)N1] | Pre | 20 g/ha | 70 |

| Active compound | Structure | Test | Concentration | % Activity ALOMY | DIGSA | ECHCG |
|---|---|---|---|---|---|---|
| I-1-c-1 known from WO 06/029799 | 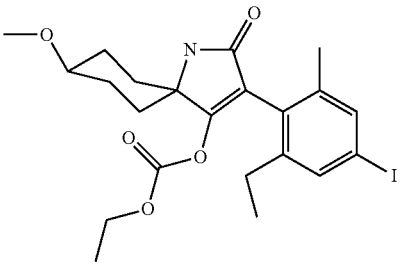 [SMILES: CCOC(=O)OC1=C(c2c(C)cc(I)cc2CC)C(=O)NC12CCC(OC)CC2] | Post | 20 g/ha | 30 | 30 | 30 |
| I-b-2 according to the invention | 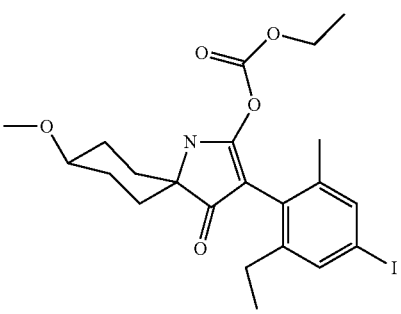 [SMILES: CCOC(=O)OC1=C(c2c(C)cc(I)cc2CC)C(=O)C2(CCC(OC)CC2)N1] | Post | 20 g/ha | 90 | 90 | 70 |

AVEFA: *Avena fatua*
LOLMU: *Lolium multiflorum*
SETVI: *Setaria viridis*
CHEAL: *Chenopodium album*
VIOTR: *Viola tricolor*
VERPE: *Veronica persica*
ORYSA: *Oryza sativa*
TRZAS: *Triticum aestivum*
ZEAMX: *Zea mays*
ALOMY: *Alopecurus myosuroides*
DIGSA: *Digitaria sanguinalis*
ECHCG: *Echinocloa crus-galli*
SORHA: *Sorghum halepense*
AVESA: *Avena sativa*
AMARE: *Amaranthus retroflexus*
SINAL: *Sinapis alba*
STEME: *Stellaria media*

Example 10

Comparative Data

*Phaedon* Test (PHAECO Spray Treatment)

| Solvents: | 78.0 parts by weight of acetone |
|---|---|
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amount of solvent and emulsifier, and the concentrate is diluted with emulsifier-containing water to the desired concentration.

Discs of Chinese cabbage (*Brassica pekinensis*) are sprayed with an active compound preparation of the desired concentration and, after drying, populated with larvae of the mustard beetle (*Phaedon cochleariae*).

After the desired period of time, the activity in % is determined. 100% means that all beetle larvae have been killed; 0% means that none of the beetle larvae have been killed.

In this test, for example, the following compounds of the Preparation Examples show superior efficacy to the prior art: see table

*Myzus* Test (MYZUPE Spray Treatment)

| Solvents: | 78.0 | parts by weight of acetone |
| --- | --- | --- |
|  | 1.5 | parts by weight of dimethylformamide |
| Emulsifier: | 0.5 | part by weight of alkylaryl polyglycol ether |

To produce a suitable preparation of active compound, 1 part by weight of active compound is mixed with the stated amount of solvent and emulsifier, and the concentrate is diluted with emulsifier-containing water to the desired concentration.

Discs of Chinese cabbage (*Brassica pekinensis*) infected by all stages of the green peach aphid (*Myzus persicae*) are sprayed with an active compound preparation of the desired concentration.

After the desired period of time, the activity in % is determined. 100% means that all of the aphids have been killed; 0% means that none of the aphids have been killed.

In this test, for example, the following compounds of the Preparation Examples show superior efficacy to the prior art: see table

*Tetranychus* Test, OP-Resistant (TETRUR Spray Treatment)

| Solvents: | 78.0 parts by weight of acetone |
| --- | --- |
|  | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amount of solvent and emulsifier, and the concentrate is diluted with emulsifier-containing water to the desired concentration.

Discs of bean leaves (*Phaseolus vulgaris*) which are infested by all stages of the greenhouse red spider mite (*Tetranychus urticae*) are sprayed with an active compound preparation of the desired concentration.

After the desired period of time, the activity in % is determined. 100% means that all of the spider mites have been killed; 0% means that none of the spider mites have been killed.

In this test, for example, the following compounds of the Preparation Examples show superior efficacy to the prior art: see table

| Substance | Structure | Object | Concentration | % Activity dat |
| --- | --- | --- | --- | --- |
| known from WO 98/05638 and WO 04/007448 | *(structure)* | MYZUPE<br>TETRUR | 20 g/ha<br>500 g/ha | 0 5dat<br>0 5dat |
| I-a-16 according to the invention | *(structure)* | MYZUPE<br>TETRUR | 20 g/ha<br>500 g/ha | 100 5dat<br>90 5dat |
| I-1-c-2 known from WO 07/048545 | *(structure)* | PHAECO<br>MYZUPE | 100 g/ha<br>4 g/ha | 50 7dat<br>0 5dat |

| Substance | Structure | Object | Concentration | % Activity dat |
|---|---|---|---|---|
| I-b-1 according to the invention | (structure) | PHAECO<br>MYZUPE | 100 g/ha<br>4 g/ha | 100 7dat<br>90 5dat |

*Spodoptera Frugiperda* Test (SPODFR Spray Treatment)

| Solvents: | 78.0 parts by weight of acetone |
|---|---|
|  | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amount of solvent and emulsifier, and the concentrate is diluted with emulsifier-containing water to the desired concentration.

Discs of corn leaves (*Zea mays*) are sprayed with an active compound preparation of the desired concentration and, after drying, populated with caterpillars of the armyworm (*Spodoptera frugiperda*).

After the desired period of time, the activity in % is determined. 100% means that all caterpillars have been killed; 0% means that none of the caterpillars have been killed.

In this test, for example, the following compounds of the Preparation Examples show superior efficacy to the prior art: see table

*Tetranychus* Test, OP-Resistant (TETRUR Spray Treatment)

| Solvents: | 78.0 parts by weight of acetone |
|---|---|
|  | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amount of solvent and emulsifier, and the concentrate is diluted with emulsifier-containing water to the desired concentration.

Discs of bean leaves (*Phaseolus vulgaris*) which are infested by all stages of the greenhouse red spider mite (*Tetranychus urticae*) are sprayed with an active compound preparation of the desired concentration.

After the desired period of time, the activity in % is determined. 100% means that all of the spider mites have been killed; 0% means that none of the spider mites have been killed.

In this test, for example, the following compounds of the Preparation Examples show superior efficacy to the prior art: see table

*Liriomyza Trifolii*-Spray Test (LIRITR)

| Solvents: | 52.5 parts by weight of acetone |
|---|---|
|  | 7 parts by weight of dimethylformamide |
| Emulsifier: | 0.5 part by weight of alkylaryl polyglycol ether |

To produce a suitable preparation of active compound, 1 part by weight of active compound is mixed with the stated amount of solvent and emulsifier, and the concentrate is diluted with emulsifier-containing water to the desired concentration. If the addition of ammonium salts or/and penetrants is required, these are in each case added in a concentration of 1000 ppm to the solution of the preparations.

Discs of bean leaves (*Phaseolus vulgaris*) which are infested by all stages of the leaf-mining fly (*Liriomyza trifolii*) are sprayed with an active compound preparation of the desired concentration.

After the desired period of time, the activity in % is determined. 100% means that all of the leaf-mining flies have been killed; 0% means that none of the leaf-mining flies have been killed.

In this test, for example, the following compounds of the Preparation Examples show superior efficacy to the prior art: see table

*Bemisia Tabaci*—Spray Test (BEMITA)

| Solvents: | 52.5 parts by weight of acetone |
|---|---|
|  | 7 parts by weight of dimethylformamide |
| Emulsifier: | 0.5 part by weight of alkylaryl polyglycol ether |

To produce a suitable preparation of active compound, 1 part by weight of active compound is mixed with the stated amount of solvent and emulsifier, and the concentrate is diluted with emulsifier-containing water to the desired concentration.

Discs of cotton leaves (*Gossypium hirsutum*) which are infested by all stages of the whitefly (*Bemisia tabaci*) are sprayed with an active compound preparation of the desired concentration. After the desired period of time, the activity in % is determined. 100% means that all the whiteflies have been killed; 0% means that none of the whiteflies have been killed.

In this test, for example, the following compounds of the Preparation Examples show superior efficacy to the prior art: see table

*Myzus Persicae* Test (MYZUPE Tau)

| Solvent: | 7 parts by weight of dimethylformamide |
| --- | --- |
| Emulsifier: | 2 parts by weight of alkylaryl polyglycol ether |

To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) which are heavily infested by the green peach aphid (*Myzus persicae*) are treated by dipping into the active compound preparation of the desired concentration. After the desired period of time, the kill in % is determined. 100% means that all of the aphids have been killed; 0% means that none of the aphids have been killed.

In this test, for example, the following compounds of the Preparation Examples show superior efficacy to the prior art: see table

*Myzus Persicae* Test; Hydroponic Treatment (MYZUPE Sys)

| Solvent: | 7 parts by weight of dimethylformamide |
| --- | --- |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

The active compound preparation is mixed with water. The stated concentration refers to the amount of active compound per volume unit of water (mg/l=ppm). The treated water is filled into vessels containing a pea plant (*Pisum sativum*), and the plant is the infested with the green peach aphid (*Myzus persicae*).

After the desired period of time, the kill in % is determined 100% means that all of the aphids have been killed; 0% means that none of the aphids have been killed.

In this test, for example, the following compounds of the Preparation Examples show superior efficacy to the prior art: see table

| Substance | Structure | Object | Concentration | % Activity dat |
| --- | --- | --- | --- | --- |
| I-1-c-16 known from WO 07/048545 | 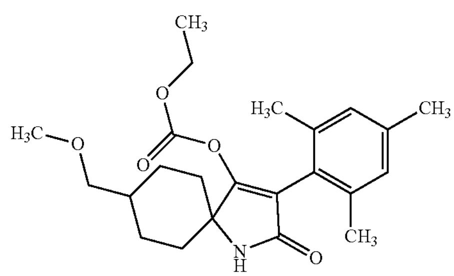 | TETRUR<br>SPODFR<br>BEMITA<br>LIRITRI | 20 g/ha<br>500 g/ha<br>20 g/ha<br>20 g/ha | 0 5dat<br>67 7dat<br>27 7dat<br>0 7dat |
| I-b-3 according to the invention | 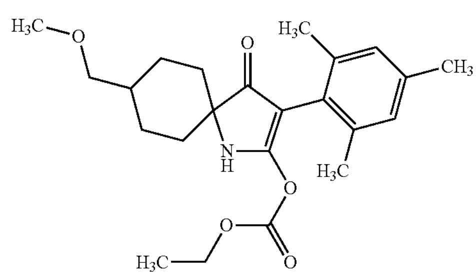 | TETRUR<br>SPODFR<br>BEMITA<br>LIRITRI | 20 g/ha<br>500 g/ha<br>20 g/ha<br>20 g/ha | 80 5dat<br>100 7dat<br>72 7dat<br>80 7dat |
| I-1-c-1 known from WO 06/029799 | 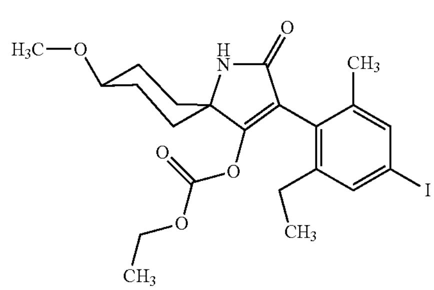 [SMILES: CCOC(=O)OC1=C(c2c(C)cc(I)cc2CC)C(=O)NC12CCC(OC)CC2] | MYZUPE tau<br>MYZUPE sys | 20 ppm<br>20 ppm | 50 6dat<br>60 6dat |

-continued

| Substance | Structure | Object | Concentration | % Activity dat |
|---|---|---|---|---|
| I-b-2 according to the invention | 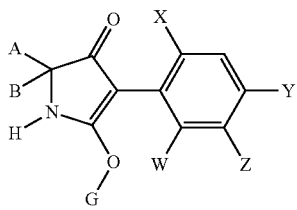 | MYZUPE tau<br>MYZUPE sys | 20 ppm<br>20 ppm | 90 6dat<br>99 6dat |

The invention claimed is:

1. A compound of formula (I)

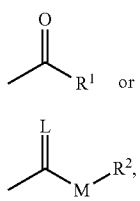

in which

W represents hydrogen or $C_1$-$C_6$-alkyl,

X represents halogen, $C_1$-$C_6$-alkyl, or $C_1$-$C_6$-alkoxy,

Y and Z independently of one another represent hydrogen, $C_1$-$C_6$-alkyl, or halogen, A represents $C_1$-$C_6$-alkyl, B represents $C_1$-$C_6$-alkyl, with the proviso that A and B may each represent methyl only if, in the case of W, X and Y each representing alkyl and Z representing hydrogen, W and X must each represent methyl or must each represent ethyl, or A and B together with the carbon atom to which they are attached represent $C_6$-cycloalkyl which is optionally substituted by methyl, methoxy or methoxymethyl, and G represents one of the groups

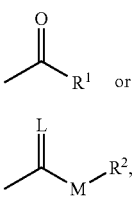

in which

L represents oxygen,

M represents oxygen, $R^1$ represents $C_1$-$C_6$-alkyl, and $R^2$ represents $C_1$-$C_6$-alkyl.

2. The compound of formula (I) as claimed in claim 1, in which

W represents methyl, ethyl or propyl,

X represents methyl, ethyl, chlorine, bromine or methoxy,

Y represents methyl, chlorine, iodine or bromine,

Z represents hydrogen,

A represents methyl,

B represents methyl, with the proviso that in the case of W, X and Y each representing methyl or ethyl, W and X must each represent methyl or must each represent ethyl, or A, B and the carbon to which they are attached represent $C_6$-cycloalkyl which is optionally substituted by methyl, methoxy or methoxymethyl in the 4-position of the cycle, and G represents one of the groups (a)

(b)

in which $R^1$ represents methyl, ethyl, propyl, isopropyl, butyl, isobutyl, sec-butyl or tert-butyl, and $R^2$ represents methyl, ethyl, propyl, isopropyl, butyl, isobutyl, sec-butyl or tert-butyl.

3. The compound of formula (I) as claimed in claim 1, in which

W represents hydrogen,

X represents methyl,

Y represents hydrogen,

Z represents methyl,

A, B and the carbon to which they are attached represent $C_6$-cycloalkyl which is optionally substituted by methoxy or methoxymethyl in the 3- or 4-position, G represents one of the groups

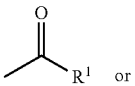

-continued

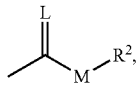
(b)

in which
R¹ represents methyl, ethyl, propyl, isopropyl, butyl, isobutyl, sec-butyl or tert-butyl, and
R² represents methyl, ethyl, propyl, isopropyl, butyl, isobutyl, sec-butyl or tert-butyl.

4. A pesticide and/or herbicide comprising at least one compound of the formula (I) as claimed in claim 1 and an extender and/or a surfactant.

5. A method of controlling animal pests and/or unwanted vegetation, comprising applying a compound of the formula (I) as claimed in claim 1 to a pest and/or a habitat thereof.

6. A composition comprising an effective amount of an active compound combination comprising, as components,
(a') at least one compound of formula (I) as claimed in claim 1, and
(b') at least one crop plant compatibility-improving compound selected from the group consisting of
S1) a compound of the formula

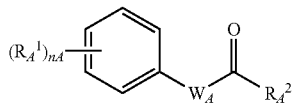
(S1)

where
$n_A$ is a natural number from 0 to 5,
$R_A^1$ is halogen, $(C_1-C_4)$-alkyl, $(C_1-C_4)$-alkoxy, nitro or $(C_1-C_4)$-haloalkyl,
$W_A$ is an unsubstituted or substituted divalent heterocyclic radical selected from the group consisting of the partially unsaturated or aromatic five-membered heterocycles having 1 to 3 ring heteroatoms of the N or O type, where at least one nitrogen atom and at most one oxygen atom is present in the ring,
$m_A$ is 0 or 1,
$R_A^2$ is $OR_A^3$, $SR_A^3$ or $NR_A^3R_A^4$ or a saturated or unsaturated 3- to 7-membered heterocycle having at least one nitrogen atom and up to 3 heteroatoms selected from the group consisting of O and S, which is joined to the carbonyl group in (S1) via the nitrogen atom and is unsubstituted or substituted by radicals selected from the group consisting of $(C_1-C_4)$-alkyl, $(C_1-C_4)$-alkoxy or optionally substituted phenyl,
$R_A^3$ is hydrogen or an unsubstituted or substituted aliphatic hydrocarbyl radical having a total of 1 to 18 carbon atoms,
$R_A^4$ is hydrogen, $(C_1-C_6)$-alkyl, $(C_1-C_6)$-alkoxy or substituted or unsubstituted phenyl,
$R_A^5$ is H, $(C_1-C_8)$-alkyl, $(C_1-C_8)$-haloalkyl, $(C_1-C_4)$-alkoxy-$(C_1-C_8)$-alkyl, cyano or $COOR_A^9$, where $R_A^9$ is hydrogen, $(C_1-C_8)$-alkyl, $(C_1-C_8)$-haloalkyl, $(C_1-C_4)$-alkoxy-$(C_1-C_4)$-alkyl, $(C_1-C_6)$-hydroxyalkyl, $(C_3-C_{12})$-cycloalkyl or tri-$(C_1-C_4)$-alkylsilyl, and
$R_A^6$, $R_A^7$, and $R_A^8$ are identical or different and are hydrogen, $(C_1-C_8)$-alkyl, $(C_1-C_8)$-haloalkyl, $(C_3-C_{12})$-cycloalkyl or substituted or unsubstituted phenyl;

S2) a compound of the formula

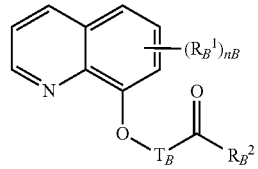
(S2)

where
$R_B^1$ is halogen, $(C_1-C_4)$-alkyl, $(C_1-C_4)$-alkoxy, nitro or $(C_1-C_4)$-haloalkyl,
$n_B$ is a natural number from 0 to 5,
$R_B^2$ is $OR_B^3$, $SR_B^3$ or $NR_B^3R_B^4$ or a saturated or unsaturated 3- to 7-membered heterocycle having at least one nitrogen atom and up to 3 heteroatoms selected from the group consisting of O and S, which is joined to the carbonyl group in (S2) via the nitrogen atom and is unsubstituted or substituted by radicals selected from the group consisting of $(C_1-C_4)$-alkyl, $(C_1-C_4)$-alkoxy or optionally substituted phenyl,
$R_B^3$ is hydrogen or an unsubstituted or substituted aliphatic hydrocarbyl radical having a total of 1 to 18 carbon atoms,
$R_B^4$ is hydrogen, $(C_1-C_6)$-alkyl, $(C_1-C_6)$-alkoxy or substituted or unsubstituted phenyl; and
$T_B$ is a $(C_1$ or $C_2)$-alkanediyl chain which is unsubstituted or substituted by one or two $(C_1-C_4)$-alkyl radicals or by $[(C_1-C_3)$-alkoxy]carbonyl;

S3) a compound of the formula

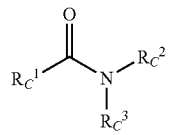
(S3)

where
$R_C^1$ is $(C_1-C_4)$-alkyl, $(C_1-C_4)$-haloalkyl, $(C_2-C_4)$-alkenyl, $(C_2-C_4)$-haloalkenyl or $(C_3-C_7)$-cycloalkyl, and
$R_C^2$ and $R_C^3$ are identical or different and are hydrogen, $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_1-C_4)$-alkylcarbamoyl-$(C_1-C_4)$-alkyl, $(C_2-C_4)$-alkenylcarbamoyl-$(C_1-C_4)$alkyl, $(C_1-C_4)$-alkoxy-$(C_1-C_4)$-alkyl, dioxolanyl-$(C_1-C_4)$-alkyl, thiazolyl, furyl, furylalkyl, thienyl, piperidyl, or substituted or unsubstituted phenyl, or $R_C^2$ and $R_C^3$ together form a substituted or unsubstituted heterocyclic ring, S4) a compound of the formula

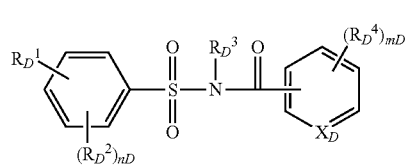
(S4)

where $X_D$ is CH or N, $R_D^1$ is CO—$NR_D^5R_D^6$ or NHCO—$R_D^7$, $R_D^2$ is halogen, $(C_1-C_4)$-haloalkyl, $(C_1-C_4)$-haloalkoxy, nitro, $(C_1-C_4)$-alkyl, $(C_1-C_4)$-alkoxy, $(C_1-C_4)$-alkylsulfonyl, $(C_1-C_4)$-alkoxycarbonyl or $(C_1-C_4)$-alkylcarbonyl, $R_D^3$ is hydrogen, $(C_1-C_4)$-alkyl, $(C_2-C_4)$-alkenyl or $(C_2-C_4)$-alkynyl, $R_D^4$ is halogen, nitro, $(C_1-C_4)$-alkyl, $(C_1-C_4)$-haloalkyl, $(C_1-C_4)$-haloalkoxy, $(C_3-C_6)$-cycloalkyl, phenyl, $(C_1-C_4)$-alkoxy, cyano, $(C_1-C_4)$-alkylthio, $(C_1-C_4)$-alkylsulfinyl, $(C_1-C_4)$-alkylsulfonyl, $(C_1-C_4)$-alkoxycarbonyl or $(C_1-C_4)$-alkylcarbonyl, $R_D^5$ is hydrogen, $(C_1-C_6)$-alkyl, $(C_3-C_6)$-cycloalkyl, $(C_2-C_6)$-alkenyl, $(C_2-C_6)$-alkynyl, $(C_5-C_6)$-cycloalkenyl, phenyl or 3- to 6-membered heterocyclyl containing $v_D$ heteroatoms selected from the group consisting of nitrogen, oxygen and sulfur, where the seven latter radicals are each substituted by $v_D$ substituents selected from the group consisting of halogen, $(C_1-C_6)$-alkoxy, $(C_1-C_6)$-haloalkoxy, $(C_1-C_2)$-alkylsulfinyl, $(C_1-C_2)$-alkylsulfonyl, $(C_3-C_6)$-cycloalkyl, $(C_1-C_4)$-alkoxycarbonyl, $(C_1-C_4)$-alkylcarbonyl and phenyl, and in the case of cyclic radicals also $(C_1-C_4)$-alkyl and $(C_1-C_4)$-haloalkyl, $R_D^6$ is hydrogen, $(C_1-C_6)$-alkyl, $(C_2-C_6)$-alkenyl or $(C_2-C_6)$-alkynyl, where the three latter radicals are each substituted by $v_D$ radicals selected from the group consisting of halogen, hydroxyl, $(C_1-C_4)$-alkyl, $(C_1-C_4)$-alkoxy and $(C_1-C_4)$-alkylthio, or $R_D^5$ and $R_D^6$ together with the nitrogen atom which bears them form a pyrrolidinyl or piperidinyl radical, $R_D^7$ is hydrogen, $(C_1-C_4)$-alkylamino, di-$(C_1-C_4)$-alkylamino, $(C_1-C_6)$-alkyl, or $(C_3-C_6)$-cycloalkyl, where the 2 latter radicals are substituted by $v_D$ substituents selected from the group consisting of halogen, $(C_1-C_4)$-alkoxy, $(C_1-C_6)$-haloalkoxy and $(C_1-C_4)$-alkylthio, and in the case of cyclic radicals also $(C_1-C_4)$-alkyl and $(C_1-C_4)$-haloalkyl, $n_D$ is 0, 1 or 2, $m_D$ is 1 or 2, and $v_D$ is 0, 1, 2 or 3;

S5) a hydroxyaromatic or aromatic-aliphatic carboxylic acid derivative (S5) selected from the group consisting of ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicyclic acid, 2-hydroxycinnamic acid, 1,2-dihydro-2-oxo-6-trifluoro-methylpyridine-3-carboxamide, and 2,4-dichlorocinnamic acid;

S6) a 1,2-dihydroquinoxalin-2-one (S6) selected from the group consisting of 1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydro-quinoxalin-2-one hydrochloride, 1-[2-(diethylamino)ethyl]-6,7-dimethyl-3-thiophen-2-ylquinoxalin-2(1H)-one, and 1-(2-methylsulfonylaminoethyl)-3-(2-thienyl)-1,2-dihydroquinoxalin-2-one;

S7) a compound of the formula

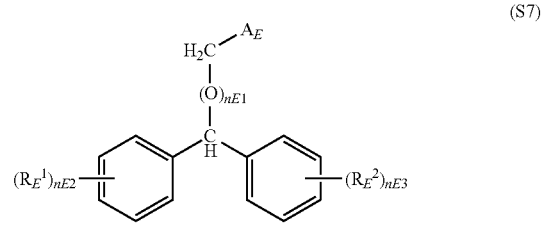

(S7)

where $R_E^1$, $R_E^2$ are each independently of one another halogen, $(C_1-C_4)$-alkyl, $(C_1-C_4)$-alkoxy, $(C_1-C_4)$-haloalkyl, $(C_1-C_4)$-alkylamino, di-$(C_1-C_4)$-alkylamino or nitro;

$A_E$ is COOR$_E^3$ or COSR$_E^4$, $R_E^3$, $R_E^4$ are each independently of one another hydrogen, $(C_1-C_4)$-alkyl, $(C_2-C_6)$-alkenyl, $(C_2-C_4)$-alkynyl, cyanoalkyl, $(C_1-C_4)$-haloalkyl, phenyl, nitrophenyl, benzyl, halobenzyl, pyridinylalkyl or alkylammonium, $n_E^1$ is 0 or 1, and $n_E^2$, $n_E^3$ are each independently of one another 0, 1 or 2;

S8) a compound of the formula

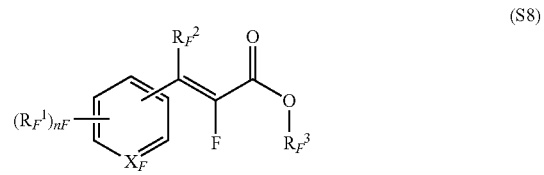

(S8)

where $X_F$ is CH or N, $n_F$ in the case that $X_F$=N is an integer from 0 to 4 and in the case that $X_F$=CH is an integer from 0 to 5, $R_F^1$ is halogen, $(C_1-C_4)$-alkyl, $(C_1-C_4)$-haloalkyl, $(C_1-C_4)$-alkoxy, $(C_1-C_4)$-haloalkoxy, nitro, $(C_1-C_4)$-alkylthio, $(C_1-C_4)$-alkylsulfonyl, $(C_1-C_4)$-alkoxycarbonyl, optionally substituted phenyl, or optionally substituted phenoxy, $R_F^2$ is hydrogen or $(C_1-C_4)$-alkyl, and $R_F^3$ is hydrogen, $(C_1-C_8)$-alkyl, $(C_2-C_4)$-alkenyl, $(C_2-C_4)$-alkynyl, or aryl, where each of the aforementioned carbon-containing radicals is unsubstituted or substituted by one or more identical or different radicals selected from the group consisting of halogen and alkoxy, or salts thereof;

S9) a 3-(5-tetrazolylcarbonyl)-2-quinolone (S9) selected from the group consisting of 1,2-dihydro-4-hydroxy-1-ethyl-3-(5-tetrazolylcarbonyl)-2-quinolone and 1,2-dihydro-4-hydroxy-1-methyl-3-(5-tetrazolylcarbonyl)-2-quinolone;

S10) a compound of the formula

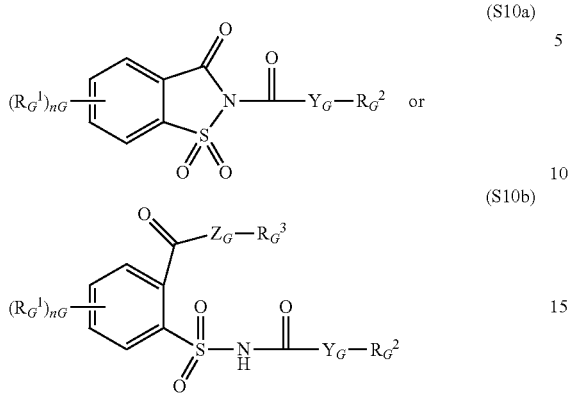

where
$R_G^1$ is halogen, $(C_1$-$C_4)$-alkyl, methoxy, nitro, cyano, $CF_3$, or $OCF_3$,
$Y_G$ and $Z_G$ are each independently of one another O or S,
$n_G$ is an integer from 0 to 4,
$R_G^2$ is $(C_1$-$C_{16})$-alkyl, $(C_2$-$C_6)$-alkenyl, $(C_3$-$C_6)$-cycloalkyl, aryl, benzyl, or halobenzyl, and
$R_G^3$ is hydrogen or $(C_1$-$C_6)$-alkyl;

S11) an oxyimino compound (S11) seed dressing selected from the group consisting of oxabetrinil ((Z)-1,3-dioxolan-2-ylmethoxyimino(phenyl)acetonitrile) (S11-1) used as seed dressing safener for millet against metolachlor damage, fluxofenim (1-(4-chlorophenyl)-2,2,2-trifluoro-1-ethanone O-(1,3-dioxolan-2-ylmethyl)-oxime) (S11-2) used as seed dressing safener for millet against metolachlor damage, and cyometrinil (CGA-43089, (Z)-cyanomethoxyimino(phenyl)-acetonitrile) (S11-3) used as seed dressing safener for millet against metolachlor damage;

S12) an isothiochromanone (S12) that is methyl [(3-oxo-1H-2-benzothiopyran-4(3H)-ylidene)methoxy]acetate (S12-1);

S13) naphthalic anhydride (1,8-naphthalenedicarboxylic anhydride) (513-1) used as seed dressing safener for corn against thiocarbamate herbicide damage, fenclorim (4,6-dichloro-2-phenylpyrimidine) (S13-2) used as safener for pretilachlor in sown rice, flurazole (benzyl 2-chloro-4-trifluoromethyl-1,3-thiazole-5-carboxylate) (513-3) used as seed dressing safener for millet against alachlor and metolachlor damage, CL 304415 (4-carboxy-3,4-dihydro-2H-1-benzopyran-4-acetic acid) (S13-4) used as a safener for corn against damage by imidazolinones, MG 191 (2-dichloromethyl-2-methyl-1,3-dioxolane) (513-5)) used as a safener for corn, MG-838 (2-propenyl 1-oxa-4-azaspiro[4.5]decane-4-carbodithioate) (S13-6), disulfoton (0,0-diethyl S-2-ethylthioethyl phosphorodithioate) (S13-7), dietholate (0,0-diethyl 0-phenyl phosphorothioate) (513-8), or mephenate (4-chlorophenyl methylcarbamate) (S13-9);

S14) an active compound which, in addition to herbicidal action against harmful plants, also has safener action on crop plants selected from the group consisting of dimepiperate (MY-93, S-1-methyl-1-phenylethylpiperidine-1-carbothioate) used as a safener for rice against damage by the herbicide molinate, daimuron (SK 23, 1-(1-methyl-1-phenylethyl)-3-p-tolylurea) used as a safener for rice against imazosulfuron herbicide damage, cumyluron (JC-940, 3-(2-chlorophenylmethyl)-1-(1-methyl-1-phenylethyl) urea) used as a safener for rice against damage by some herbicides, methoxyphenone (NK 049,3,3'-dimethyl-4-methoxybenzo-phenone) used as a safener for rice, and CSB (1-bromo-4-(chloromethylsulfonyl)benzene) used as a safener for rice;

S15) a compound of the formula

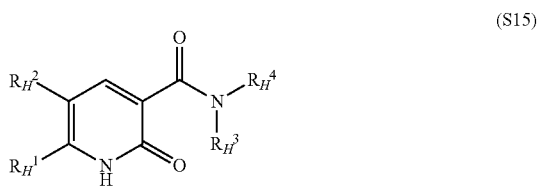

where
$R_H^1$ is a $(C_1$-$C_6)$-haloalkyl radical,
$R_H^2$ is hydrogen or halogen,
$R_H^3$ and $R_H^4$ are each independently hydrogen, $(C_1$-$C_{16})$-alkyl, $(C_2$-$C_{16})$-alkenyl or $(C_2$-$C_{16})$-alkynyl, where each of the latter 3 radicals is unsubstituted or substituted by one or more radicals selected from the group consisting of halogen, hydroxyl, cyano, $(C_1$-$C_4)$-alkoxy, $(C_1$-$C_4)$-haloalkoxy, $(C_1$-$C_4)$-alkylthio, $(C_1$-$C_4)$-alkylamine, di[$(C_1$-$C_4)$-alkyl]amino, [$(C_1$-$C_4)$-alkoxy]-carbonyl, [$(C_1$-$C_4)$-haloalkoxy]carbonyl, $(C_3$-$C_6)$-cycloalkyl which is unsubstituted or substituted, phenyl which is unsubstituted or substituted, and heterocyclyl which is unsubstituted or substituted,
or are $(C_3$-$C_6)$-cycloalkyl, $(C_4$-$C_6)$-cycloalkenyl, or $(C_3$-$C_6)$-cycloalkyl which is fused on one side of the ring to a 4 to 6-membered saturated or unsaturated carbocyclic ring, or $(C_4$-$C_6)$-cycloalkenyl which is fused on one side of the ring to a 4- to 6-membered saturated or unsaturated carbocyclic ring, where each of the latter 4 radicals is unsubstituted or substituted by one or more radicals selected from the group consisting of halogen, hydroxyl, cyano, $(C_1$-$C_4)$-alkyl, $(C_1$-$C_4)$-haloalkyl, $(C_1$-$C_4)$-alkoxy, $(C_1$-$C_4)$-haloalkoxy, $(C_1$-$C_4)$-alkylthio, $(C_1$-$C_4)$-alkylamino, di[$(C_1$-$C_4)$-alkyl]amino, [$(C_1$-$C_4)$-alkoxy]carbonyl, [$(C_1$-$C_4)$-haloalkoxy]-carbonyl, $(C_3$-$C_6)$-cycloalkyl which is unsubstituted or substituted, phenyl which is unsubstituted or substituted, and heterocyclyl which is unsubstituted or substituted, or
$R_H^3$ is $(C_1$-$C_4)$-alkoxy, $(C_2$-$C_4)$-alkenyloxy, $(C_2$-$C_6)$-alkynyloxy or $(C_2$-$C_4)$-haloalkoxy and
$R_H^4$ is hydrogen or $(C_1$-$C_4)$-alkyl, or
$R_H^3$ and $R_H^4$ together with the directly bonded nitrogen atom are a four- to eight-membered heterocyclic ring which optionally contain further ring heteroatoms selected from the group consisting of N, O and S, and which is unsubstituted or substituted by one or more radicals selected from the group consisting of halogen, cyano, nitro, $(C_1$-$C_4)$-alkyl, $(C_1$-$C_4)$-haloalkyl, $(C_1$-$C_4)$-alkoxy, $(C_1$-$C_4)$-haloalkoxy and $(C_1$-$C_4)$-alkylthio; and S16) an active compound which is used primarily as an herbicide but also having safener action on crop plants selected from the group consisting of (2,4-dichlorophenoxy)acetic acid (2,4-D), (4-chlorophenoxy) acetic acid, (R,S)-2-(4-chloro-o-tolyloxy)propionic acid (mecoprop), 4-(2,4-dichloro-phenoxy)butyric acid (2,4-DB), (4-chloro-o-tolyloxy)acetic acid (MCPA), 4-(4-chloro-o-tolyloxy)butyric acid, 4-(4-chlorophenoxy)butyric acid, 3,6-dichloro-2-methoxybenzoic acid (digamma), and 1-(ethoxycarbonyl) ethyl 3,6-dichloro-2-methoxybenzoate (lactidichlorethyl).

7. A method for controlling unwanted vegetation, comprising applying a composition as claimed in claim 6 to a plant and/or surroundings thereof.

8. A method for controlling unwanted vegetation, comprising applying a compound of formula (I) as claimed in claim 1, separately or in close temporal succession, to a plant and/or the surroundings thereof.

9. A method for controlling unwanted vegetation, comprising applying a crop plant compatibility-improving compound as claimed in claim 6, separately or in close temporal succession, to a plant and/or the surroundings thereof.

10. The compound of formula (I) as claimed in claim 1, in which
W represents hydrogen,
X represents methyl,
Y represents hydrogen,
Z represents methyl,
A and B together represent —$(CH_2)_2$—$CHOCH_3$—$(CH_2)_2$—, and
G represents

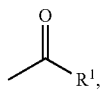

in which $R^1$ represents —$C(CH_3)_2C_2H_5$.

* * * * *